US006342220B1

(12) United States Patent
Adams et al.

(10) Patent No.: US 6,342,220 B1
(45) Date of Patent: Jan. 29, 2002

(54) AGONIST ANTIBODIES

(75) Inventors: Camellia W. Adams, Mountain View; Paul J. Carter, San Francisco; Brian M. Fendly, Half Moon Bay; Austin L. Gurney, Belmont, all of CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 08/918,148

(22) Filed: Aug. 25, 1997

(51) Int. Cl.$^7$ .............................................. A61K 39/395

(52) U.S. Cl. ................................ 424/153.1; 424/133.1; 424/135.1; 530/388.7; 530/387.1

(58) Field of Search ........................... 530/387.1, 388.7, 530/388.1; 424/133.1, 135.1, 153.1

(56) References Cited

U.S. PATENT DOCUMENTS

| | | | |
|---|---|---|---|
| 4,558,005 A | 12/1985 | Goldwasser et al. | |
| 4,626,507 A | 12/1986 | Trowbridge et al. | |
| 4,710,457 A | 12/1987 | Dupont et al. | |
| 5,635,388 A | 6/1997 | Bennett et al. | |
| 5,980,893 A | 11/1999 | Avraham et al. | |

FOREIGN PATENT DOCUMENTS

| | | |
|---|---|---|
| JP | 9289892 | 11/1997 |
| WO | WO 92/01047 | 1/1992 |
| WO | WO 92/20791 | 11/1992 |
| WO | WO 93/06213 | 4/1993 |
| WO | WO 93/11236 | 6/1993 |
| WO | WO 93/19172 | 9/1993 |
| WO | WO 95/01438 | 1/1995 |
| WO | WO9514930 | 6/1995 |
| WO | WO 95/15388 | 6/1995 |
| WO | WO 95/18858 | 7/1995 |
| WO | WO9527061 | 10/1995 |
| WO | WO9527062 | 10/1995 |
| WO | WO 95/28907 | 11/1995 |
| WO | WO 96/03438 | 2/1996 |

OTHER PUBLICATIONS

Debili et al. Blood vol. 85, No. 2, 1995, 391–401, 1995.*
Alexander et al., "Deficiencies in Progenitor Cells of Multiple Hematopoietic Lineages and Defective Megakaryocytopoiesis in Mice Lacking the Thrombopoietin Receptor c–Mp1" *Blood* 87:2162–2170 (1996).
Angchaisuksiri et al., "Effects of recombinant human thrombopoietin on megakaryocyte colony formation and megakaryocyte ploidy by human CD34+ cells in a serum–free system" *Br. J. Haematol.* 93:13–17 (1996).
Ault et al., "Recombinant Human Thrombopoietin Augments Spontaneous and ADP Induced Platelet Activation Both In Vitro and In Vivo" *Blood* 86:367a #1456 (1995).

Ault et al., "Recombinant Human Thrombopoietin Induces a Dose–Dependent Increase in Reticulated Platelets Which Precedes the Increase in Platelet Count, and Does Not Affect Platelet Lifespan in Mice" *Blood* 86:367a #1455 (1995).
Banu et al., "Modulation of Megakaryocytopoiesis by Thrombopoietin: The c–Mp1 Ligand" *Blood* 86:1331–1338 (1995).
Bartley et al., "Identification and Cloning of a Megakaryocyte Growth and Development Factor That is a Ligand for the Cytokine Receptor Mp1" *Cell* 77:1117–1124 (1994).
Basser et al., "Randomized, Double–Blind, Placebo–Controlled Phase I Trial of Pegylated Megakaryocyte Growth and Development Factor (PEG–rHuMGDF) Administered to Patients with Advanced Before and Cancer After Chemotherapy—Early Results" *Blood* 86:257a (Abstract 1014) (1995).
Begley et al., "Randomised, Double–Blind, Placebo–Controlled Phase I Trial of Pegylated Megakaryocyte Growth and Development Factor (PEG rHuMGDF) Administered to Patients with Advanced Cancer After Chemotherapy" *Proceedings of ASCO* 15:271 #719 (1996).
Bowe et al., "The Role of Agrin in Synapse Formation" *Annu–Rev–Neurosci.* 18:443–462 (1995).
Broudy et al., "Thrombopoietin (c–mp1 Ligand) Acts Synergistically With Erythropoietin, Stem Cell Factor, and Interleukin–11 to Enhance Murine Megakaryocyte Colony Growth and Increases Megakaryocyte Ploidy in Vitro" *Blood* 85:1719–1726 (1995).
Carter–Su et al., "Molecular Mechanism of Growth Hormone Action" *Annu–Rev.–Physiol* 58:187–207 (1996).
Carver–Moore et al., "Low Levels of Erythroid and Myeloid Progenitors in Thrombopoietin—and c–mp1—Deficient Mice" *Blood* 88:803–808 (1996).
Chang et al., "Regulation of TPO mRNA Expression and Protein Production: TPO Gene Regulation Appears Post Transcriptional, and Endogenous Levels are Inversely Correlated to Megakaryocyte Mass and Circulating Platelet Count" *Blood* 86:368a #1460 (1995).
Choi et al., "Platelets Generated in Vitro From Proplatelet–Displaying Human Megakaryocytes Are Functional," *Blood* 85:402–413 (1995).
Daw et al., "Regulation of Thrombopoiesis: In Vivo Response to a Single Injection of Murine PEG–Megakaryocyte Growth and Development Factor (MGDF)" *Blood* 86:897a #3575 (1995).
de Gabriele et al., "Physiology of the Regulation of Platelet Production" *Brit. J. Haemat.* 13:202–209 (1967).
de Gabriele et al., "Regulation of Platelet Production: 'Thrombopoietin'" *Br. J. Haematol.* 13:210–215 (1967).

(List continued on next page.)

Primary Examiner—Patrick J. Nolan
(74) Attorney, Agent, or Firm—Piper Marbury Rudnick & Wolfe LLP; Steven B. Kelber

(57) ABSTRACT

Various forms of c-mpl agonist antibodies are shown to influence the replication, differentiation or maturation of blood cells, especially megakaryocytes and megakaryocyte progenitor cells. Accordingly, these compounds may be used for treatment of thrombocytopenia.

14 Claims, 11 Drawing Sheets

OTHER PUBLICATIONS de Sauvage et al., "Physiological Regulation of Early and Late Stages of Megakaryocytopoiesis by Thrombopoietin" *Journal of Experimental Medicine* 183:651–656 (1996).

de Sauvage et al., "Stimulation of Megakaryocytopoiesis and Thrombpoiesis by the c–Mp1 Ligand" *Nature* 369:533–538 (Jun. 16, 1994).

Debili et al., "The Mp1–Ligand or Thrombopoietin of Megakaryocyte Growth and Differentiative Factor Has Both Direct Proliferative and Differentiative Activities on Human Megakaryocyte Progenitors" *Blood* 86:2516–2525 (1995).

Dechiara et al., "The Receptor Tyrosine Kinase MuSK Is Required for Neuromuscular Junction Formation in Vivo" *Cell* 85:501–512 (1996).

Deng et al., "An agonist murine monoclonal antibody to the human c–MPL receptor stimulates in vitro megakaryocytopoiesis" *Exp. Hematology* 24:1072 (abstract #260) (1996).

Eaton et al., "Biological Activity of Human Thrombopoietin (TPO), the c–mp1 Ligand, and TPO Variants and the Chromosomal Localization of TPO" *Blood* 84(suppl. 1):241a #948 (1994).

Emmons et al., "Human Thrombopoietin Levels Are High When Thrombocytopenia Is Due to Megakaryocyte Deficiency and Low When Due to Increased Platelet Destruction" *Blood* 87:4068–4071 (1996).

Fanucchi et al., "Safety and Biologic Effects of Pegylated Megakaryocyte Growth and Development Factor (PEG–rHuMGDF) in Lung Cancer Patients Receiving Carboplatin and Paclitaxel: Randomized, Placebo–Controlled Phase I Study" *Proceedings of ASCO* 15:271 #720 (1996).

Farese et al., "Combined Administration of Recombinant Human Megakaryocyte Growth and Development Factor and Granulocyte Colony–stimulating Factor Enhances Multilineage Hematopoietic Reconstitution in Nonhuman Primates after Radiation–induced Marrow Aplasia" *J. Clin. Invest.* 97:2145–2151 (1996).

Farese et al., "Recombinant Human Megakaryocyte Growth and Development Factor Stimulates Thrombocytopoiesis in Normal Nonhuman Primates" *Blood* 86:54–59 (1995).

Fibbe et al., "Accelerated Reconstitution of Platelets and Erythrocytes After Syngeneic Transplantation of Bone Marrow Cells Derived From Thrombopoietin Pretreated Donor Mice" *Blood* 86:3308–3313 (1995).

Fielder et al., "Regulation of Thrombopoietin Levels by c–mp1–Mediated Binding to Platelets" *Blood* 87:2154–2161 (1996).

Gautam et al., "Defective Neuromuscular Synaptogenesis in Agrin–Deficient Mutant Mice" *Cell* 85:525–535 (1996).

Glass et al., "Agrin Acts via a MuSK Receptor Complex" *Cell* 85:513–523 (1996).

Godfrey et al., "Components of Torpedo Electric Organ and Muscle That Cause Aggregation of Acetylcholine Receptors on Cultured Muscle Cells" *Journal of Cell Biology* 99:615–627 (1984).

Gordon et al., "Growth Factors Affecting Human Thrombocytopoiesis: Potential Agents for the Treatment of Thrombocytopenia" *Blood* 80(2):302–307 (Jul. 15, 1992).

Gurney et al., "Distinct regions of c–Mp1 cytoplasmic domain are coupled to the JAK–STAT signal transduction pathway and Shc phosphorylation" *Proc. Natl. Acad. Sci. USA* 92:5292–5296 (1995).

Gurney et al., "Thrombocytopenia in c–mp1–Deficient Mice" *Science* 265:1445–1447 (1994).

Harker et al., "Regulation of Platelet Production and Function by Megakaryocyte Growth and Development Factor in Nonhuman Primates" *Blood* 87:1833–1844 (1996).

Hokom et al., "Pegylated Megakaryocyte Growth and Development Factor Abrogates the Lethal Thrombocytopenia Associated with Carboplatin and Irradiation in Mice" *Blood* 86(12):4486–4492 (1995).

Hollinger et al., "Diabodies: Small Bivalent and Bispecific Antibody Fragments" *Proc. Natl. Acad. Sci. USA* 90:6444–6448 (1993).

Kabaya et al., "Inprovment of Thrombocytopenia After Bone Marrow–Transplantation by Recombinant Human Thrombopoietin (rhTPO) in mice" *Blood* 86:114a #443 (1995).

Kato et al., "Essential Structure for Biological Activity of Thrombopoietin" *Blood* 86 (suppl. 1): 365a #1448 (1995).

Kaushansky et al., "Promotion of Megakaryocyte Progenitor Expansion and Differentiation by the c–Mp1 Ligand Thrombopoietin" *Nature* 369:568–571 (Jun. 16, 1994).

Kaushansky et al., "Thrombopoietin Expands Erythroid Progenitors, Increases Red Cell Production, and Enhances Erythroid Recovery after Myelosuppressive Therapy" *Journal of Clinical Investigation* 96:1683–1687 (1995).

Kaushansky et al., "Thrombopoietin expands erythroid, granulocyte–macrophage, and megakaryocytic progenitor cells in normal and myelosuppressed mice" *Exp. Hematology* 24:265–269 (1996).

Kleiman et al., "Testing the Agrin Hypothesis" *Cell* 85:461–464 (1996).

Kobayashi et al., "Thrombopoietin Supports Proliferation of Human Primitive Hemapoietic Cells in Synergy With Steel Factor and/or Interleukin–3" *Blood* 88:429–436 (1996).

Kortt et al., "Recombinant anti–sialidase single–chain variable fragment antibody—Characterization, formation of dimer and higher–molecular–mass multimers and the solution of the crystal structure of the single–chain variable fragment/sialidase complex" *European Journal of Biochemistry* 221:151–157 (1994).

Ku et al., "Thrombopoietin, the Ligand for the Mp1 Receptor, Synergizes With Steel Factor and Other Early Acting Cytokines in Supporting Proliferation of Primitive Hematopoietic Progenitors of Mice" *Blood* 87:4544–4551 (1996).

Kuter et al., "Appearance of a Megakaryocyte Growth–promoting Activity, Megapoietin, During Acute Thrombocytopenia in the Rabbit" *Blood* 84(5):1464–1472 (1994).

Kuter et al., "The purification of megapoietin: A physiological regulator of magakaryocyte growth and platelet production" *Proc. Natl. Acad. Sci. USA* 91:11104–11108 (1994).

Leonard et al., "Recombinant Human Interleukin–11 Stimulates Multilineage Hematopoietic Recovery in Mice After a Myelosuppressive Regimen of Sublethal Irradiation and Carboplatin" *Blood* 83:1499–1506 (1994).

Lok et al., "Cloning and Expression of Murine Thrombopoietin cDNA and Stimulation of Platelet Production in vivo" *Nature* 369:565–568 (Jun. 16, 1994).

McDonald, "Thrombopoietin: Its Biology, Clinical Aspects, and Possibilities" *The American Journal of Pediatric Hematology/Oncology* 14(1):8–21 (1992).

Meng et al., "TPO Regulation Following Bone Marrow Transplantation" *Blood* 86:313a #1237 (1995).

Methia et al., "Oligodeoxynucleotides Antisense to the Proto–oncogene c–Mp1 Specifically Inhibit in vitro Megakaryocytopoiesis" *Blood* 82(5):1395–1401 (1993).

Molineux et al., "Effects of Treatment with MGDF and G–CSF on the Acceleration of Simultaneous Neutrophil and Platelet Recovery After Bone Marrow Transplant in Mice" *Blood* 86:227a #897 (1995).

Montrucchio et al., "Effects of Recombinant Human Megakaryocyte Growth and Development Factor on Platelet Activation" *Blood* 87:2762–2768 (1996).

Neelis et al., "Preclinical Evaluation of Thrombopoietin in Rhesus Monkeys" *Blood* 86:256a #1011 (1995).

Nichol et al., "Megakaryocyte Growth and Development Factor" *J. Clin. Invest.* 95:2973–2978 (1995).

Nitkin et al., "Identification of Agrin, A Synaptic Organizing Protein from Torpedo Electric Organ" *Journal of Cell Biology* 105:2471–2478 (1987).

O'Toole et al., "Alternative splicing of agrin regulates its binding to heparin, alpha–dystroglycan, and the cell surface" *Natl. Acad. Sci. USA* 93:7369–7374 (1996).

Oda et al., "Thrombopoietin Primes Human Platelet Aggregation Induced by Shear Stress and by Multiple Agonists" *Blood* 87:4664–4670 (1996).

Oh et al., "Serum Thrombopoietin Levels in Cyclic Thrombocytopenia" *Blood* 87:4918 (1996).

Perisic et al., "Crystal structure of a diabody, a bivalent antibody fragment" *Structure* 2:1217–1226 (1994).

Rasko et al., "In Vitro Studies From a Phase I Randomized, Blinded Trial of Pegylated Megakaryocyte Growth and Development Factor (PEG–rHuMGDF)" *Blood* 86:497a (Abstract 1978) (1995).

Ruegg et al., "The Agrin Gene Codes for a Family of Basal Lamina Protiens that Differ in Function and Distribution" *Neuron* 8:691–699 (1992).

Rui et al., "JAK2 Activation and Cell Proliferation Induced by Antibody–Mediated Prolactin Receptor Dimerization" *Endocrinology* 135(4):1299–1306 (1994).

Rupp et al., "Structure and Expression of a Rat Agrin" *Neuron* 6:811–823 (1991).

Shivdasani et al., "Transcription Factor NF–E2 Is Required for Platelet Formation Independent of the Actions of Thrombopoietin/MGDF in Megakaryocyte Development" *Cell* 81:695–704 (1995).

Sitnicka et al., "The Effect of Thrombopoietin on the Proliferation and Differentiation of Murine Hematopoietic Stem Cells" *Blood* 87:4998–5005 (1996).

Sohma et al., "Molecular Cloning and Chromosomal Localization of the Human Thrombopoietin Gene" *FEBS Letters* 353(1):57–61 (1994).

Sprugel et al., "Recombinant Human Thrombopoietin Stimulates Platelet Responses in Cynomolgus Monkeys" *Blood* 86:20a #69 (1995).

Stoffel et al., "Thrombopoietin in thrombocytopenic Mice: Evidence Against Regulation at the mRNA Level and for a Direct Regulatory Role of Platelets" *Blood* 87:567–573 (1996).

Thomas et al., "Dendritic Cells: Origin and Differentiation" *Stem Cells* 14:196–206 (1996).

Toombs et al., "Megakaryocyte Growth and Development Factor (MGDF) Moderately Enhances In–Vitro Platelet Aggregation" *Thrombosis Research* 80:23–33 (1995).

Toombs et al., "Megakaryocyte Growth and Development Factor (MGDF) Promotes Platelet Production in Vivo Without Affecting in Vivo Thrombosis" *Blood* 86:369a #1466 (1995).

Tsim et al., "cDNA That Encodes Active Agrin" *Neuron* 8:677–689 (1992).

Ulich et al., "Systemic Hematologic Effects of PEG–rHuMGDF–Induced Megakaryocyte Hyperplasia in Mice" *Blood* 87(12):5006–5015 (1996).

Vainchenker et al., "Megakaryocytopoiesis: cellular aspects and regulation" *Critical Reviews in Oncology/Hematology* 20:165–192 (1995).

Valenzuela et al., "Receptor Tyrosine Kinase Specific for the Skeletal Muscle Lineage: Expression in Embryonic Muscle, at the Neuromuscular Junction, and after Injury" *Neuron* 15:573–584 (1995).

Wendling et al., "c–Mp1 Ligand is a Humoral Regulator of Megakaryocytopoiesis" *Nature* 369:571–574 (1994).

Winton et al., "Prediction of a threshold and optimally effective thrombocytopoietic dose of recombinant human thrombopoietin (rhTPO) in nonhuman primates based on murine pharmacokinetic data" *Experimental Hematology* 23(8):879 (1995).

Xie et al., "Direct demonstration of MuSK involvement in acetylcholine receptor clustering through identification of agonist scFv." *Nature Biotechnology* 15:768–771 (1997).

Zeigler et al., "In Vitro Megakaryocytopoietic and Thrombopoietic Activity of c–mp1 Ligand (TPO) on Purified Murine Hematopoietic Stem Cells" *Blood* 84(12):4045–4052 (1994).

Avraham et al., "Interaction of human bone marrow fibroblasts with megakaryocytes: role of the c–kit ligand" *Blood* 80(7):1679–1684 (1992).

Avraham et al., "Modulation of megakaryocytopoiesis by human basic fibroblast growth factor" *Blood* 83((8)):2162–2132 (1994).

Azrin et al., "Preparation, characterization, and evaluation of a monoclonal antibody against the rabbit platelet glycoprotein IIb/IIIa in an experimental angioplasty model" *Circulation Research* 75:268–277 (1994).

Barclay et al., "Rapid isolation of monoclonal antibodies specific for cell surface differentiation antigens" *Proc. Natl. Acad. Sci. USA* 83:4336–4340 (1986).

Borrebaeck, Carl A.K., "Strategy for the production of human monoclonal antibodies using in vitro activated B cells" *J. Immunol. Methods* 123:157–165 (1989).

Coller, "Diagnostic and therapeutic applications of anti-platelet monoclonal antibodies" *Biorheology* 24:649–658 (1987).

Coller, "A murine monoclonal antibody that completely blocks the binding of fibrinogen to platelets produces a thrombasthenic–like state in normal platelets and binds to glycoproteins IIb and/or IIIa" *J. Clin. Invest.* 72:325–338 (1983).

Coller et al., "Studies with a murine monoclonal antibody that abolishes ristocetin–inducing binding of von Willebrand Factor to Platelets: Additional evidence in support of GPIb as a platelet receptor for von Willebrand Factor" *Blood* 61(1):99–110 (1983).

Debili et al., "The Mp1 Receptor is Expressed in the Megakaryocytic Lineage from Late Progenitors to Platelets" *Blood* 85((2)):391–401 (1995).

Deng et al., "An agonist murine monoclonal antibody to the human c–mp1 receptor simulates in vitro megakaryocytopoiesis" *Exp. Hematol.* (abstract 260, Aug. 23–27, 1996) 24:1072 (1996).

Drexler et al., "Thrombopoietin: expression of its receptor MPL and proliferative effects on leukemic cells" *Leukemia* 10:1405–1421 (1996).

Gilbert et al., "Production of a human monoclonal anti–epithelial cell surface antibody derived from a patient with *Pemphigus Vulgaris*" *Journal of Autoimmunity* 5:173–182 (1992).

Grossman et al., "Thrombopoietin accelerates platelet, red blood cell, and neutrophil recovery in myelosuppressed mice" *Exp. Hematology* 24:1238–1246 (1996).

Kaushansky et al., "Thrombopoietin, the Mp1 ligand, is essential for full megakaryocyte development" *Proc. Natl. Acad. Sci. USA* 92:3234–3238 (1995).

Komatsu et al., "Growth and Differentiation of a Human Megakaryoblastic Cell Line, CMK" *Blood* 74(1):42–48 (Jul. 1989).

Meyer et al., "Isolation and characterization of monoclonal antibodies directed against plant plasma membrane and cell wall epitopes" *Journal of Cell Biology* 107:163–175 (1988).

Mignotte et al., "Structure and Transcription of the Human c–Mp1 Gene (MPL)" *Genomics* 20:5–12 (1994).

Parren, "Preparation of genetically engineered monoclonal antibodies for human immunotherapy" *Human. Antibod. Hybridomas* 3:137–145 (1992).

Reverter et al., "Inhibition of platelet–mediated, tissue factor–induced thrombin generation by the mouse/human chimeric 7E3 antibody" *J. Clin. Invest.* 98(3):863–874 (1996).

Vigon et al., "Characterization of the Murine Mp1 Photo–oncogene, a Member of the Hematopoietic Cytokine Receptor Family: Molecular Cloning, Chromosomal Location and Evidence for a Function in Cell Growth" *Oncogene* 8:2607–2615 (1993).

Vigon et al., "Molecular Cloning and Characterization of Mp1, the Human Homolog of the v–Mp1 Oncogene: Identification of a Member of the Hematopoietic Growth Factor Receptor Superfamily" *Proc. Natl. Acad. Sci. USA* 89:5640–5644 (1992).

B. Deng, et al., "An Agonist Murine Monoclonal Antibody to Tehhuman C–MPL Receptor Stimulates In Vitro Megakaryocytopoiesis", Experimental Hematology, vol. 24, No. 9, Aug. 1996, p. 260.

H–H Xie, et al. "Direct Demonstration of Musk Involvement in Acetylcholine Receptor Clustering Through Identification of Agonist SCFV", Nature Biotechnology, vol. 15, Aug. 1997, pp. 768–771.

C. Adams, et al., "Development of Potent Agaonist Antibodies to C–MPL From a Human SCFV Phage Display Libray" Blood, vol. 90, No. 10, Suppl. 1, Part 1 of 2, Nov. 15, 1997, p. 55A XP002095743.

Patent Abstracts of Japan, vol. 098, No. 003, Feb. 27, 1998 & JP 09 289892 A (Yamanouchi Pharmaceuit Co Ltd), Nov. 11, 1997.

* cited by examiner

```
       VH
          F1                                      CDR1      F2
10F6    1  MAQVQLQESGGEMKKPGESLKISCKGYGYSFA TSWIG WVRQMPGRGLEWM
5E5     1  MAEVQLVQSGGGLVKPGGSLRLSCAASGFTFS DYYMS WIRQAPGKGLEWV
10D10   1  MAEVQLVQSGGGVVQPGGSLSLSCAVSGITLR TYGMH WVRQAPGKGLEWV
12B5    1  MAQVQLVQSGGGLVRPGGSLSLSCAVSGITLR TYGMH WVRQAPGKGLEWV
12D5    1  MAQVQLVESGGGLVKPGGSLRLSCAASGFTFS SHNMN WVRQAPGKGLEWV
12E10   1  MAQVQLQQSGPGLVKPSETLSLTCTVSGDSIS SYYWS WIRQPPGKGLEWI

CDR2                        F3
10F6   51  A IMYPGNSDTRHNPSFEDQVTMS ADTSINTAYLQWSSLKASDTAMYYCAR
5E5    51  S YISSSGSTIYYADSVKGRFTIS RDNSKNTLYLQMNSLRAEDTAVYYCAR
10D10  51  A GISFDGRSEYYADSVKGRFTIS RDNSKNTLYLQMNSLRAEDTAVYYCAR
12B5   51  A GISFDGRSEYYADSVQGRFTIS RDSSKNTLYLQMNSLRAEDTAVYYCAR
12D5   51  S SISSSSSYIYYADSVKGRFTIS RDNAKNSLYLQMNSLRAEDTAVYYCAR
12E10  51  G YIYYSGS-TNYNPSLKSRVTIS VDTSKSQFSLKLSSVTAADTAVYYCAR

CDR3          F4               VL    F1
10F6  101  AGVAGGAFDL WGKGTMVTVSSGGGGSGGGGSGGGGSQSVLTQ-PASVSGS
5E5   101  -WSGEDAFDI WGQGTMVTVSSGGGGSGGGGSGGGGSDIVMTQSPSTLSAS
10D10 101  -DRGSYGMDV WGRGTMVTVSSGGGGSGGGGSGGGGSDIQMTQSPSTLSAS
12B5  101  -G-AHYGFDI WGQGTMVTVSSGGGGTGGGGSGGGGSDIQMTQSPSTLSAS
12D5  101  -DRGSTGMDV WGRGTLVTVSSGGGGSGGGGSGGGGSDIQMTQSPSTLSAS
12E10 100  ----GRYFDV WGRGTMVTVSSGGGGSGGGGSGGGGSSYVLTQ-PPSVSGS

CDR1           F2            CDR2
10F6  150  PGQSITISC TGTSSGVGGYNYVS WYQQHPGKAPKLLIY GNSNRPS GVPDR
5E5   150  VGDRVAITC RASE---GIYHWLA WYQQKPGKAPKLLIY KASSLAS GAPSR
10D10 150  IGDRVTITC RASE---GIYHWLA WYQQKPGKAPKLLIY KASSLAS GAPSR
12B5  149  IGDRVTITC RASE---GIYHWLA WYQQKPGKAPKLLIY KASSLAS GAPSR
12D5  150  IGDRVTITC RASE---GIYHWLA WYQQKPGKAPKLLIY KASSLAS GAPSR
12E10 145  PGQSITISC TGTSSDVGGYNYVS WYQQHPGKAPKLMIY EGSKRPS GVSNR

F3                        CDR3          F4
10F6  200  FSASKSGNTASLTISGLQAEDEADYFC STYAPPGIIM FGGGTKLTVLGAA
5E5   197  FSGSGSGADFTLTISSLQPDDFATYYC QQYSNYPL-T FGGGTKLEVKRAA
10D10 197  FSGSGSGTDFTLTISSLQPDDFATYYC QQYSNYPL-T FGGGTKLEILRAA
12B5  196  FSGSGSGTDFTLTISSLQPDDFATYYC QQYSNYPL-T FGGGTELEIKRAA
12D5  197  FSGSGSGTDFXTISSLQPDDFATYYC  QQYSNYPL-T FGGGTKLEIKRAA
12E10 195  FSGSKSGNTASLTISGLQAEDEADYYC SSYTTRSTRV FGGGTKLTVLGAA
```

*FIG._1*

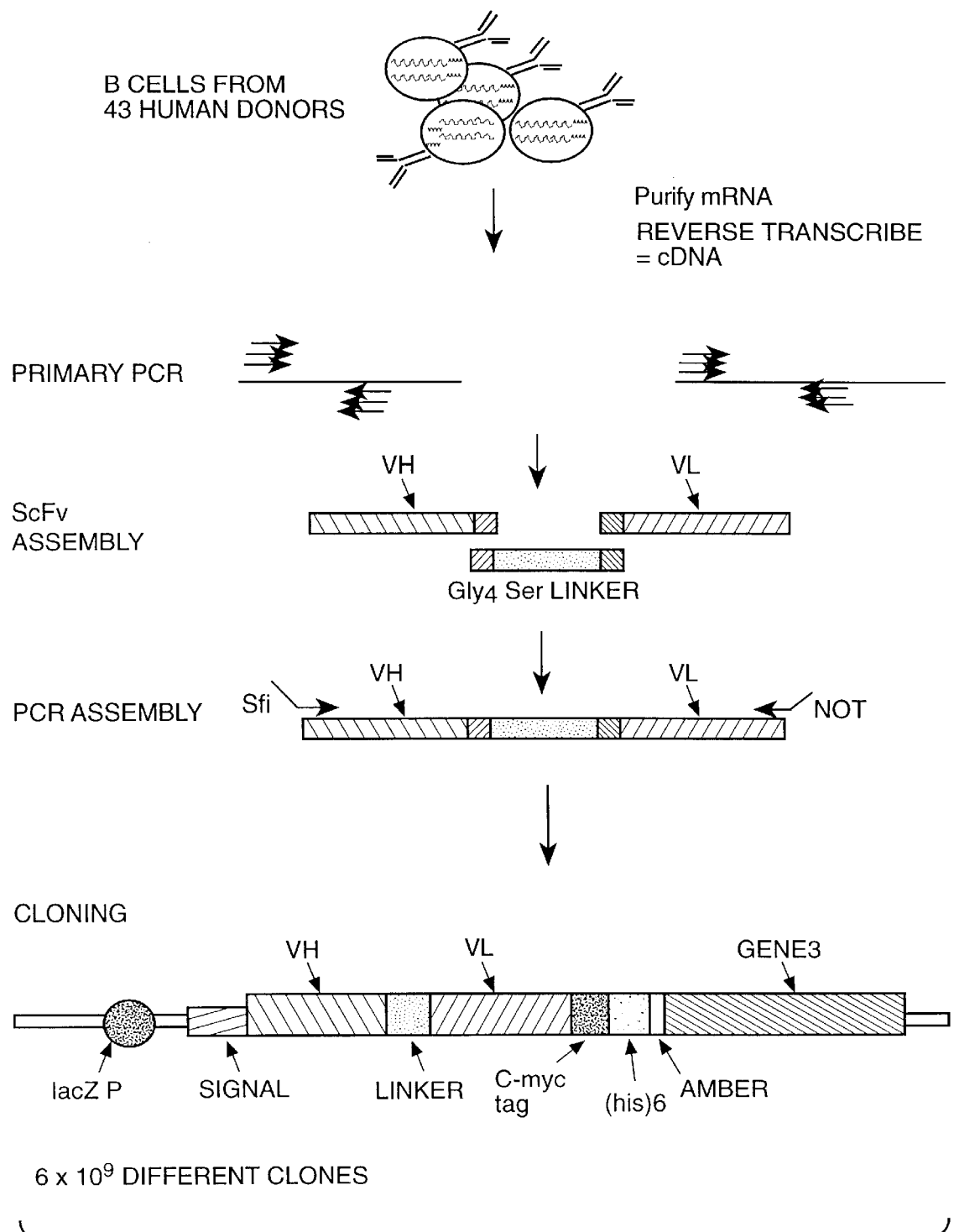
FIG._2

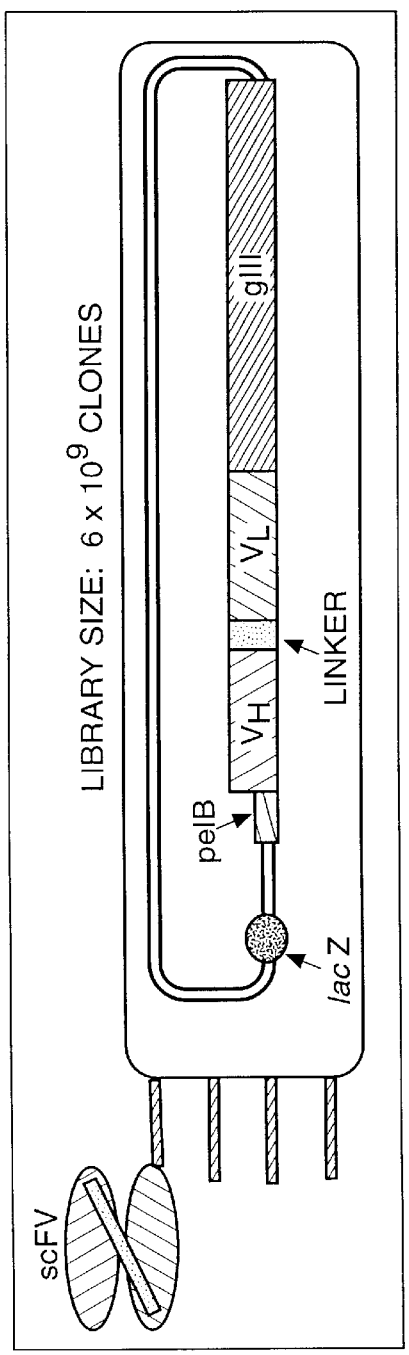
FIG._3
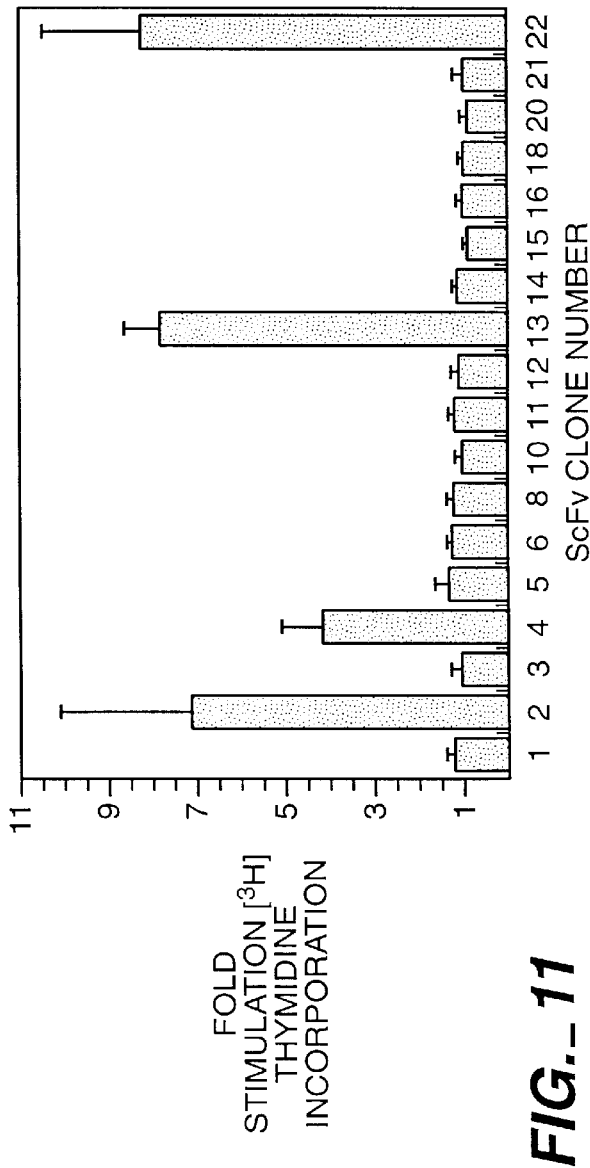
FIG._11

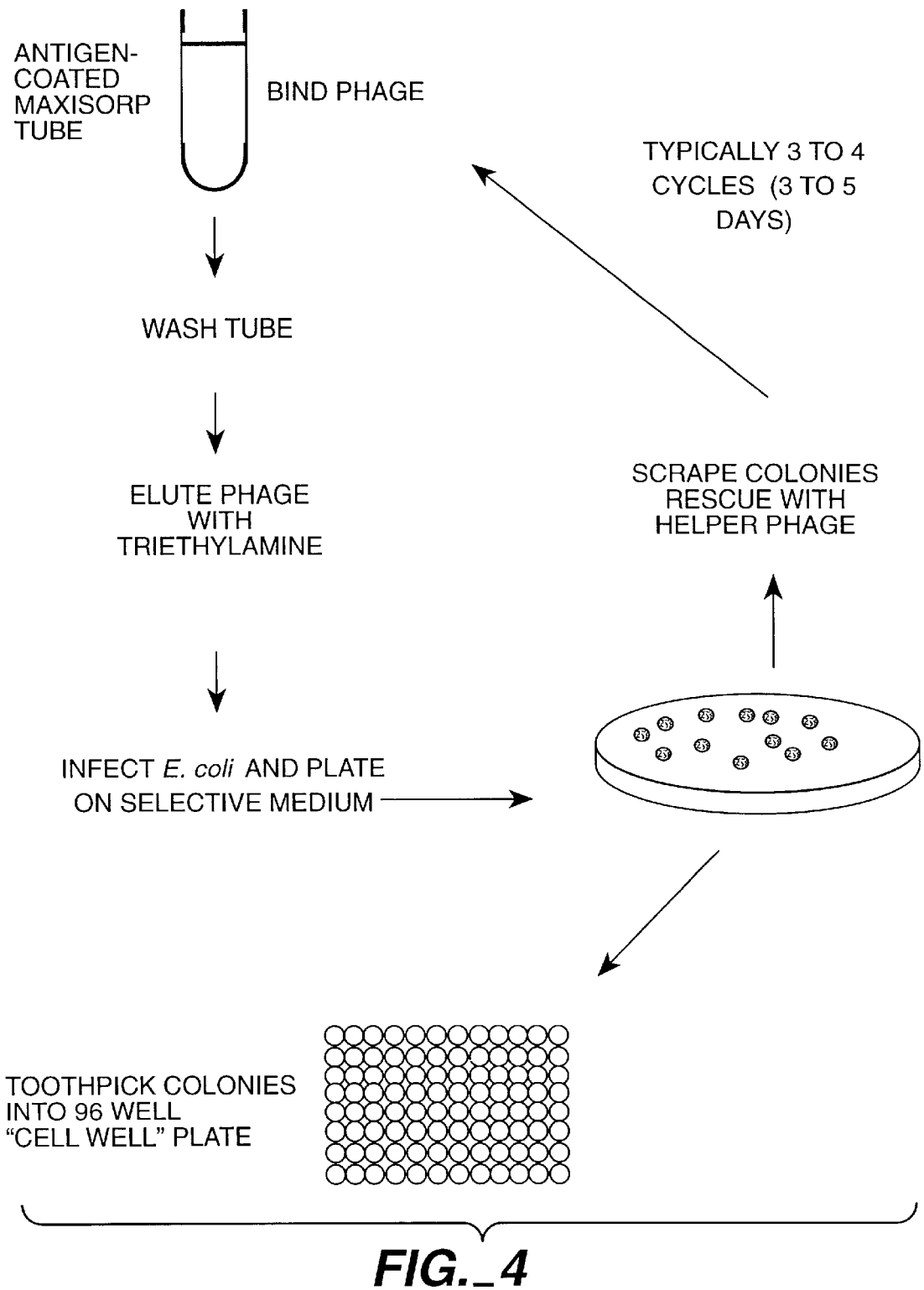
FIG._4

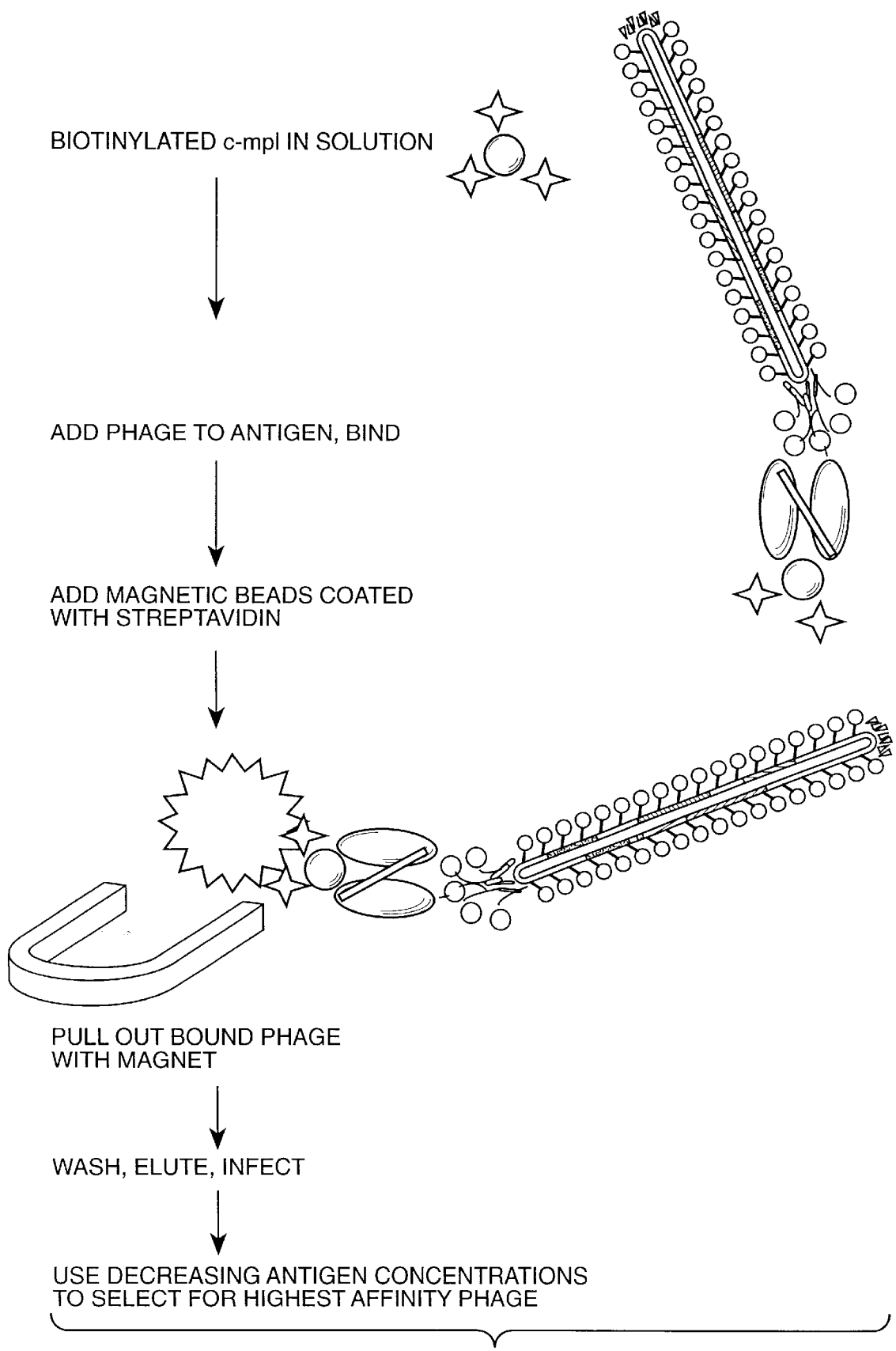
FIG._5

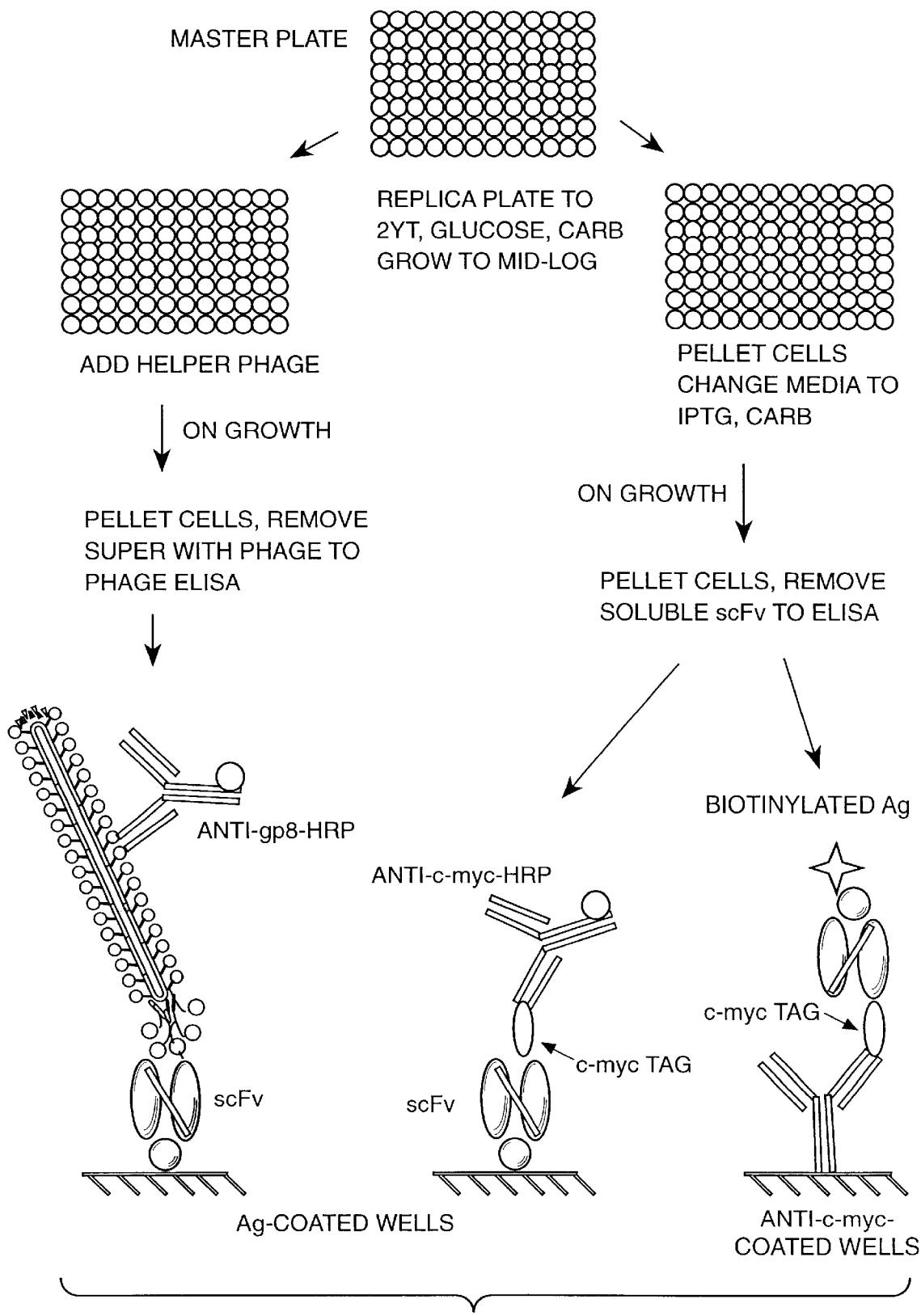
FIG._6

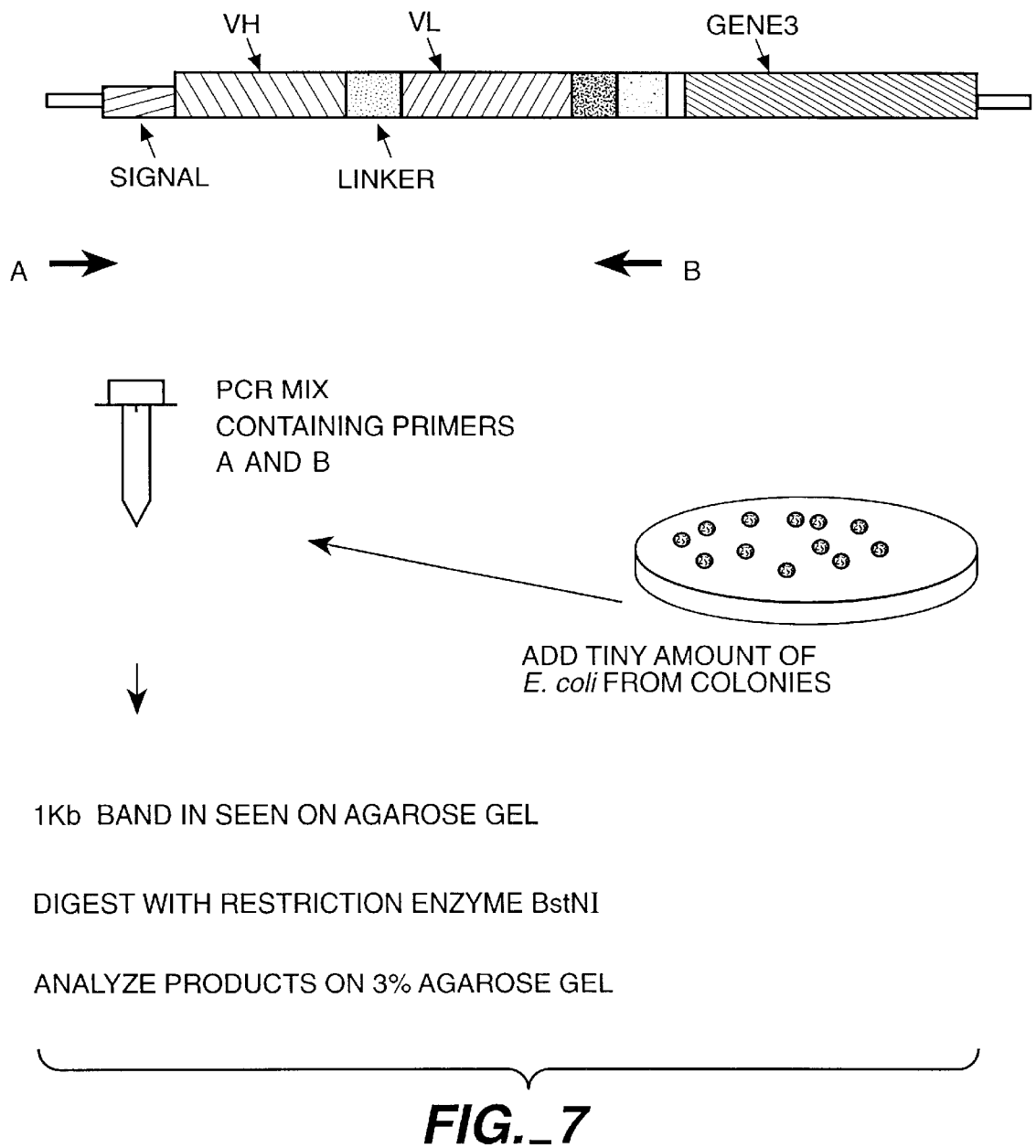
FIG._7

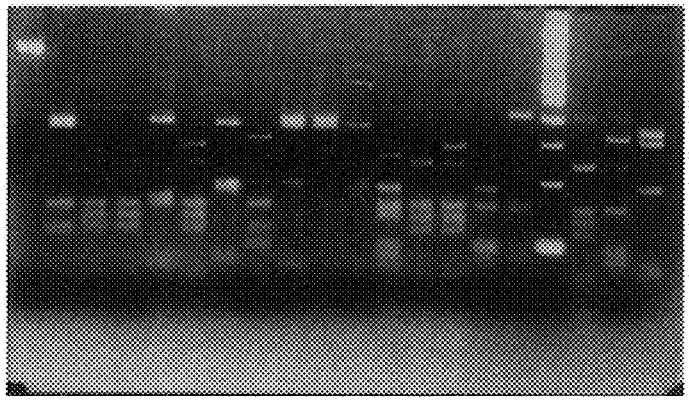
FIG._8A
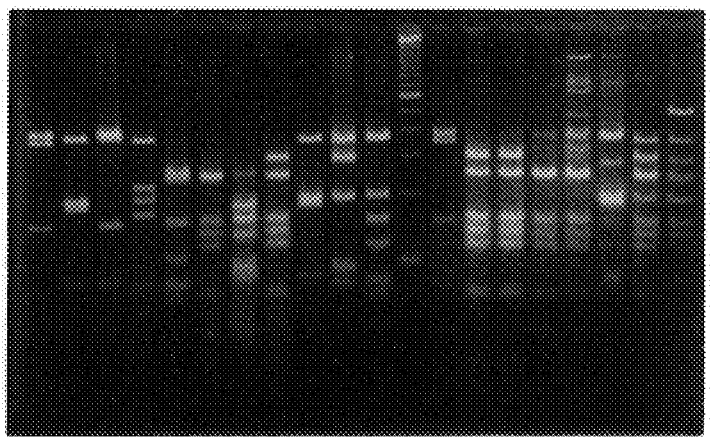
FIG._8B
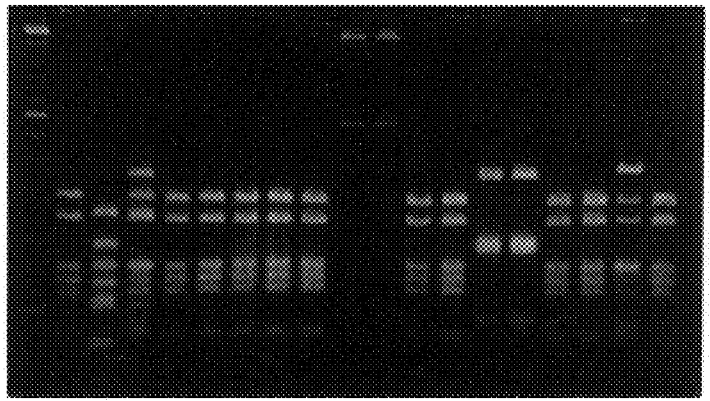
FIG._8C

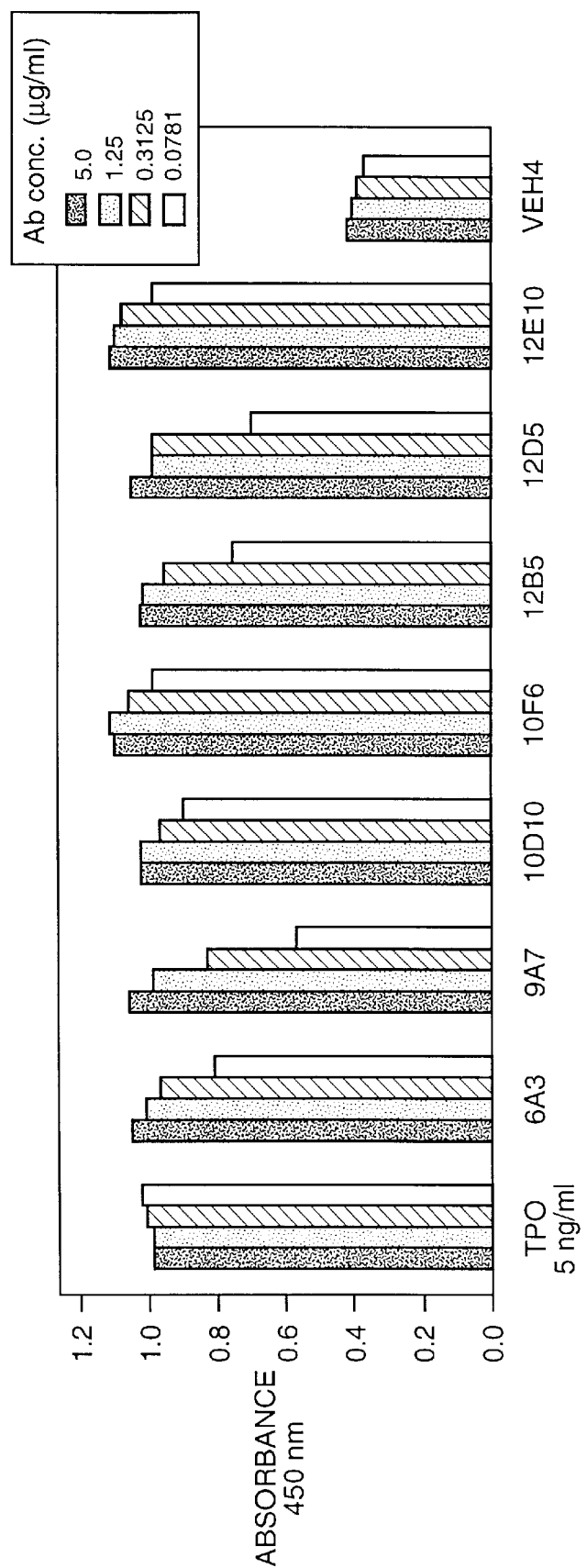
FIG._9

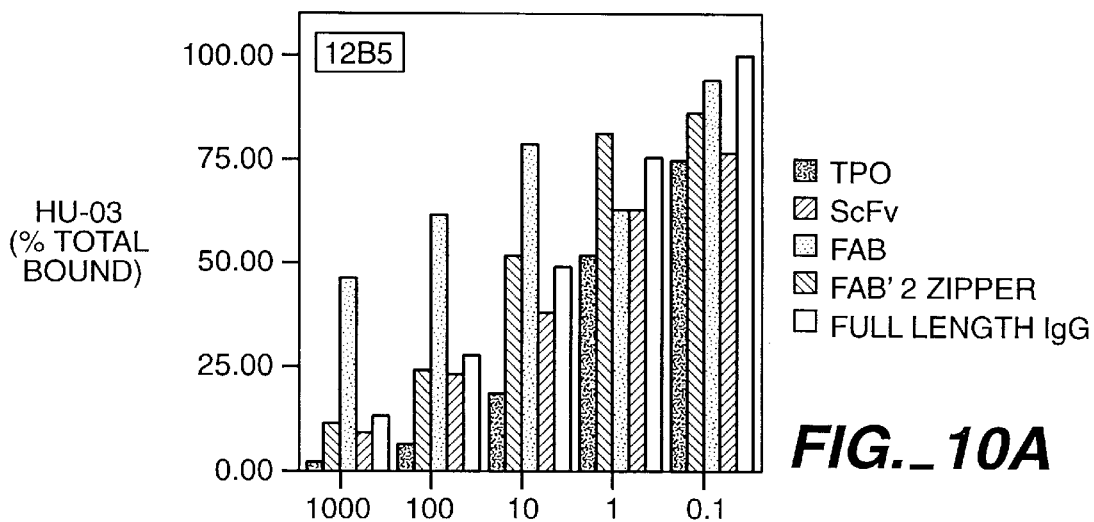
FIG._10A
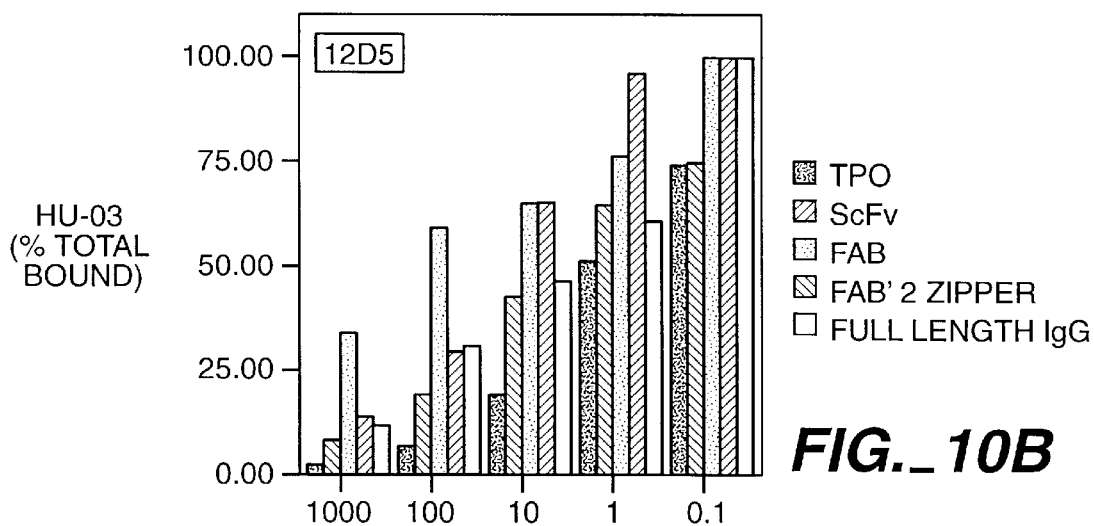
FIG._10B
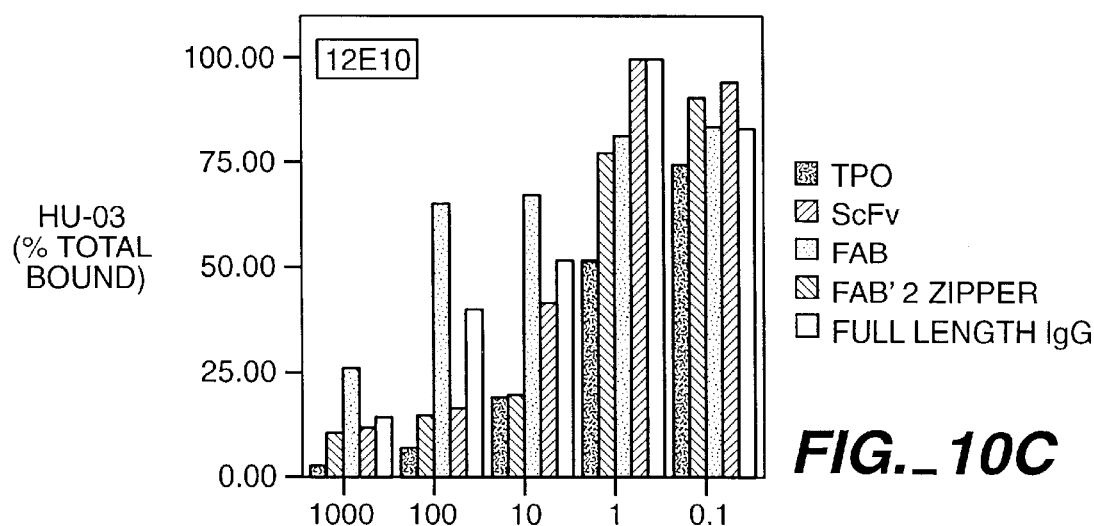
FIG._10C

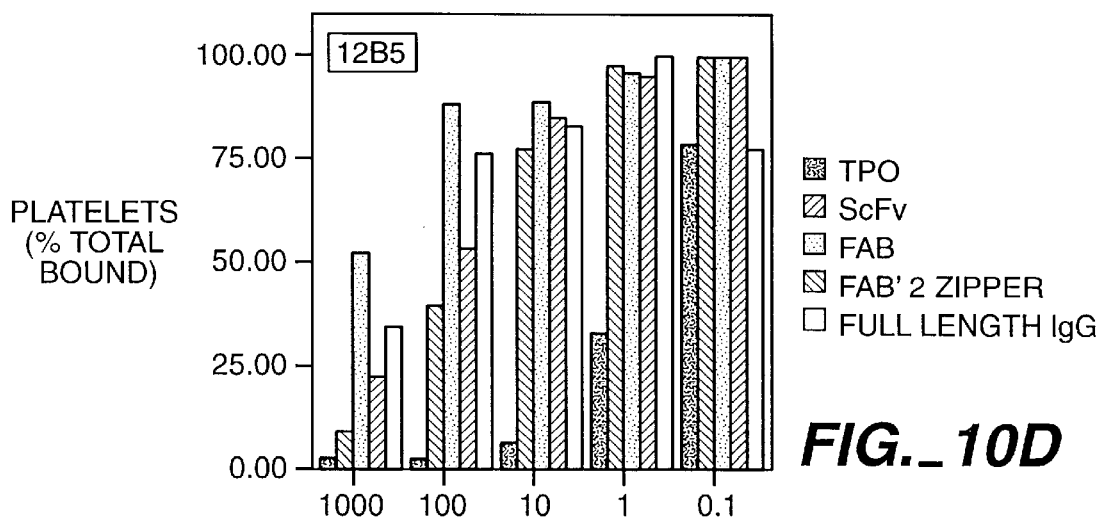
FIG._10D
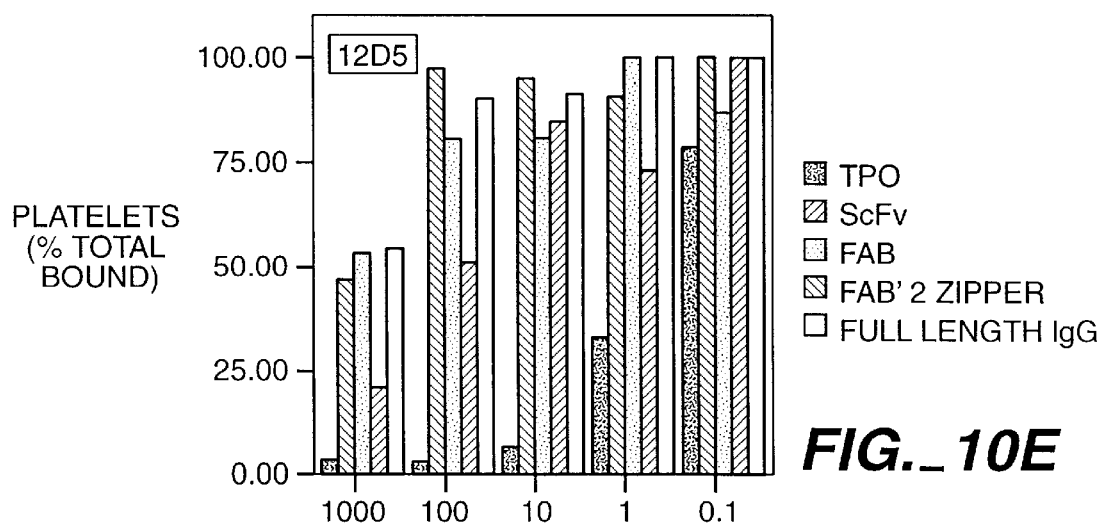
FIG._10E
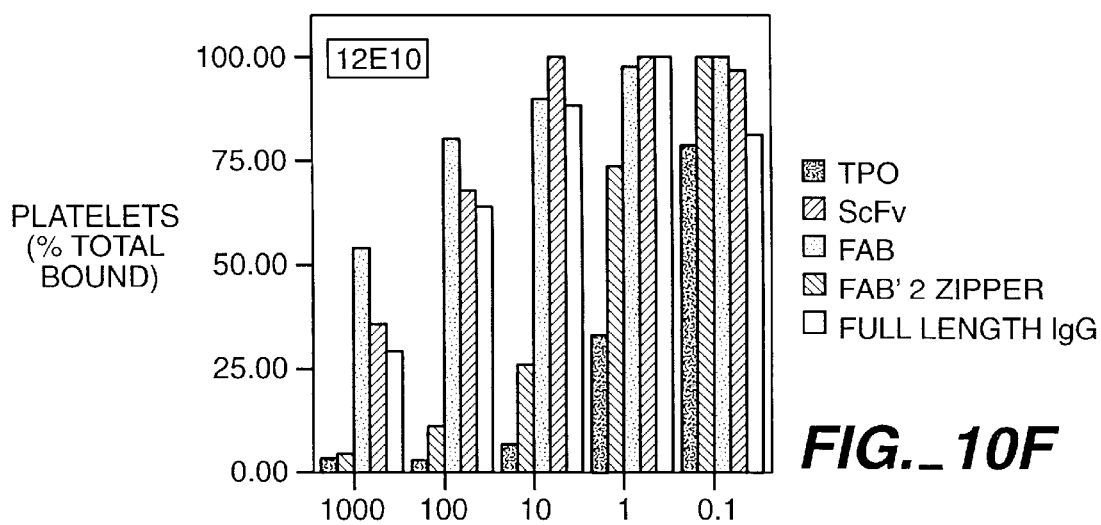
FIG._10F

AGONIST ANTIBODIES

FIELD OF THE INVENTION

This invention relates to the recombinant synthesis and purification of protein antibodies that influence survival, proliferation, differentiation or maturation of hematopoietic cells, especially platelet progenitor cells and to antibodies that influence the growth and differentiation of cells expressing a protein kinase receptor. This invention also relates to the cloning and expression of nucleic acids encoding antibody ligands (thrombopoietin receptor agonist antibodies) capable of binding to and activating a thrombopoietin receptor such as c-mpl, a member of the cytokine receptor superfamily. This invention further relates to the use of these antibodies alone or in combination with other cytokines to treat immune or hematopoietic disorders including thrombocytopenia and to uses in assays.

BACKGROUND OF THE INVENTION

In 1994 several groups reported the isolation and cloning of thrombopoietin (F. de Sauvage et al., Nature 369:533 (1994); S. Lok et al., Nature 369:565 (1994); T D. Bartley et al., Cell 77:1117 (1994); Y. Sohma et al., FEBS Letters 353:57 (1994); D J. Kuteret al., Proc. Natl. Acad. Sci. 91:11104 (1994)). This was the culmination of more than 30 years of research initiated in the late 50's when Yamamoto (S. Yamamoto, Acta Haematol Jpn. 20:163–178. (1957)) and Kelemen (E. Kelemen et al., Acta Haematol (Basel). 20:350–355 (1958)) proposed that physiological platelet production is controlled by a humoral factor termed "thrombopoietin" (TPO). Although routinely detected in urine, plasma and serum from thrombocytopenic animals and patients, as well as kidney cell conditioned media, purification of TPO proved to be a daunting task (for a review see MS. Gordon et al., Blood 80:302 (1992); W. Vainchenker et al., Critical Rev. Oncology/Hematology 20:165 (1995)). In the absence of purified TPO and the apparent fact that numerous plieotrophic cytokines affected megakaryocytopoiesis (M S. Gordon et al., Blood 80:302 (1992); W. Vainchenker et al., Critical Rev. Oncology/Hematology 20:165 (1995)), the existence of a lineage specific factor that regulated platelet production was doubted until the discovery of the orphan cytokine receptor c-Mpl in 1990 (M. Souyri et al., Cell 63:1137 (1990); I. Vigon et al., Proc. Natl Acad. Sci. 89:5640 (1992)). The expression of c-Mpl was found to be restricted to progenitor cells, megakaryocytes and platelets, and c-Mpl antisense oligonucleotides selectively inhibited in vitro megakaryocytopoiesis (M. Methia et al., Blood 82:1395 (1993)). From this it was postulated that c-Mpl played a critical role in regulating megakaryocytopoiesis and that its putative ligand may be the long sought TPO (M. Methia et al., supra). Following this discovery several groups utilizing c-Mpl ligand specific cell proliferation assays and c-Mpl as a purification tool isolated and cloned the ligand for c-Mpl (F. de Sauvage et al., supra; S. Lok et al., supra; T D. Bartley et al., supra). In addition two other groups independently reported the purification of the Mpl-ligand using standard chromatography techniques and megakaryocyte assays (Y. Sohma et al., supra; D J. Kuteret al., supra). In the years since its reported discovery numerous studies clearly indicate that the Mpl-ligand possess all the characteristics that have long been attributed to the purported regulator of megakaryocytopoiesis and thrombopoiesis and consequently, is now referred to as TPO. The Mpl ligand is currently referred to as either TPO or as megakaryocyte growth and differentiation factor (MGDF).

Human TPO consists of 332 amino acids that can be divided into 2 domains; an amino terminal domain of 153 amino acids showing 23% identity (50% similarity) to erythropoietin (EPO) and a unique 181 amino acid C-terminal domain that is highly glycosylated ((F. de Sauvage et al., supra; S. Lok et al., supra; T D. Bartley et al., supra). The EPO-like domain of TPO contains 4 cysteines, 3 of which are conserved with EPO. The first and last and the two middle cysteines form two disulfide bridges, respectively, which are both required for activity (T. Kato et al., Blood 86 (suppl 1):365 (1995)). None of the Asn-linked glycosylation sites present in EPO are conserved in the EPO-like domain of TPO, however, the EPO-like domain of recombinant TPO (rTPO) contains 2–3 O-linked glycosylations (M. Eng et al., Protein Science 5(suppl 1): 105 (1996)). A recombinant truncated form of TPO (rTPO153), consisting of only the EPO-like domain, is fully functional in vitro, indicating that this domain contains all the required structural elements to bind and activate Mpl (F. de Sauvage et al., supra; D L. Eaton et al., Blood 84(suppl 1):241 (1994)). The carboxy terminal domain of TPO contains 6 N-linked and 18 O-linked glycosylate sites and is rich in proline, serine and threonine (M. Eng et al., supra). The function of this domain remains to be elucidated. However, because of its high degree of glycosylation this region may act to stabilize and increase the half life of circulating TPO. This is supported by the observation that rTPO153 has a half life of 1.5 hours compared to 18–24 hours for full length glycosylated rTPO (GR. Thomas et al., Stem Cells 14(suppl 1) (1996).

The two domains of TPO are separated by a potential dibasic proteolytic cleavage site that is conserved among the various species examined. Processing at this site could be responsible for releasing the C-terminal region from the EPO domain in vivo. The physiological relevance of this potential cleavage site is unclear at this time. Whether TPO circulates as an intact full length molecule or as a truncated form is also equivocal. When aplastic porcine plasma was subjected to gel filtration chromatography, TPO activity present in this plasma resolved with a Mr. of ~150,000 ((F. de Sauvage et al., supra). Purified full length rTPO also resolves at this Mr., whereas the truncated forms resolve with Mr. ranging from 18,000–30,000. Using TPO ELISAs that selectively detect either full length or truncated TPO it has also been shown that full length TPO is the predominant form in the plasma of marrow transplant patients (Y G. Meng et al., Blood 86(suppl. 1):313 (1995)).

Prior to the discovery of c-Mpl and the isolation of TPO, it was thought that megakaryocytopoiesis was regulated at multiple cellular levels (M S. Gordon et al., supra; W. Vainchenker et al., supra; Y G. Meng et al., supra). This hypothesis was based on the observation that certain hematopoietic growth factors stimulated proliferation of megakaryocyte progenitors while others primarily affected maturation (M S. Gordon et al., supra; W. Vainchenker et al., supra; Y. G. Meng et al., supra). Other data indicated that plasma from thrombocytopenic animals contained distinct activities that either affected proliferation (meg-CSF) or maturation (TPO) of megakaryocytes (R J. Hill et al., Exp.Hematol 20:354 (1992)). Wendling and her colleagues (F. Wendling et al., Nature 369:571 (1994)) initially dispelled this theory by demonstrating that all the megakaryocyte colony-stimulating and thrombopoietic activities in thrombocytopenic plasma could be neutralized by soluble Mpl. This indicated that these activities are due to a single factor, the Mpl-ligand. Numerous studies have now shown that recombinant forms of TPO not only induce proliferation of progenitor megakaryocytes but also their maturation (K.

Kaushansky et al., *Nature* 369:568 (1994); F C. Zeigler et al., *Blood* 84:4045 (1994); V C. Broudy et al., *Blood* 85:1719 (1995); J L. Nichol et al., *J. Clin. Invest.* 95:2973 (1995); N. Banu et al., *Blood* 86:1331 (1995); N. Debili et al., *Blood* 86:2516 (1995); P. Angchaisuksiri et al., *Br. J. Haematol.* 93:13 (1996); E S. Choi et al., *Blood* 85:402 (1995)). Human CD34+, CD34+CD41+cells (F C. Zeigler et al., supra; V C. Broudy et al., supra; J L. Nichol et al., supra; N. Banu et al., supra;) or purified murine stem cells (sca+, lin-, kit+) (K. Kaushansky et al., supra; F C. Zeigler et al., supra) cultured with rTPO selectively differentiate to megakaryocytes. rTPO induces the differentiation and proliferation of megakaryocyte colonies in semisolid cultures and single megakaryocytes in liquid suspension cultures. This activity appears to be a direct effect of TPO as limiting dilution experiments show a direct correlation between progenitors seeded and megakaryocytes obtained (N. Debili et al., supra). In addition comparable results are obtained in serum free or serum containing culture conditions (N. Banu et al., supra; N. Debili et al., supra; P. Angchaisuksiri et al., supra;). These observations indicate that neither accessory cells or serum components are required for TPO to induce megakaryocyte growth and differentiation in vitro.

The effect of rTPO on the megakaryocyte maturation process is dramatic. rTPO induces highly purified murine or human progenitor cells in liquid culture to differentiate into very large mature polyploid megakaryocytes (F C. Zeigler et al., supra; V C. Broudy et al., supra; J L. Nichol et al., supra; N. Debili et al., supra). Megakaryocytes from such cultures exhibit ploidy of 4N-16N with ploidy classes of 64N and128N also being detected in these cultures (N. Debili et al., supra). In addition, megakaryocytes produced from these cultures undergo a terminal maturation process and appear to develop proplatelets and shed platelet like structures into the medium (F C. Zeigler et al., supra; N. Debili et al., supra; E S. Choi et al., supra). Significantly, the platelets produced from such cultures have been shown to be morphologically and functionally indistinct from plasma-derived platelets (E S. Choi et al., supra).

Although, rTPO appears to act directly on hematopoietic progenitors to induce megakaryocyte differentiation, it also acts synergistically and additively with early and late acting hematopoietic factors. In murine megakaryocytopoiesis assays IL-11, kit ligand (KL) or EPO act synergistically and IL-3 and IL-6 act additively with rTPO to stimulate proliferation of megakaryocyte progenitors (V C. Broudy et al., supra). In human megakaryocytopoiesis assays IL-3 and IL-6 effects are additive to rTPO, while KL acts synergistically with rTPO (J L. Nichol et al., supra; N. Banu et al., supra; N. Debili et al., supra; P. Angchaisuksiri et al., supra). None of the cytokines mentioned above affect the megakaryocyte maturational activity of rTPO.

The initial studies with rTPO clearly indicate that TPO predominantly affects the megakaryocytic lineage. However, like all other hematopoietic regulators, TPO affects other hematopoietic lineages as well. In the presence of EPO, rTPO has been shown to enhance erythroid burst (BFU-E) formation in human CD34+ colony assays (M. Kobayashi et al., *Blood* 86:2494 (1995); T. Papayannopoulou et al., *Blood* 87:1833 (1996)). The burst promoting activity of rTPO is comparable to GM-CSF and KL and increases both the number and size of BFU-E colonies (M. Kobayashi et al., supra). In addition rTPO also stimulates CFU-E development, indicating that TPO acts on both early and late erythroid progenitors (M. Kobayashi et al., supra; T. Papayannopoulou et al., supra). In the absence of EPO, however, rTPO has no effect on erythropoiesis. An effect of rTPO on myeloid colony growth in normal hematopoietic cultures has not been demonstrated in vitro, however.

rTPO has a dramatic effect on platelet production when administered to normal animals. Pharmacological doses of recombinant forms of TPO cause as much as a 10 fold increase in platelet levels in mice and non-human primates (E F. Winton et al., *Exp. Hematol.* 23:879 (1995); A M. Farese et al., *Blood* 86:54 (1995); K H. Sprugel et al., *Blood* 86(suppl 1):20 (1995); L A. Harker et al., *Blood* 87:1833 (1996); K. Kaushansky et al., *Exp. Hematol.* 24:265 (1996); T R. Ulich et al., *Blood* 87:5006 (1996); K. Ault et al., *Blood* 86(suppl 1): 367 (1995); N C. Daw et al., *Blood* 86 (suppl 1):5006 (1995)). This effect of rTPO is due to an increase in the synthesis of new platelets as reticulated platelets increase within 24 hours after rTPO administration (K. Ault et al., supra). Preceding this effect is a dramatic increase in CFU-MK in both the marrow and spleen (A M. Farese et al., supra; K. Kaushansky et al., supra; T R. Ulich et al., supra). Megakaryocytes from rTPO treated animals exhibit a higher mean ploidy and are larger in size than megakaryocytes from control animals. These later two observations again demonstrate the proliferative and maturational activities of TPO on the megakaryocytic lineage. Because the effect of TPO on megakaryocytes precedes its effect on platelet production it has been suggested that TPO primarily affects megakaryocyte progenitors rather than inducing platelet release from mature megakaryocytes (N C. Daw et al., supra). No significant effect on red blood cell (RBC) or white blood cell (WBC) production occurs in normal animals following rTPO administration. However, rTPO treatment caused an expansion of BFU-E and CFU-GM and a redistribution CFU-E in normal mice (K. Kaushansky et al., supra) and expanded CFU-mixed in rhesus monkeys (A M. Farese et al., supra).

Even though rTPO dramatically stimulates platelet production, it only has a modest effect on platelet function. In vitro studies show that rTPO has no effect on platelet aggregation itself, but does enhance agonist induced aggregation (G. Montrucchio et al., *Blood* 87:2762 (1996); A. Oda et al., *Blood* 87:4664 (1996); C F. Toombs et al., *Thromb. Res.* 80:23 (1995); C F. Toombs et al., *Blood* 86(suppl 1):369 (1995)). rTPO appears to sensitize platelets making them moderately more responsive to aggregation agonist. This raises the possibility that rTPO may have prothrombotic effects in vivo. However, an increase in thrombotic episodes in animals treated with rTPO has never been observed, even when platelet levels were 4–10 fold above normal. In vivo thrombosis models also indicate that elevated platelet levels following rTPO treatment is not associated with an increase in platelet dependent thrombosis (L A. Harker et al., supra; C F. Toombs et al., supra). These results indicate that stimulation of platelet production by rTPO will unlikely be associated with an increase in thrombo-occulsive events.

The involvement of c-Mpl and TPO in the control of platelet production and its effect on other hematopoietic lineages is further demonstrated by the phenotype of mice deficient in either the c-mpl or the TPO genes (W S. Alexander et al., *Blood* 87:2162 (1996); F J. de Sauvage et al., *J. Exp.Med.* 183:651 (1996); A L. Gurney et al., *Science* 265:1445 (1994)). In both cases a dramatic 85 to 90% drop in platelet counts is observed with a similar decrease of megakaryocytes in the spleen and bone marrow. In addition, the megakaryocytes of the knockout mice are smaller and exhibit a lower ploidy than those of control mice. The similarity in phenotype observed for these knock-outs (KO) indicates that the system is non-redundant and that there is probably only one receptor for TPO and one ligand for c-Mpl. Although the platelet number is reduced in the KO mice their platelets appear normal, both structurally and functionally, and are sufficient to prevent overt bleeding. The genes and factors involved in the production of this basal level of platelets and megakaryocytes still remain to be identified. However, treatment of either the TPO or c-mpl knockout mice with other cytokines with megakaryopoietic activity (IL-6,IL-11 and stem cell factor) results in a modest stimulation of platelet production (A L. Gurney et al., supra). This suggest that these cytokines do not require TPO or c-mpl to exert their thrombopoietic activity and, therefore, may be involved in the maintenance of a basal level of megakaryocytes and platelets.

Comparison of CFU-megakaryocyte (CFU-Meg) from TPO or c-mpl deficient and normal mice shows that the number of megakaryocytes progenitors is decreased in both knock-outs compared to control, suggesting that TPO acts on very early megakaryocyte progenitors. In addition, both erythroid and myeloid progenitors are also reduced in the TPO and c-Mpl knockout mice (W S. Alexander et al., supra; K. Carver-Moore et al., 88:803 (1996)). This reduction in progenitors from all lineages indicates that TPO probably acts on a very early pluripotent progenitor cell. The involvement of TPO and c-Mpl at an early stage of hematopoiesis correlates with the detection of c-Mpl expression in AA4+ Sca+ murine stem cell population (F C. Zeigler et al., supra). The effect of TPO on this most primitive stem cell population still remains to be investigated, however, preliminary data indicate that TPO may directly affect the proliferation of primitive murine hematopoietic stem or progenitor cells (E. Stinicka et al., *Blood* 87:4998 (1996); M. Kobayashi et al., *Blood* 88:429 (1996); H. Ku et al., *Blood* 87:4544 (1996)). This, in part, may explain the effect TPO has on erythropoiesis and myelopoiesis in vitro and in vivo.

It has long been observed that an inverse correlation exists between plasma megakaryopoietic and thrombopoietic activity and platelet levels (reviewed in T P. McDonald, *Am. J. Pediatr. Hematol./Oncol.* 14:8 (1992)). TPO specific ELISAs and cell proliferation assays have now confirmed that TPO levels increase and decrease inversely with platelet mass (J L. Nichol et al., supra; EVB. Emmons et al., *Blood* 87:4068 (1996); H. Oh et al., *Blood* 87:4918 (1996); M. Chang et al., *Blood* 86(suppl 1):368 (1995)). Unlike erythropoietin, however, TPO does not appear to be regulated at the transcriptional level, but rather by platelet mass. This was initially proposed de Gabriele and Pennington (G. de Gabriele et al., *Br. J. Haematol.* 13:202 (1967); G. de Gabriele et al., *Br. J. Haematol.* 13:210 (1967)) and subsequently confirmed by Kuter and Rosenberg (D J. Kuter et al., *Blood* 84:1464 (1994)) who showed direct regulation of circulating TPO levels by exogenously administering platelets to thrombocytopenic mice. More recently, it was demonstrated that TPO mRNA levels in thrombocytopenic mice are not increased even though TPO levels are elevated by at least 10 fold (P J. Fielder et al., *Blood* 87:2154 (1996); R. Stoffel et al., *Blood* 87:567 (1996)). In addition, the gene dosage effect observed in TPO heterozygous knockout mice refute the regulation of TPO production by platelet mass (F J. de Sauvage et al., supra). Taken together, these results strongly support the hypothesis that TPO expression is constitutive and it is the sequestering by platelets that regulates TPO levels. Platelets bind TPO with high affinity (Kd(100–400 pM) and internalize and degrade TPO (P J. Fielder et al., supra). Platelets from c-Mpl knockout mice do not bind TPO and the clearance of TPO by these mice is 5 fold slower than that observed for wild type mice (P J. Fielder et al., supra). These results indicate that TPO clearance is mediated by platelet binding via c-Mpl. It is also likely that megakaryocyte mass plays a role in regulating circulating TPO levels. This is supported by the observation that both ITP patients and mice deficient in the NF-E2 transcription factor are highly thrombocytopenic, exhibit megakaryocytosis, but have normal TPO levels (EVB. Emmons et al., supra; R A. Shivdasani et al., *Cell* 81:695 (1995)). In situ studies with radiolabeled TPO show that marrow megakaryocytes of the NF-E2 mice bind significant amounts of labeled TPO (R A. Shivdasani et al., *Blood submitted* (1996)). The phenotype of the ITP and NF-E2 knockout mice, therefore, suggest that binding of TPO to megakaryocytes may also regulate TPO levels.

The dramatic effect of rTPO on platelet production in normal mice and monkeys and subsequent clinical trials indicate that rTPO is clinically useful in alleviating thrombocytopenia associated with myelosuppressive and myeloablative therapies for cancer patients. In several myelosuppressive and myeloablative murine and monkey preclinical models recombinant forms of TPO have been shown to significantly affect platelet recovery. In mice treated with carboplatin and sublethal irradiation in combination (J P Leonard et al., *Blood* 83:1499 (1994)), daily treatment with rTPO both reduced the severity of the platelet nadir and accelerated platelet recovery by 10–12 days when compared to excipient treated animals (G R. Thomas et al., supra; K. Kaushansky et al., supra; M M. Hokom et al., *Blood* 86:4486 (1995)). Similar results were obtained in a murine sublethal irradiation model (G R. Thomas et al., supra). In murine myeloablative transplantation models rTPO has been shown to reduce the extent of the nadir and accelerate platelet recovery by 2–3 weeks (G R. Thomas et al., supra; K. Kabaya et al., *Blood* 86(suppl 1):114 (1995); G. Molineux et al., *Blood* 86(suppl 1):227 (1995)). Treatment of sublethally irradiated rhesus monkeys with rTPO accelerated platelet recovery by 3 weeks and prevented platelet nadirs below 40,000 (A M. Farese et al., *J. Clin. Invest.* 97:2145 (1996); K J. Neelis et al., *Blood* 86(suppl 1):256 (1995)). Even more impressively, rTPO completely prevented post-chemotherapy thrombocytopenia following the treatment of rhesus monkeys with hepsulfam (A M. Farese et al., supra). In contrast to these promising results, two groups have reported that rTPO had no effect on the hematopoietic recovery of lethally irradiated mice or monkeys rescued with a marrow transplant (K J. Neelis et al., supra; W E. Fibbe et al., *Blood* 86:3308 (1995)). The reason for this discrepancy is unclear, however it is possible that lethal radiation may destroy stromal cells or components essential for TPO activity in vivo. In support of this, lethally irradiated mice transplanted with marrow cells from rTPO treated donor mice show accelerated recovery of platelets and RBCs, however, post-transplant administration of rTPO had no further effect on this accelerated recovery (W E. Fibbe et al., supra). This result suggests that although the transplanted cell population was enriched for megakaryocyte progenitors, TPO had no effect on these progenitors in a lethally irradiated marrow.

Although rTPO only modestly affects erythroid and myeloid lineages in normal mice it dramatically accelerates the recovery of all progenitor classes in myelosuppressed mice and monkeys resulting in a significant acceleration of RBC and WBC recovery (K. Kaushansky et al., supra; A M. Farese et al., supra; K. Kaushansky et al., *J. Clin. Invest.* 96:1683 (1995)). The effect of rTPO on neutrophil recovery has been shown to be additive to that of G-CSF (A M. Farese et al., supra). These results indicate that the clinical utility of rTPO may be broader than originally anticipated.

The difference between the effect of rTPO on hematopoiesis in normal and myelosuppressed animals is likely due to the change in the cytokine environment that occurs following myelosuppressive therapy. It is likely that elevated levels of EPO, G-CSF or other cytokines essential for erythropoiesis and myelopoiesis present following myelosuppressive treatment interact with rTPO to have a multilineage effect (K. Kaushansky et al., supra). In normal mice the level of these cytokines are insufficient and the effects of rTPO on erythroid and myeloid lineages are less significant. This hypothesis is supported by the above mentioned synergistic interaction of rTPO and EPO to stimulate in vitro erythropoiesis (E S. Choi et al., supra). It has also been proposed that production of hemopoietic factors from megakaryocytes themselves may also play a role in the multilineage effect of rTPO (A M. Farese et al., supra).

In the above mentioned animal studies rTPO was administered daily for 14–28 days, which was based on previous experience in dosing other hematopoietic growth factors. However, it has recently been shown that a single dose of rTPO following myelosuppressive treatment of mice with carboplatin and sublethal irradiation is as effective as multiple doses in reducing nadirs and accelerating platelet and RBC recovery (G R. Thomas et al., supra). This effect is likely due to the potency and long half life of rTPO.

(G R. Thomas et al., supra). This is supported by the fact that single doses of unglycosylated rTPO153 are not effective in this model. These observations indicate that the frequency of rTPO dosing required to affect hematopoietic recovery following myelosuppressive treatment may be significantly less than that for other currently used cytokines.

Early results from human clinical trails show that rTPO also stimulates platelet production in humans. In phase I trials, a pegylated and truncated form of rTPO (MGDF) administered daily for 10 days at 0.03–5.0 $\mu$g/kg to cancer patients prior to chemotherapy caused up to a four fold increase in circulating platelet levels (R. Basser et al., *Blood* 86(suppl 1):257 (1995); J E J. Rasko et al., *Blood* 86(suppl 1):497 (1995)). Similarly, patients given a single dose of rTPO had platelet levels increase by four fold (S. Vaden-Raj et al., Stimulation of megakaryocyte and platelet production by a single dose of recombinant human thrombopoietin in cancer patients. Submitted. (1996)). In both studies platelet increases are observed by day four and peak about 12–16 days later. No drug related toxicity's were reported and, although platelet levels greater then 1×106/$\mu$l were observed in some of the patients, no thrombotic events were observed. This indicates that TPO will be well tolerated in humans. In myelosuppressed patients, pegylated rTPO153(MGDF) given post chemotherapy has been shown to reduce the extent of the platelet nadir following chemotherapy (G. Begley et al., *Proceedings of ASCO* 15:271 (1996); M. Fanucchi et al., *Proceedings of ASCO* 15:271 (1996)). As seen in the preclinical animals studies, TPO also expanded marrow progenitors of megakaryocyte, erythroid, myeloid and multipotential lineages (S. Vaden-Raj et al., supra). This later observation suggests that rTPO may be useful as a priming agent.

It is believed that the proliferation and maturation of hematopoietic cells is tightly regulated by factors that positively or negatively modulate pluripotential stem cell proliferation and multilineage differentiation. These effects are mediated through the high-affinity binding of extracellular protein factors (ligands) to specific cell surface receptors. These cell surface receptors share considerable homology and are generally classified as members of the cytokine receptor superfamily. Members of the superfamily include receptors for: IL-2 (b and g chains) (Hatakeyama et al., *Science*, 244:551–556 (1989); Takeshita et al., *Science*, 257:379–382 (1991)), IL-3 (Itoh et al., *Science*, 247:324–328 (1990); Gorman et al., *Proc. Natl. Acad. Sci. USA*, 87:5459–5463 (1990); Kitamura et al., *Cell*, 66:1165–1174 (1991a); Kitamura et al., *Proc. Natl. Acad. Sci. USA*, 88:5082–5086 (1991b)), IL-4 (Mosley et at., *Cell*, 59:335–348 (1989), IL-5 (Takaki et al., *EMBO J.*, 9:4367–4374 (1990); Tavernier et al., *Cell*, 66:1174–1184 (1991)), IL-6 (Yamasaki et al., *Science*, 241:825–828 (1988); Hibi et al., *Cell*, 63:1149–1157 (1990), IL-7 (Goodwin et at, *Cell*, 60:941–951 (1990)), IL-9 (Renault et al., *Proc. Natl. Acad. Sci. USA*, 89:5690–5694 (1992), granulocyte-macrophage colony-stimulating factor (GM-CSF) (Gearing et al., *EMBO J.*, 8:3667–3676 (1991); Hayashida et at., *Proc. Natl. Acad. Sci. USA*, 244:9655–9659 (1990)), granulocyte colony-stimulating factor (G-CSF) (Fukunaga et al., *Cell*, 61:341–350 (1990a); Fukunaga et al., *Proc. Natl. Acad Sci. USA*, 87:8702–8706 (1990b); Larsen et al., *J. Exp. Med.*, 172:1559–1570 (1990)), EPO (D'Andrea et al., *Cell*, 57:277–285 (1989); Jones et al., *Blood*, 76:31–35 (1990)), Leukemia inhibitory factor (LIF) (Gearing et al., *EMBO J.*, 10:2839–2848 (1991)), oncostatin M (OSM) (Rose et al., *Proc. Natl. Acad Sci. USA*, 88:8641–8645 (1991)) and also receptors for prolactin (Boutin et al., *Proc. Natl. Acad. Sci. USA*, 88:7744–7748 (1988); Edery et al., *Proc. Natl. Acad. Sci. USA*, 86:2112–2116 (1989)), growth hormone (GH) (Leung et at, *Nature*, 330:537–543 (1987)) and ciliary neurotrophic factor (CNTF) (Davis et al., *Science*, 253:59–63 (1991).

Members of the cytokine receptor superfamily may be grouped into three functional categories (for review see Nicola et al., *Cell*, 67:1–4 (1991)). The first class comprises single chain receptors, such as erythropoietin receptor (EPO-R) or granulocyte colony stimulating factor receptor (G-CSF-R), which bind ligand with high affinity via the extracellular domain and also generate an intracellular signal. A second class of receptors, so called a-subunits, includes interleukin-6 receptor (IL6-R), granulocyte-macrophage colony stimulating factor receptor (GM-CSF-R), interleukin-3 receptor (IL3-Ra) and other members of the cytokine receptor superfamily. These a-subunits bind ligand with low affinity but cannot transduce an intracellular signal. A high affinity receptor capable of signaling is generated by a heterodimer between an a-subunit and a member of a third class of cytokine receptors, termed b-subunits, e.g., $b_c$, the common b-subunit for the three a-subunits of IL-3-R, IL-5-R and GM-CSF-R (Nicola N. A. et. al. *Cell* 67:1–4 (1991)).

Evidence that mpl is a member of the cytokine receptor superfamily comes from sequence homology (Gearing, *EMBO J.*, 8:3667–3676 (1988); Bazan, *Proc. Natl. Acad. Sci. USA*, 87:6834–6938 (1990); Davis et al., *Science*, 253:59–63 (1991) and Vigon et al., *Proc. Natl. Acad. Sci. USA*, 89:5640–5644 (1992)) and its ability to transdu proliferative signals.

Deduced protein sequence from molecular cloning of murine c-mpl reveals this protein is homologous to other cytokine receptors. The extracellular domain contains 465 amino acid residues and is composed of two subdomains each with four highly conserved cysteines and a particular motif in the N-terminal subdomain and in the C-terminal subdomain. The ligand-binding extracellular domains are predicted to have similar double b-barrel fold structural geometries. This duplicated extracellular domain is highly homologous to the signal transducing chain common to IL-3, IL-5 and GM-CSF receptors as well as the low-affinity binding domain of LIF (Vigon et al., *Oncogene*, 8:2607–2615 (1993)). Thus mpl may belong to the low affinity ligand binding class of cytokine receptors.

A comparison of murine mpl and mature human mpl P, reveals these two proteins show 81% sequence identity. More specifically, the N-terminus and C-terminus extracellular subdomains share 75% and 80% sequence identity respectively. The most conserved mpl region is the cytoplasmic domain showing 91% amino acid identity, with a sequence of 37 residues near the transmembrane domain being identical in both species. Accordingly, mpl is reported to be one of the most conserved members of the cytokine receptor superfamily (Vigon supra).

Activation of certain hematopoietic receptors is believed to cause one or more effects including; stimulation of proliferation, stimulation of differentiation, stimulation of growth and inhibition of apoptosis (Libol et al *Proc. Natl. Acad. Sci.* 248:378 (1993). Activation of hematopoietic receptors upon ligand binding may be due to dimerization of two or more copies of the receptor. In addition to the naturally occurring ligand causing this dimerization, agonist antibodies may also activate receptors by crosslinking or otherwise causing dimerization of a receptor. Such antibodies are useful for the same indications as the natural ligand and may have advantageous properties such as a longer half-life. An example of a monoclonal antibody to a cytokine receptor that activates the erythropoietin receptor (EPO-R) is described in WO 96/03438 (published Feb. 8, 1996). These agonist antibodies to EPO-R are about 3–4 orders of magnitude weaker in activity based on weight than the natural EPO ligand.

There is a current and continuing need to isolate and identify molecules, especially antibodies, fragments and derivatives thereof, capable of stimulating proliferation, differentiation and maturation and/or modulation of apoptosis of cells, for example hematopoietic cells, including megakaryocytes or their predecessors for therapeutic use in the treatment of hematopoietic disorders including thrombocytopenia.

SUMMARY OF THE INVENTION

Accordingly, It is an object of this invention to obtain a pharmaceutically or essentially pure antibody or fragments or derivatives thereof capable of stimulating proliferation, differentiation and/or maturation of hematopoietic cells, including megakaryocytes or their predecessors, or to modulate apoptosis of hematopoietic cells.

It is a specific object of the present invention to isolate antibody ligands capable of binding in vivo a hematopoietic growth factor superfamily receptor and to activate the receptor, the antibody having a biological activity equal to or not less than 2 orders of magnitude below that of the naturally occurring ligand on a weight basis.

It is also an object of the present invention to isolate antibody ligands capable of binding to and activating any of the three functional categories of cytokine superfamily receptors (see Nicola et al., *Cell*, 67:1–4 (1991)).

In one embodiment, the objects of the invention are achieved by providing an antibody or fragment thereof that activates a hematopoietic growth factor superfamily receptor having a biological activity within 2 orders of magnitude (100), preferably within one order of magnitude (10), of the natural ligand on a weight basis. Preferably, the antibody activates the thrombopoietin (TPO) receptor. This antibody, referred to as an agonist antibody, activates a thrombopoietin receptor which preferably comprises a mammalian c-mpl, more preferably human c-mpl. Usually the antibody will be a full length antibody such as an IgG antibody. Suitable representative fragment agonist antibodies include Fv, ScFv, Fab, F(ab')$_2$ fragments, as well as diabodies and linear antibodies. These fragments may be fused to other sequences including, for example, the F" or Fc region of an antibody, a "leucine zipper" or other sequences including pegylated sequences or Fc mutants used to improve or modulate half-life. Normally the antibody is a human antibody and may be a non-naturally occurring antibody, including affinity matured antibodies. Representative antibodies that activate c-mpl are selected from the group 12E10, 12B5, 1OF6 and 12D5, and affinity matured derivatives thereof. Other preferred agonist antibodies to c-mpl are selected from the group consisting of Ab1, Ab2, Ab3, Ab4, Ab5 and Ab6, wherein each Ab1–Ab6 contains a VH and VL chain and each VH and VL chain contains complementarity determining region (CDR) amino acid sequences designated CDR1, CDR2 and CDR3 separated by framework amino acid sequences, the amino acid sequence of each CDR in each VH and VL chain of Abl-Ab6 is shown in Table I.

TABLE I

| Ab1: | VH$^{CDR1}$ | VH$^{CDR2}$ | VH$^{CDR3}$ |
|---|---|---|---|
| DNA | (SEQ ID NO: 1) | (SEQ ID NO: 3) | (SEQ ID NO: 5) |
| protein | (SEQ ID NO: 2) | (SEQ ID NO: 4) | (SEQ ID NO: 6) |
| | VL$^{CDR1}$ | VL$^{CDR2}$ | VL$^{CDR3}$ |
| DNA | (SEQ ID NO: 7) | (SEQ ID NO: 9) | (SEQ ID NO: 11) |
| protein | (SEQ ID NO: 8) | (SEQ ID NO: 10) | (SEQ ID NO: 12) |
| Ab2: | VH$^{CDR1}$ | VH$^{CDR2}$ | VH$^{CDR3}$ |
| DNA | (SEQ ID NO: 13) | (SEQ ID NO: 15) | (SEQ ID NO: 17) |
| protein | (SEQ ID NO: 14) | (SEQ ID NO: 16) | (SEQ ID NO: 18) |
| | VL$^{CDR1}$ | VL$^{CDR2}$ | VL$^{CDR3}$ |
| DNA | (SEQ ID NO: 19) | (SEQ ID NO: 21) | (SEQ ID NO: 23) |
| protein | (SEQ ID NO: 20) | (SEQ ID NO: 22) | (SEQ ID NO: 24) |
| Ab3: | VH$^{CDR1}$ | VH$^{CDR2}$ | VH$^{CDR3}$ |
| DNA | (SEQ ID NO: 25) | (SEQ ID NO: 27) | (SEQ ID NO: 29) |
| protein | (SEQ ID NO: 26) | (SEQ ID NO: 28) | (SEQ ID NO: 30) |
| | VL$^{CDR1}$ | VL$^{CDR2}$ | VL$^{CDR3}$ |
| DNA | (SEQ ID NO: 19) | (SEQ ID NO: 21) | (SEQ ID NO: 23) |
| protein | (SEQ ID NO: 20) | (SEQ ID NO: 22) | (SEQ ID NO: 24) |
| Ab4: | VH$^{CDR1}$ | VH$^{CDR2}$ | VH$^{CDR3}$ |
| DNA | (SEQ ID NO: 25) | (SEQ ID NO: 31) | (SEQ ID NO: 33) |
| protein | (SEQ ID NO: 26) | (SEQ ID NO: 32) | (SEQ ID NO: 34) |
| | VL$^{CDR1}$ | VL$^{CDR2}$ | VL$^{CDR3}$ |
| DNA | (SEQ ID NO: 35) | (SEQ ID NO: 21) | (SEQ ID NO: 23) |
| protein | (SEQ ID NO: 20) | (SEQ ID NO: 22) | (SEQ ID NO: 24) |
| Ab5: | VH$^{CDR1}$ | VH$^{CDR2}$ | VH$^{CDR3}$ |
| DNA | (SEQ ID NO: 36) | (SEQ ID NO: 38) | (SEQ ID NO: 40) |
| protein | (SEQ ID NO: 37) | (SEQ ID NO: 39) | (SEQ ID NO: 41) |
| | VL$^{CDR1}$ | VL$^{CDR2}$ | VL$^{CDR3}$ |
| DNA | (SEQ ID NO: 19) | (SEQ ID NO: 21) | (SEQ ID NO: 23) |
| protein | (SEQ ID NO: 20) | (SEQ ID NO: 22) | (SEQ ID NO: 24) |
| Ab6: | VH$^{CDR1}$ | VH$^{CDR2}$ | VH$^{CDR3}$ |
| DNA | (SEQ ID NO: 42) | (SEQ ID NO: 44) | (SEQ ID NO: 46) |
| protein | (SEQ ID NO: 43) | (SEQ ID NO: 45) | (SEQ ID NO: 47) |
| | VL$^{CDR1}$ | VL$^{CDR2}$ | VL$^{CDR3}$ |
| DNA | (SEQ ID NO: 48) | (SEQ ID NO: 50) | (SEQ ID NO: 52) |
| protein | (SEQ ID NO: 49) | (SEQ ID NO: 51) | (SEQ ID NO: 53) |

Other preferred c-mpl agonist antibodies of this invention include those that activate platelets in a manner similar to TPO or in a manner similar to ADP, collagen and the like. Optionally the c-mpl agonist antibodies of this invention do not activate platelets. The c-mpl agonist antibodies of this invention are used in a manner similar to TPO.

In another embodiment, substantially pure single chain antibodies are provided which bind to and act as agonist or antagonist antibodies to a cytokine receptor or to a kinase receptor.

The invention also provides a method of obtaining these antibodies, in particular a method of screening a library of phage displayed antibodies, preferably human single chain antibodies.

BRIEF DESCRIPTION OF THE DRAWINGS

FIG. 1 shows examples of single chain antibody (scFv) fragments denominated 10F6, 5E5, 10D10, 12B5, 12D5 and 12E10 having sequences for CDRs and framework regions (SEQ ID NOS: 74–79).

FIG. 2 illustrates a method for the construction of a phage library containing single-chain antibodies fused to a coat protein of a phage.

FIG. 3 shows a single-chain antibody displayed as a fusion protein on coat protein 3 of a filamentous phage.

FIG. 4 illustrates a method of selecting scFv in a phage library by one or more binding selection cycles.

FIG. 5 illustrates a method of panning high affinity phage using biotinylated antigen and streptavidin coated paramagnetic beads.

FIG. 6 shows a process for identifying c-mpl binding phage using a phage ELISA method.

FIG. 7 illustrates DNA fingerprinting of clones to determine diversity by BstNI restriction enzyme analysis.

FIG. 8 shows a typical BstNI analysis on a 3% agarose gel; see Example 2.

FIG. 9 shows the results of agonist antibodies relative to TPO in the KIRA-ELISA assay.

FIG. 10 shows the results of TPO-antibody competitive binding assays for HU-03 cells. See Example 1.

FIG. 11 shows activity for MuSK agonist antibodies of Example 9.

DETAILED DESCRIPTION OF THE PREFERRED EMBODIMENTS

I. Definitions

In general, the following words or phrases have the indicated definition when used in the description, examples, and claims.

The terms "agonist" and "agonistic" when used herein refer to or describe a molecule which is capable of, directly or indirectly, substantially inducing, promoting or enhancing cytokine biological activity or cytokine receptor activation.

"Agonist antibodies" (aAb) are antibodies or fragments thereof that possess the property of binding to a cytokine superfamily receptor and causing the receptor to transduce a survival, proliferation, maturation and/or differentiation signal. Included within the definition of transducing a survival signal is a signal which modulates cell survival or death by apoptosis. To be therapeutically useful the agonist antibodies of this invention will be capable of inducing or causing survival, proliferation, maturation or differentiation at a concentration equal to or not less than 2 orders of magnitude (100-fold) below that of the natural in vivo ligand on a weight basis.

"Activate a receptor", as used herein, is used interchangeably with transduce a growth, survival, proliferation, maturation and/or differentiation signal.

"Activate platelets", as used herein, means to stimulate platelets to make them more likely to aggregate by comparison to unactivated platelets. For example, ADP and collagen are substances known to activate platelets.

"Affinity matured antibodies" are antibodies that have had their binding affinity and/or biological activity increased by altering the type or location of one or more residues in the variable region. An example of alteration is a mutation which may be in either a CDR or a framework region. An affinity matured antibody will typically have its binding affinity increased above that of the isolated or natural antibody or fragment thereof by from 2 to 500 fold. Preferred affinity matured antibodies will have nanomolar or even picomolar affinities to the receptor antigen. Affinity matured antibodies are produced by procedures known in the art. Marks, J. D. et al. *Bio/Technology* 10:779–783 (1992) describes affinity maturation by VH and VL domain shuffling. Random mutagenesis of CDR and/or framework residues is described by; Barbas, C. F. et al. *Proc Nat. Acad. Sci, USA* 91:3809–3813 (1994), Schier, R. et al. *Gene* 169:147–155 (1995), Yelton, D. E. et al. *J. Immunol.* 155:1994–2004 (1995), Jackson, J. R. et al. *J. Immunol.* 154(7):3310–9 (1995), and Hawkins, R. E. et al, *J. Mol. Biol.* 226:889–896 (1992

"Cytokine" is a generic term for proteins released by one cell population which act on another cell as intercellular mediators. Examples of such cytokines are lymphokines, monokines, and traditional polypeptide hormones. Included among the cytokines are growth hormone, insulin-like growth factors, human growth hormone, N-methionyl human growth hormone, bovine growth hormone, parathyroid hormone, thyroxine, insulin, proinsulin, relaxin, prorelaxin, glycoprotein hormones such as follicle stimulating hormone (FSH), thyroid stimulating hormone (TSH), and leutinizing hormone (LH), hematopoietic growth factor, hepatic growth factor, fibroblast growth factor, prolactin, placental lactogen, tumor necrosis factor-a (TNF-a and TNF-b) mullerian-inhibiting substance, mouse gonadotropin-associated peptide, inhibin, activin, vascular endothelial growth factor, integrin, nerve growth factors such as NGF-b, platelet-growth factor, transforming growth factors (TGFs) such as TGF-a and TGF-b, insulin-like growth factor-I and -II, erythropoietin (EPO), osteoinductive factors, interferons such as interferon-a, -b, and -g, colony stimulating factors (CSFs) such as macrophage-CSF (M-CSF), granulocyte-macrophage-CSF (GM-CSF), and granulocyte-CSF (G-CSF), thrombopoietin (TPO), interleukins (IL's) such as IL-1, IL-1a, IL-2, IL-3, IL-4, IL-5, IL-6, IL-7, IL-8, IL-9, IL-11, IL-12 and other polypeptide factors including LIF, SCF, and kit-ligand. As used herein the foregoing terms are meant to include proteins from natural sources or from recombinant cell culture. Similarly, the terms are intended to include biologically active equivalents; e.g., differing in amino acid sequence by one or more amino acids or in type or extent of glycosylation.

"Cytokine superfamily receptors" and "hematopoietic growth factor superfamily receptors" are used interchangeably herein and are a group of closely related glycoprotein cell surface receptors that share considerable homology including frequently a WSXWS domain and are generally classified as members of the cytokine receptor superfamily (see e.g. Nicola et al., *Cell,* 67:1–4 (1991) and Skoda, R. C. et al. *EMBO J.* 12:2645–2653 (1993)) Generally, these receptors are interleukins (IL) or colony-stimulating factors (CSF). Members of the superfamily include, but are not limited to, receptors for: IL-2 (b and g chains) (Hatakeyama et al., *Science,* 244:551–556 (1989); Takeshita et al., *Science,* 257:379–382 (1991)), IL-3 (Itoh et al., Science, 247:324–328 (1990); Gorman et al., *Proc. Natl. Acad. Sci.*

USA, 87:5459–5463 (1990); Kitamura et al., *Cell*, 66:1165–1174 (1991a); Kitamura et al., *Proc. Natl. Acad. Sci. USA*, 88:5082–5086 (1991b)), IL-4 (Mosley et al., *Cell*, 59:335–348 (1989), IL-5 (Takaki et al., *EMBO J.*, 9:4367–4374 (1990); Tavernier et al., *Cell*, 66:1175–1184 (1991)), IL-6 (Yamasaki et al., *Science*, 241:825–828 (1988); Hibi et al., *Cell*, 63:1149–1157 (1990)), IL-7 (Goodwin et al., *Cell*, 60:941–951 (1990)), IL-9 (Renault et al, *Proc. Natl. Acad. Sci. USA*, 89:5690–5694 (1992)), granulocyte-macrophage colony-stimulating factor (GM-CSF) (Gearing et al., *EMBO J.*, 8:3667–3676 (1991); Hayashida et al., *Proc. Natl. Acad. Sci. USA*, 244:9655–9659 (1990)), granulocyte colony-stimulating factor (G-CSF) (Fukunaga et al., *Cell*, 61:341–350 (1990a); Fukunaga et al., *Proc. Natl. Acad. Sci. USA*, 87:8702–8706 (1990b); Larsen et al., *J. Exp. Med.*, 172:1559–1570 (1990)), EPO (D'Andrea et al., *Cell*, 57:277–285 (1989); Jones et al., *Blood*, 76:31–35 (1990)), Leukemia inhibitory factor (LIF) (Gearing et al., *EMBO J.*, 10:2839–2848 (1991)), oncostatin M (OSM) (Rose et al., *Proc. Natl. Acad. Sci. USA*, 88:8641–8645 (1991)) and also receptors for prolactin (Boutin et al., *Proc. Natl. Acad. Sci. USA*, 88:7744–7748 (1988); Edery et al., *Proc. Natl. Acad. Sci. USA*, 86:2112–2116 (1989)), growth hormone (GH) (Leung et al., *Nature*, 330:537–543 (1987)), ciliary neurotrophic factor (CNTF) (Davis et al., *Science*, 253:59–63 (1991) and c-Mpl (M. Souyri et al., *Cell* 63:1137 (1990); I. Vigon et al., *Proc. Natl. Acad. Sci.* 89:5640 (1992)).

"Thrombocytopenia" in humans is defined as a platelet count below $150 \times 10^9$ per liter of blood.

"Thrombopoietic activity" is defined as biological activity that consists of accelerating the proliferation, differentiation and/or maturation of megakaryocytes or megakaryocyte precursors into the platelet producing form of these cells. This activity may be measured in various assays including an in vivo mouse platelet rebound synthesis assay, induction of platelet cell surface antigen assay as measured by an anti-platelet immunoassay (anti-$GPII_bIII_a$) for a human leukemia megakaryoblastic cell line (CMK), and induction of polyploidization in a megakaryoblastic cell line (DAMI). A "thrombopoietin receptor" is a mammalian polypeptide receptor which, when activated by a ligand binding thereto, includes, causes or otherwise gives rise to "thrombopoietic activity" in a cell or mammal, including a human.

"Control sequences" when referring to expression means DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

"Operably linked" when referring to nucleic acids means that the nucleic acids are placed in a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adapters or linkers are used in accord with conventional practice.

"Exogenous" when referring to an element means a nucleic acid sequence that is foreign to the cell, or homologous to the cell but in a position within the host cell nucleic acid in which the element is ordinarily not found.

"Cell," "cell line," and "cell culture" are used interchangeably herein and such designations include all progeny of a cell or cell line. Thus, for example, terms like "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

"Plasmids" are autonomously replicating circular DNA molecules possessing independent origins of replication and are designated herein by a lower case "p" preceded and/or followed by capital letters and/or numbers. The starting plasmids herein are either commercially available, publicly available on an unrestricted basis, or can be constructed from such available plasmids in accordance with published procedures. In addition, other equivalent plasmids are known in the art and will be apparent to the ordinary artisan.

"Restriction enzyme digestion" when referring to DNA means catalytic cleavage of internal phosphodiester bonds of DNA with an enzyme that acts only at certain locations or sites in the DNA sequence. Such enzymes are called "restriction endonucleases". Each restriction endonuclease recognizes a specific DNA sequence called a "restriction site" that exhibits two-fold symmetry. The various restriction enzymes used herein are commercially available and their reaction conditions, cofactors, and other requirements as established by the enzyme suppliers are used. Restriction enzymes commonly are designated by abbreviations composed of a capital letter followed by other letters representing the microorganism from which each restriction enzyme originally was obtained and then a number designating the particular enzyme. In general, about 1 µg of plasmid or DNA fragment is used with about 1–2 units of enzyme in about 20 µl of buffer solution. Appropriate buffers and substrate amounts for particular restriction enzymes are specified by the manufacturer. Incubation of about 1 hour at 37° C. is ordinarily used, but may vary in accordance with the supplier's instructions. After incubation, protein or polypeptide is removed by extraction with phenol and chloroform, and the digested nucleic acid is recovered from the aqueous fraction by precipitation with ethanol. Digestion with a restriction enzyme may be followed with bacterial alkaline phosphatase hydrolysis of the terminal 5' phosphates to prevent the two restriction-cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional as described in sections 1.56–1.61 of Sambrook et al., *Molecular Cloning: A Laboratory Manual* (New York: Cold Spring Harbor Laboratory Press, 1989).

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see Lawn et al., *Nucleic Acids Res.,* 9:6103–6114 (1981), and Goeddel et al, *Nucleic Acids Res.,* 8:4057 (1980).

"Southern analysis" or "Southern blotting" is a method by which the presence of DNA sequences in a restriction endonuclease digest of DNA or DNA-containing composition is confirmed by hybridization to a known, labeled oligonucleotide or DNA fragment. Southern analysis typically involves electrophoretic separation of DNA digests on agarose gels, denaturation of the DNA after electrophoretic separation, and transfer of the DNA to nitrocellulose, nylon, or another suitable membrane support for analysis with a radiolabeled, biotinylated, or enzyme-labeled probe as described in sections 9.37–9.52 of Sambrook et al., supra.

"Northern analysis" or "Northern blotting" is a method used to identify RNA sequences that hybridize to a known probe such as an oligonucleotide, DNA fragment, cDNA or fragment thereof, or RNA fragment. The probe is labeled with a radioisotope such as $^{32}P$, or by biotinylation, or with an enzyme. The RNA to be analyzed is usually electrophoretically separated on an agarose or polyacrylamide gel, transferred to nitrocellulose, nylon, or other suitable membrane, and hybridized with the probe, using standard techniques well known in the art such as those described in sections 7.39–7.52 of Sambrook et al., supra.

"Ligation" is the process of forming phosphodiester bonds between two nucleic acid fragments. For ligation of the two fragments, the ends of the fragments must be compatible with each other. In some cases, the ends will be directly compatible after endonuclease digestion. However, it may be necessary first to convert the staggered ends commonly produced after endonuclease digestion to blunt ends to make them compatible for ligation. For blunting the ends, the DNA is treated in a suitable buffer for at least 15 minutes at 15° C. with about 10 units of the Klenow fragment of DNA polymerase I or T4 DNA polymerase in the presence of the four deoxyribonucleotide triphosphates. The DNA is then purified by phenol-chloroform extraction and ethanol precipitation. The DNA fragments that are to be ligated together are put in solution in about equimolar amounts. The solution will also contain ATP, ligase buffer, and a ligase such as T4 DNA ligase at about 10 units per 0.5 $\mu$g of DNA. If the DNA is to be ligated into a vector, the vector is first linearized by digestion with the appropriate restriction endonuclease(s). The linearized fragment is then treated with bacterial alkaline phosphatase or calf intestinal phosphatase to prevent self-ligation during the ligation step.

"Preparation" of DNA from cells means isolating the plasmid DNA from a culture of the host cells. Commonly used methods for DNA preparation are the large- and small-scale plasmid preparations described in sections 1.25–1.33 of Sambrook et al., supra. After preparation of the DNA, it can be purified by methods well known in the art such as that described in section 1.40 of Sambrook et al., supra.

"Oligonucleotides" are short-length, single- or double-stranded polydeoxynucleotides that are chemically synthesized by known methods (such as phosphotriester, phosphite, or phosphoramidite chemistry, using solid-phase techniques such as described in EP 266,032 published May 4, 1988, or via deoxynucleoside H-phosphonate intermediates as described by Froehler et al., *Nucl. Acids Res.,* 14:5399–5407 (1986)). Further methods include the polymerase chain reaction defined below and other autoprimer methods and oligonucleotide syntheses on solid supports.

All of these methods are described in Engels et al., *Agnew. Chem. Int. Ed. Engl,* 28:716–734 (1989). These methods are used if the entire nucleic acid sequence of the gene is known, or the sequence of the nucleic acid complementary to the coding strand is available. Alternatively, if the target amino acid sequence is known, one may infer potential nucleic acid sequences using known and preferred coding residues for each amino acid residue. The oligonucleotides are then purified on polyacrylamide gels.

"Polymerase chain reaction" or "PCR" refers to a procedure or technique in which minute amounts of a specific piece of nucleic acid, RNA and/or DNA, are amplified as described in U.S. Patent No. 4,683,195 issued Jul. 28, 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.,* 51:263 (1987); Erlich, ed., *PCR Technology,* (Stockton Press, NY, 1989). As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

"Native antibodies and immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one and ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia et al., *J. Mol. Biol.,* 186:651–663 (1985); Novotny and Haber, *Proc. Natl. Acad Sci. USA,* 82:4592–4596 (1985)).

The term "variable" refers to the fact that certain portions of the variable domains differ extensively in sequence among antibodies and are used in the binding and specificity of each particular antibody for its particular antigen. However, the variability is not evenly distributed through the variable domains of antibodies. It is concentrated in three segments called complementarity determining regions (CDRs) or hypervariable regions both in the light chain and the heavy chain variable domains. The more highly conserved portions of variable domains are called the framework (FR). The variable domains of native heavy and light chains each comprise four FR regions, largely adopting a b-sheet configuration, connected by three CDRs, which form loops connecting, and in some cases forming part of, the b-sheet structure. The CDRs in each chain are held together in close proximity by the FR regions and, with the CDRs from the other chain, contribute to the formation of the antigen binding site of antibodies (see Kabat et al., *Sequences of Proteins of Immunological Interest*, National Institute of Health, Bethesda, Md. (1987)). The constant domains are not involved directly in binding an antibody to an antigen, but exhibit various effector functions, such as participation of the antibody in antibody-dependent cellular toxicity.

Papain digestion of antibodies produces two identical antigen binding fragments, called "Fab" fragments, each with a single antigen binding site, and a residual "Fc" fragment, whose name reflects its ability to crystallize readily. Pepsin treatment yields an $F(ab')_2$ fragment that has two antigen combining sites and is still capable of cross-linking antigen.

"Fv" is the minimum antibody fragment which contains a complete antigen recognition and binding site. This region consists of a dimer of one heavy and one light chain variable domain in tight, non-covalent association. It is in this configuration that the three CDRs of each variable domain interact to define an antigen binding site on the surface of the $V_H$-$V_L$ dimer. Collectively, the six CDRs confer antigen binding specificity to the antibody.

However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other, chemical couplings of antibody fragments are also known.

The "light chains" of antibodies (immunoglobulins) from any vertebrate species can be assigned to one of two clearly distinct types, called kappa and lambda (1), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g., IgG-b 1, IgG-2, IgG-3, and IgG-4; IgA-1 and IgA-2. The heavy chain constant domains that correspond to the different classes of immunoglobulins are called a, delta, epsilon, g, and $\mu$, respectively. The subunit structures and three-dimensional configurations of different classes of immunoglobulins are well known.

The term "antibody" is used in the broadest sense and specifically covers single monoclonal antibodies (including agonist and antagonist antibodies), antibody compositions with polyepitopic specificity, as well as antibody fragments (e.g., Fab, $F(ab')_2$, scFv and Fv), so long as they exhibit the desired biological activity.

The term "monoclonal antibody" as used herein refers to an antibody obtained from a population of substantially homogeneous antibodies, ie., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler & Milstein, *Nature*, 256:495 (1975), or may be made by recombinant DNA methods (see, e.g., U.S. Pat. No. 4,816,567 (Cabilly et al.)).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity, e.g. binding to and activating mpl (U.S. Pat. No. 4,816,567 (Cabilly et al.); and Morrison et al., Proc. Natl. Acad. Sci. USA, 81:6851–6855 (1984)).

"Humanized" forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Furthermore, humanized antibody may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details see: Jones et al., *Nature*, 321:522–525 (1986); Reichmann et al., *Nature*, 332:323–329 (1988); and Presta, *Curr. Op. Struct. Biol.*, 2:593–596 (1992)).

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_H$ domains which enables the sFv to form the desired structure for antigen binding. For a review of sFv see Pluckthun in *The Pharmacology of Monoclonal Antibodies*, vol. 113, Rosenburg and Moore eds. Springer-Verlag, New York, pp. 269–315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA* 90:6444–6448 (1993).

The expression "linear antibodies" when used throughout this application refers to the antibodies described in Zapata et al. *Protein Eng.* 8(10):1057–1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

A "variant" antibody, refers herein to a molecule which differs in amino acid sequence from a "parent" antibody amino acid sequence by virtue of addition, deletion and/or substitution of one or more amino acid residue(s) in the parent antibody sequence. In the preferred embodiment, the variant comprises one or more amino acid substitution(s) in one or more hypervariable region(s) of the parent antibody. For example, the variant may comprise at least one, e.g from about one to about ten, and preferably from about two to about five, substitutions in one or more hypervariable regions of the parent antibody. Ordinarily, the variant will have an amino acid sequence having at least 75% amino acid sequence identity with the parent antibody heavy or light chain variable domain sequences, more preferably at least 80%, more preferably at least 85%, more preferably at least 90%, and most preferably at least 95%. Identity or homology with respect to this sequence is defined herein as the percentage of amino acid residues in the candidate sequence that are identical with the parent antibody residues, after aligning the sequences and introducing gaps, if necessary, to achieve the maximum percent sequence identity. See FIG. 1. None of N-terminal, C-terminal, or internal extensions, deletions, or insertions into the antibody sequence shall be construed as affecting sequence identity or homology. The variant retains the ability to bind the receptor and preferably has properties which are superior to those of the parent antibody. For example, the variant may have a stronger binding affinity, enhanced ability to activate the receptor, etc. To analyze such properties, one should compare a Fab form of the variant to a Fab form of the parent antibody or a full length form of the variant to a full length form of the parent antibody, for example, since it has been found that the format of the antibody impacts its activity in the biological activity assays disclosed herein. The variant antibody of particular interest herein is one which displays at least about 10 fold, preferably at least about 20 fold, and most preferably at least about 50 fold, enhancement in biological activity when compared to the parent antibody. The "parent" antibody herein is one which is encoded by an amino acid sequence used for the preparation of the variant. Preferably, the parent antibody has a human framework region and has human antibody constant region(s). For example, the parent antibody may be a humanized or human antibody. An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The term "epitope tagged" when used herein refers to an antibody fused to an "epitope tag". The epitope tag polypeptide has enough residues to provide an epitope against which an antibody thereagainst can be made, yet is short enough such that it does not interfere with activity of the antibody. The epitope tag preferably is sufficiently unique so that the antibody thereagainst does not substantially cross-react with other epitopes. Suitable tag polypeptides generally have at least 6 amino acid residues and usually between about 8–50 amino acid residues (preferably between about 9–30 residues). Examples include the flu HA tag polypeptide and its antibody 12CA5 (Field et al. *Mol. Cell. Biol.* 8:2159–2165 (1988)); the c-myc tag and the 8F9, 3C7, 6E10, G4, B7 and 9E10 antibodies thereto (Evan et al., *Mol. Cell. Biol.* 5(12):3610–3616 (1985)); and the Herpes Simplex virus glycoprotein D (gD) tag and its antibody (Paborsky et al., Protein Engineering 3(6):547–553 (1990)). In certain embodiments, the epitope tag is a "salvage receptor binding epitope". As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

The terms "mpl ligand", mpl ligand polypeptide", "ML", "thrombopoietin" or "TPO" are used interchangeably herein and include any polypeptide that possesses the property of binding to mpl, a member of the cytokine receptor superfamily, and having a biological property of mpl ligand. An exemplary biological property is the ability to stimulate the incorporation of labeled nucleotides (e.g. $^3$H-thymidine) into the DNA of IL-3 dependent Ba/F3 cells transfected with human mpl. Another exemplary biological property is the ability to stimulate the incorporation of $^{35}$S into circulating platelets in a mouse platelet rebound assay. This definition encompasses a polypeptide isolated from a mpl ligand source such as aplastic porcine plasma described herein or from another source, such as another animal species, including humans, or prepared by recombinant or synthetic methods. Examples include TPO(332) and $rhTPO_{332}$. Also included in this definition is the thrombopoietic ligand described in WO 95/28907 having a molecular weight of about 31,000 daltons (31 kd) as determined by SDS gel under reducing conditions and 28,000 daltons (28 kd) under non-reducing conditions. The term "TPO" includes variant forms, such as fragments, alleles, isoforms, analogues, chimera thereof and mixtures of these forms. For convenience, all of these ligands will be referred to below simply as "TPO" recognizing that all individual ligands and ligand mixtures are referred to by this term.

Preferably, the TPO is a compound having thrombopoietic activity or being capable of increasing serum platelet counts in a mammal. The TPO is preferably capable of increasing endogenous platelet counts by at least 10%, more preferably by 50%, and most preferably capable of elevating platelet counts in a human to greater than about $150 \times 10^9$ per liter of blood.

The TPO of this invention preferably has at least 70% overall sequence identity with the amino acid sequence of the highly purified substantially homogeneous porcine mpl ligand polypeptide and at least 80% sequence identity with the "EPO-domain" of the porcine mpl ligand polypeptide. Alternatively, the TPO of this invention may be a mature human mpl ligand (hML), or a variant or post-transcriptionally modified form thereof or a protein having about 80% sequence identity with mature human mpl ligand. Alternatively, the TPO may be a fragment, especially an amino-terminus or "EPO-domain" fragment, of the mature human mpl ligand. Preferably, the amino terminus fragment retains substantially all of the human ML sequence between the first and fourth cysteine residues but may contain substantial additions, deletions or substitutions outside that region. According to this embodiment, the fragment polypeptide may be represented by the formula:

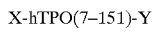

Where hTPO(7–151) represents the human TPO (hML) amino acid sequence from $Cys^7$ through $Cys^{151}$ through $Cys^{151}$ inclusive; X represents the amino group of $Cys^7$ or one or more of the amino-terminus amino acid residue(s) of the mature TPO or amino acid residue extensions thereto such as Met, Lys, Tyr or amino acid substitutions thereof such as arginine to lysine or leader sequences containing, for example, proteolytic cleavage sites (e.g. Factor Xa or thrombin); and Y represents the carboxy terminal group of $Cys^{151}$ or one or more carboxy-terminus amino acid residue (s) of the mature TPO or extensions thereto.

A "TPO fragment" means a portion of a naturally occurring mature full length mpl ligand or TPO sequence having one or more amino acid residues or carbohydrate units deleted. The deleted amino acid residue(s) may occur anywhere in the peptide including at either the N-terminal or C-terminal end or internally, so long as the fragment shares at least one biological property in common with mpl ligand. Mpl ligand fragments typically will have a consecutive sequence of at least 10, 15, 20, 25, 30 or 40 amino acid residues that are identical to the sequences of the mpl ligand isolated from a mammal including the ligand isolated from aplastic porcine plasma or the human or murine ligand, especially the EPO-domain thereof. Representative examples of N-terminal fragments are TPO(153), $hML_{,153}$ or TPO($Met^{-1}$ 1–153).

The terms "TPO isoform(s)" and "TPO sequence isoform (s)" or the term "derivatives" in association with TPO, etc. as used herein means a biologically active material as defined below having less than 100% sequence identity with the TPO isolated from recombinant cell culture, aplastic porcine plasma or the human mpl ligand. Ordinarily, a biologically active mpl ligand or TPO isoform will have an amino acid sequence having at least about 70% amino acid sequence identity with the mpl ligand/TPO isolated from aplastic porcine plasma or the mature murine, human mpl ligand or fragments thereof, preferably at least about 75%, more preferably at least about 80%, still more preferably at least about 85%, even more preferably at least about 90%, and most preferably at least about 95%.

TPO "analogues" include covalent modification of TPO or mpl ligand by linking the TPO polypeptide to one of a variety of nonproteinaceous polymers, e.g polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337. TPO polypeptides covalently linked to the forgoing polymers are referred to herein as pegylated TPO.

Still other preferred TPO polypeptides of this invention include mpl ligand sequence variants and chimeras. Ordinarily, preferred mpl ligand sequence variants and chimeras are biologically active mpl ligand variants that have an amino acid sequence having at least 90% amino acid sequence identity with the human mpl ligand and most preferably at least 95%. An exemplary preferred mpl ligand variant is a N-terminal domain hML variant (referred to as the "EPO-domain" because of its sequence homology to erythropoietin). The preferred hML EPO-domain comprises about the first 153 amino acid residues of mature hML and is referred to as $hML_{153}$. An optionally preferred hML sequence variant comprises one in which one or more of the basic or dibasic amino acid residue(s) in the C-terminal domain is substituted with a non-basic amino acid residue(s) (e.g., hydrophobic, neutral, acidic, aromatic, Gly, Pro and the like). A preferred hML C-terminal domain sequence variant comprises one in which Arg residues 153 and 154 are replaced with Ala residues. This variant is referred to as $hML_{332}$ (R153A, R154A).

A preferred chimera is a fusion between mpl ligand or fragment (defined below) thereof with a heterologous polypeptide or fragment thereof. For example, $hML_{153}$ may be fused to an IgG fragment to improve serum half-life or to IL-3, G-CSF or EPO to produce a molecule with enhanced thrombopoietic or chimeric hematopoietic activity.

Other preferred mpl ligand fragments have a Met preceding the amino terminus Ser (e.g. $Met^-TPO_{153}$). This is preferred when, for example, the protein is expressed directly in a microorganism such as $E$ coli. Optionally, these mpl ligand fragments may contain amino acid substitutions to facilitate derivitization. For example, $Arg_{153}$ or other residues of the carbohydrate domain may be substituted with Lys to create additional sites to add polyethylene glycol. Preferred mpl ligand fragments according to this option include $Met^{-1}$ TPO(1-X) where X is about 153, 164, 191, 199, 205, 207, 217, 229, or 245 for the sequence of residues 1–X. Other preferred mpl ligand fragments include those produced as a result of chemical or enzymatic hydrolysis or digestion of the purified ligand.

"Essentially pure" protein means a composition purified to remove contaminating proteins and other cellular components, preferably comprising at least about 90% by weight of the protein, based on total weight of the composition, more preferably at least about 95% by weight. "Essentially homogeneous" protein means a composition comprising at least about 99% by weight of protein, based on total weight of the composition.

II. Preferred Embodiments of the Invention

In one embodiment, preferred antibodies of this invention are substantially homogeneous antibodies and variants thereof, referred to as agonist antibodies (aAb), that possess the property of binding to c-mpl, a member of the hematopoietic growth factor receptor superfamily, and transducing a survival, proliferation, maturation and/or differentiation signal. Such signal transduction may be determined by measuring stimulation of incorporation of labeled nucleotides ($^3$H-thymidine) into the DNA of IL-3 dependent Ba/F3 cells transfected with human mpl P, or with a CMK Assay measuring Induction of the platelet antigen $GPII_bIII_a$ expression. Signal transduction may also be determined by KIRA ELISA by measuring phosphorylation of the c-mpl-Rse.gD chimeric receptor, in a c-mpl/Mab HU-03 cell proliferation assay or in a liquid suspension megakaryocytopoiesis assay.

Preferred c-mpl agonist antibodies of this invention are also capable of inducing or causing survival, proliferation, maturation or differentiation of CD34+ cells into the platelet producing form at a concentration equal to or not less than 2 orders of magnitude (100-fold) below that of thrombopoietin on a weight basis.

More preferred c-mpl aAb(s) are substantially purified aAb(s) having hematopoietic, especially megakaryocytopoietic or thrombocytopoietic activity—namely, being capable of stimulating proliferation, maturation and/or differentiation of immature megakaryocytes or their predecessors into the mature platelet-producing form that demonstrate a biological activity equal to or within 2 orders of magnitude of that of rhTPO on a weight basis. Most preferred aAb(s) of this invention are human aAb(s) including full length antibodies having an intact human Fc region and including fragments thereof having hematopoietic, megakaryocytopoietic or thrombopoietic activity. Exemplary fragments having the above described biological activity include; Fv, scFv, F(ab'), F(ab')$_2$.

Preferred scFv fragments denominated 10F6, 5E5, 10D10, 12B5, 12D5 and 12E10 having sequences for CDRs and Framework regions provided in FIG. 1. Alternatively, the above enumerated scFvs are affmity matured by mutating 1-3 amino acid residues in one or more of the CDRs or in the framework regions between the CDRs.

The framework regions may be derived from a "consensus sequence" (i.e. the most common amino acids of a class, subclass or subgroup of heavy or light chains of human immunoglobulins) or may be derived from an individual human antibody framework region or from a combination of different framework region sequences. Many human antibody framework region sequences are compiled in Kabat et al., *Sequences of Proteins of Immunological Interest*, 5th Ed. Public Health Service, National Institutes of Health, Bethesda, Md. (1991), pages 647–669), for example.

A suitable method for puriing mpl antibodies comprises contacting an antibody source containing the mpl antibody molecules with an immobilized receptor polypeptide, specifically mpl or a mpl fusion polypeptide, under conditions whereby the mpl antibody molecules to be purified are selectively adsorbed onto the immobilized receptor polypeptide, washing the immobilized support to remove non-adsorbed material, and eluting the molecules to be purified from the immobilized receptor polypeptide with an elution buffer. The source containing the mpl antibody may be a library of antibodies having different binding epitopes and the receptor may be immobilized on a plate, tube, particle or other suitable surface using known methods.

Alternatively, the source containing the antibody is recombinant cell culture where the concentration of antibody in either the culture medium or in cell lysates is generally higher than in plasma or other natural sources. The preferred purification method to provide substantially homogeneous antibody comprises: removing particulate debris, either host cells or lysed fragments by, for example, centrifugation or ultrafiltration; optionally, protein may be concentrated with a commercially available protein concentration filter; followed by separating the antibody from other impurities by one or more steps selected from; immunoaffinity, ion-exchange (e.g., DEAE or matrices containing carboxymethyl or sulfopropyl groups), Blue-SEPHAROSE, CM Blue-SEPHAROSE, MONO-Q, MONO-S, lentil lectin-SEPHAROSE, WGA-SEPHAROSE, Con A-SEPHAROSE, Ether TOYPEARL, Butyl TOYPEARL, Phenyl TOYPEARL, protein A SEPHAROSE, SDS-PAGE, reverse phase HPLC (e.g., silica gel with appended aliphatic groups) or SEPHADEX molecular sieve or size exclusion chromatography, and ethanol or ammonium sulfate precipitation. A protease inhibitor such as methylsulfonylfluoride (PMSF) may be included in any of the foregoing steps to inhibit proteolysis.

Preferably, the isolated antibody is monoclonal (Kohler and Milstein, *Nature,* 256:495–497 (1975); Campbell, *Laboratory Techniques in Biochemistry and Molecular Biology*, Burdon et al., Eds, Volume 13, Elsevier Science Publisrers, Amsterdam (1985); and Huse et al., *Science,* 246:1275–1281 (1989)). A preferred mpl antibody is one that binds to mpl receptor with an affinity of at least about $10^6$ 1/mole. More preferably the antibody binds with an affinity of at least about $10^7$ 1/mole or even at least $10^9$ 1/mole. Most preferably, the antibody is raised against a mpl receptor having one of the above described effector functions. The isolated antibody capable of binding to the mpl receptor may optionally be fused to a second polypeptide and the antibody or fusion thereof may be used to isolate and purify mpl from a source as described above for immobilized mpl polypeptide. In a further preferred aspect of this embodiment, the invention provides a method for detecting the mpl ligand in vitro or in vivo comprising contacting the antibody with a sample, especially a serum sample, suspected of containing the ligand and detecting if binding has occurred.

The invention also provides an isolated nucleic acid molecule encoding the mpl antibody or fragments thereof, which nucleic acid molecule may be labeled or unlabeled with a detectable moiety, and a nucleic acid molecule having a sequence that is complementary to, or hybridizes under stringent or moderately stringent conditions with, a nucleic acid molecule having a sequence encoding a mpt antibody. A preferred mpl antibody nucleic acid is RNA or DNA that encodes a biologically active human antibody.

In a further preferred embodiment of this invention, the nucleic acid molecule is cDNA encoding the mpl antibody and further comprises a replicable vector in which the cDNA is operably linked to control sequences recognized by a host transformed with the vector. This aspect further includes host cells transformed with the vector and a method of using the cDNA to effect production of antibody, comprising expressing the cDNA encoding the antibody in a culture of the transformed host cells and recovering the antibody from the host cell culture. The antibody prepared in this manner is preferably substantially homogeneous human antibody. A preferred host cell for producing the antibody is Chinese hamster ovary (CHO) cells. An alternative preferred host cell is *E coli.*

The invention further includes a preferred method for treating a mammal having an immunological or hematopoietic disorder, especially thrombocytopenia comprising administering a therapeutically effective amount of a mpl agonist or antagonist antibody to the mammal. Optionally, the antibody is administered in combination with a cytokine, especially a colony stimulating factor or interleukin. Preferred colony stimulating factors or interleukins include; kit-ligand, LIF, G-CSF, GM-CSF, M-CSF, EPO, IL-1, IL-2, IL-3, IL-5, IL-6, IL-7, IL-8, IL-9 or IL-11. Alternatively, the antibody is administered in combination with an Insulin-like growth factor (e.g., IGF-1) or a tumor necrosis factor (e.g., lymphotoxin (LT)).

III. Methods of Making

Nucleic acid encoding the agonist and/or antagonist antibodies of the invention can be prepared from a library of single chain antibodies displayed on a bacteriophage. The preparation of such a library is well known to one of skill in this art. Suitable libraries may be prepared by the methods described in WO 92/01047, WO 92/20791, WO 93/06213, WO 93/11236, WO 93/19172, WO 95/01438 and WO 95/15388. In a preferred embodiment, a library of single chain antibodies (scFv) may be generated from a diverse population of human B-cells from human donors. mRNA corresponding to the VH and VH antibody chains is isolated and purified using standard techniques and reverse transcribed to generate a population of cDNA. After PCR amplification, DNA coding for single chain antibodies is assembled using a linker, such as Gly$_4$Ser, and cloned into suitable expression vectors. A phage library is then prepared in which the population of single chain antibodies is displayed on the surface of the phage. Suitable methods for preparing phage libraries have been reviewed and are described in Winter et. al., Annu. Rev. Immunol., 1994, 12:433–55; Soderlind et. al., Immunological Reviews, 1992, 130:109–123; Hoogenboom, Tibtech February 1997, Vol. 15; Neri et. al., Cell Biophysics, 1995, 27:47–61, and the references described therein.

The antibodies of the invention having agonist or antagonist properties may be selected by immobilizing a receptor and then panning a library of human scFv prepared as described above using the immobilized receptor to bind antibody. Griffiths et. al., EMBO-J, 1993, 12:725–734. The specificity and activity of specific clones can be assessed using known assays. Griffiths et. al.; Clarkson et. al., Nature, 1991, 352:642–648. After a first panning step, one obtains a library of phage containing a plurality of different single chain antibodies displayed on phage having improved binding to the receptor. Subsequent panning steps provide additional libraries with higher binding affinities. When avidity effects are a problem, monovalent phage display libraries may be used in which less than 20%, preferably less than 10%, and more preferably less than 1% of the phage display more than one copy of an antibody on the surface of the phage. Monovalent display can be accomplished with the use of phagemid and helper phage as described, for example, in Lowman et. al., Methods: A Companion to Methods in Enzymology, 1991, 3(3):205–216. A preferred phage is M13 and display is preferably as a fusion protein with coat protein 3 as described in Lowman et. al., supra. Other suitable phage include fl and fd filamentous phage. Fusion protein display with other virus coat proteins is also known and may be used in this invention. See U.S. Pat. No. 5,223,409.

Amino acid sequence variants of the antibody are prepared by introducing appropriate nucleotide changes into the antibody DNA, or by peptide synthesis. Such variants include, for example, deletions from, and/or insertions into and/or substitutions of, residues within the amino acid sequences of the antibodies of the examples herein. Any combination of deletion, insertion, and substitution is made to arrive at the final construct, provided that the final construct possesses the desired characteristics. The amino acid changes also may alter post-translational processes of the humanized or variant antibody, such as changing the number or position of glycosylation sites.

A useful method for identification of certain residues or regions of the antibody that are preferred locations for mutagenesis is called "alanine scanning mutagenesis," as described by Cunningham and Wells *Science*, 244:1081–1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with the receptor. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the serum half-life of the antibody.

Another type of variant is an amino acid substitution variant. These variants have at least one amino acid residue in the antibody molecule removed and a different residue inserted in its place. The sites of greatest interest for substitutional mutagenesis include the hypervariable regions, but FR alterations are also contemplated. Conservative substitutions are shown in Table 2 under the heading of "preferred substitutions". If such substitutions result in a change in biological activity, then more substantial changes, denominated "exemplary substitutions" in Table 2, or as further described below in reference to amino acid classes, may be introduced and the products screened.

TABLE 2

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;

(2) neutral hydrophilic: cys, ser, thr;

(3) acidic: asp, glu;

(4) basic: asn, gln, his, lys, arg;

(5) residues that influence chain orientation: gly, pro; and (6) aromatic: trp, tyr, phe.

Non-conservative substitutions will entail exchanging a member of one of these classes for another class.

Any cysteine residue not involved in maintaining the proper conformation of the humanized or variant antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants is affinity maturation using phage using methods known in the art. Briefly, several hypervariable region sites (e.g. 3–7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identified hypervariable region residues contributing significantly to antigen binding. Alternatively, or in addition, it may be beneficial to analyze a crystal structure of the antigen-antibody complex to identify contact points between the antibody and receptor. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

Preferably, the antibodies are prepared by standard recombinant procedures which involve production of the antibodies by culturing cells transfected to express antibody nucleic acid (typically by transforming the cells with an expression vector) and recovering the antibody from the cells of cell culture.

The nucleic acid (e.g., cDNA or genomic DNA) encoding mpl antibody selected as described above is inserted into a replicable vector for further cloning (amplification of the DNA) or for expression. Many vectors are available, and selection of the appropriate vector will depend on (1) whether it is to be used for DNA amplification or for DNA expression, (2) the size of the nucleic acid to be inserted into the vector, and (3) the host cell to be transformed with the vector. Each vector contains various components depending on its function (amplification of DNA or expression of DNA) and the host cell with which it is compatible. The vector components generally include, but are not limited to, one or more of the following: a signal sequence, an origin of replication, one or more marker genes, an enhancer element, a promoter, and a transcription termination sequence.

(i) Signal Sequence Component

The mpl antibody of this invention may be expressed not only directly, but also as a fusion with a heterologous polypeptide, preferably a signal sequence or other polypeptide having a specific cleavage site at the N-terminus of the mature protein or polypeptide. In general, the signal sequence may be a component of the vector, or it may be a part of the mpl antibody DNA that is inserted into the vector. The heterologous signal sequence selected should be one that is recognized and processed (i.e., cleaved by a signal peptidase) by the host cell. For prokaryotic host cells a prokaryotic signal sequence selected, for example, from the group of the alkaline phosphatase, penicillinase, 1pp, or heat-stable enterotoxin II leaders. For yeast secretion the native signal sequence may be substituted by, e.g., the yeast invertase, alpha factor, or acid phosphatase leaders, the *C. albicans* glucoamylase leader (EP 362,179 published Apr. 4, 1990), or the signal described in WO 90/13646 published Nov. 15, 1990. In mammalian cell expression the native signal sequence (ie., the mpl ligand presequence that normally directs secretion of mpl ligand from its native mammalian cells in vivo) is satisfactory, although other mammalian signal sequences may be suitable, such as signal sequences from other mpl ligand polypeptides or from the same mpl ligand from a different animal species, signal sequences from a mpl ligand, and signal sequences from secreted polypeptides of the same or related species, as well as viral secretory leaders, for example, the herpes simplex gD signal.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Most expression vectors are "shuttle" vectors, ie., they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA may also be amplified by insertion into the host genome. This is readily accomplished using Bacillus species as hosts, for example, by including in the vector a DNA sequence that is complementary to a sequence found in Bacillus genomic DNA. Transfection of Bacillus with this vector results in homologous recombination with the genome and insertion of antibody DNA. However, the recovery of genomic DNA encoding antibody is more complex than that of an exogenously replicated vector because restriction enzyme digestion is required to excise the antibody DNA.

(iii) Selection Gene Component

Expression and cloning vectors should contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene express a protein conferring drug resistance and thus survive the selection regimen. Examples of such dominant selection use the drugs neomycin (Southern et at., *J. Molec. Appl. Genet.,* 1:327 (1982)) mycophenolic acid (Mulligan et al., *Science,* 209:1422 (1980)) or hygromycin Sugden et al., *Mol. Cell. Biol.,* 5:410–413 (1985)). The three examples given above employ bacterial genes under eukaryotic control to convey resistance to the appropriate drug G418 or neomycin (geneticin), xgpt (mycophenolic acid), or hygromycin, respectively.

Examples of other suitable selectable markers for mammalian cells are those that enable the identification of cells competent to take up the antibody nucleic acid, such as dihydrofolate reductase (DHFR) or thymidine kinase. The mammalian cell transformants are placed under selection pressure that only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes antibody. Amplification is the process by which genes in greater demand for the production of a protein critical for growth are reiterated in tandem within the chromosomes of successive generations of recombinant cells. Increased quantities of antibody are synthesized from the amplified DNA.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasin, *Proc. Natl. Acad. Sci. USA,* 77:4216 (1980). The transformed cells are then exposed to increased levels of Mtx. This leads to the synthesis of multiple copies of the DHFR gene, and, concomitantly, multiple copies of other DNA comprising the expression vectors, such as the DNA encoding antibody. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060). Alternatively, host cells (particularly wild-type hosts that contain endogenous DHFR) transformed or co-transformed with DNA sequences encoding antibody, wild-type DHFR protein, and another selectable marker such as aminoglycoside 3' phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature,* 282:39 (1979); Kingsman et al., *Gene,* 7:141 (1979); or Tschemper et al., *Gene,* 10:157 (1980)). The trp1 gene provides a selection marker for a mutant strain of yeast lacking the ability to grow in tryptophan, for example, ATCC No. 44076 or PEP4-1 (Jones, Genetics, 85:12 (1977)). The presence of the trp1 lesion in the yeast host cell genome then provides an effective environment for detecting transformation by growth in the absence of tryptophan. Similarly, Leu2-deficient yeast strains (ATCC No. 20,622 or 38,626) are complemented by known plasmids bearing the Leu2 gene.

(iv) Promoter Component

Expression and cloning vectors usually contain a promoter that is recognized by the host organism and is operably linked to the antibody nucleic acid. Promoters are untranslated sequences located upstream (5') to the start codon of a structural gene (generally within about 100 to 1000 bp) that control the transcription and translation of particular nucleic acid sequence, such as the antibody nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to antibody encoding DNA by removing the promoter from the source DNA by restriction enzyme digestion and inserting the isolated promoter sequence into the vector. Both the native antibody promoter sequence and many heterologous promoters may be used to direct amplification and/or expression of the antibody DNA. However, heterologous promoters are preferred, as they generally permit greater transcription and higher yields of expressed antibody as compared to the native promoter.

Promoters suitable for use with prokaryotic hosts include the β-lactamase and lactose promoter systems (Chang et al, *Nature,* 275:615 (1978); and Goeddel et al., *Nature,* 281:544 (1979)), alkaline phosphatase, a tryptophan (trp) promoter system (Goeddel, *Nucleic Acids Res.,* 8:4057 (1980) and EP 36,776) and hybrid promoters such as the tac promoter (deBoer et al., *Proc. Natl. Acad. Sci. USA*, 80:21–25 (1983)). However, other known bacterial promoters are suitable. Their nucleotide sequences have been published, thereby enabling a skilled worker operably to ligate them to DNA encoding antibody (Siebenlist et al., *Cell*, 20:269 (1980)) using linkers or adapters to supply any required restriction sites. Promoters for use in bacterial systems also will contain a Shine-Dalgarno (S.D.) sequence operably linked to the DNA encoding antibody polypeptide.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase (Hitzeman et al., *J. Biol. Chem.*, 255:2073 (1980)) or other glycolytic enzymes (Hess et al., *J. Adv. Enzyme Reg.*, 7:149 (1968); and Holland, *Biochemistry*, 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman et al., EP 73,657A. Yeast enhancers also are advantageously used with yeast promoters.

Antibody transcription from vectors in mammalian host cells may be controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, and from the promoter normally associated with the antibody sequence, provided such promoters are compatible with the host cell systems.

The early and late promoters of the SV40 virus are conveniently obtained as an SV40 restriction fragment that also contains the SV40 viral origin of replication. Fiers et al., *Nature*, 273:113 (1978); Mulligan and Berg, *Science*, 209:1422–1427 (1980); Pavlakis et al., *Proc. Natl. Acad. Sci. USA*, 78:7398–7402 (1981). The immediate early promoter of the human cytomegalovirus is conveniently obtained as a HindIII E restriction fragment. Greenaway et al., *Gene*, 18:355–360 (1982). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., *Nature*, 295:503–508 (1982) on expressing cDNA encoding immune interferon in monkey cells; Reyes et al., *Nature*, 297:598–601 (1982) on expression of human β-interferon cDNA in mouse cells under the control of a thymidine kinase promoter from herpes simplex virus; Canaani and Berg, *Proc. Natl. Acad. Sci. USA*, 79:5166–5170 (1982) on expression of the human interferon β1 gene in cultured mouse and rabbit cells; and Gorman et al., *Proc. Natl. Acad. Sci. USA*, 79:6777–6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

(v) Enhancer Element Component

Transcription of a DNA encoding the antibody of this invention by higher eukaryotes is often increased by inserting an enhancer sequence into the vector. Enhancers are cis-acting elements of DNA, usually about from 10 to 300 bp, that act on a promoter to increase its transcription. Enhancers are relatively orientation and position independent, having been found 5' (Laimins et al., *Proc. Natl. Acad. Sci. USA*, 78:993 (1981)) and 3' (Lusky et al., *Mol. Cell Bio.*, 3:1108 (1983)) to the transcription unit, within an intron (Banerji et al., *Cell*, 33:729 (1983)), as well as within the coding sequence itself (Osborne et al., *Mol. Cell Bio.*, 4:1293 (1984)). Many enhancer sequences are now known from mammalian genes (globin, elastase, albumin, a-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature*, 297:17–18 (1982) on enhancing elements for activation of eukaryotic promoters. The enhancer may be spliced into the vector at a position 5' or 3' to the antibody encoding sequence, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3' untranslated regions of eukaryotic or viral DNAs or cDNAs. These regions contain nucleotide segments transcribed as polyadenylated fragments in the untranslated portion of the mRNA encoding antibody.

(vii) Construction and Analysis of Vectors

Construction of suitable vectors containing one or more of the above listed components employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC No. 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.*, 9:309 (1981) or by the method of Maxam et al., *Methods in Enzymology*, 65:499 (1980).

(viii) Transient Expression Vectors

Particularly useful in the practice of this invention are expression vectors that provide for the transient expression in mammalian cells of DNA encoding the antibody polypeptide. In general, transient expression involves the use of an expression vector that is able to replicate efficiently in a host cell, such that the host cell accumulates many copies of the expression vector and, in turn, synthesizes high levels of a desired polypeptide encoded by the expression vector. Sambrook et al., supra, pp. 16.17–16.22. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying analogues and variants of antibody polypeptide that have antibody polypeptide biological activity.

(ix) Suitable Exemplary Vertebrate Cell Vectors

Other methods, vectors, and host cells suitable for adaptation to the synthesis of the antibody in recombinant vertebrate cell culture are described in Gething et al., *Nature*, 293:620–625 (1981); Mantei et al., *Nature*, 281:40–46 (1979); Levinson et al.; EP 117,060; and EP 117,058. A particularly useful plasmid for mammalian cell culture expression is pRK5 (EP 307,247 U.S. Pat. No. 5,258,287) or pSVI6B (PCT Publication No. WO 91/08291).

D. Selection and Transformation of Host Cells

Suitable host cells for cloning or expressing the vectors herein are the prokaryote, yeast, or higher eukaryotic cells described above. Suitable prokaryotes include eubacteria, such as Gram-negative or Gram-positive organisms, for example, *E. coli*, Bacilli such as *B. subtilis*, Pseudomonas species such as *P. aeruginosa, Salmonella typhimurium*, or *Serratia marcescans*. One preferred *E. coli* cloning host is *E. coli* 294 (ATCC No. 31,446), although other strains such as *E. coli* B, *E. coli* X1776 (ATCC No. 31,537), and *E. coli* W3110 (ATCC No. 27,325) are suitable. These examples are illustrative rather than limiting. Preferably the host cell should secrete minimal amounts of proteolytic enzymes. Alternatively, in vitro methods of cloning, e.g., PCR or other nucleic acid polymerase reactions, are suitable.

In addition to prokaryotes, eukaryotic microbes such as filamentous fungi or yeast are suitable hosts for antibody encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe* (Beach and Nurse, *Nature*, 290:140 (1981); EP 139,383 published May 2, 1985), Kluyveromyces hosts (U.S. Pat. No. 4,943,529) such as, e.g, *K. lactis* (Louvencourt et al., *J. Bacteriol.*, 737 (1983)), *K. fragilis, K. bulgaricus, K. thermotolerans,* and *K. marxianus, yarrowia* (EP 402,226), *Pichia pastoris* (EP 183,070; Sreekrishna et al., *J. Basic Microbiol.*, 28:265–278 (1988)), Candida, *Trichoderma reesia* (EP 244,234), *Neurospora crassa* (Case et al., *Proc. Natl. Acad. Sci. USA*, 76:5259–5263 (1979)), and filamentous fungi such as, e.g., Neurospora, Penicillium, Tolypocladium (WO 91/00357 published Jan. 10, 1991), and Aspergillus hosts such as *A. nidulans* (Ballance et al., *Biochem. Biophys. Res. Commun.*, 112:284–289 (1983); Tilburn et al., *Gene*, 26:205–221 (1983); Yelton et al., *Proc. Natl. Acad Sci. USA*, 81:1470–1474 (1984)) and *A. niger* (Kelly and Hynes, *EMBO J.*, 4:475–479 (1985)).

Suitable host cells for the expression of glycosylated antibody are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. See, e.g., Luckow et al., *Bio/Technology*, 6:47–55 (1988); Miller et al., *Genetic Engineering*, Setlow et al., eds., Vol. 8 (Plenum Publishing, 1986), pp. 277–279; and Maeda et al., *Nature*, 315:592–594 (1985). A variety of viral strains for transfection are publicly available, e.g., the L-1 variant of Autographa californica NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously manipulated to contain the antibody DNA. During incubation of the plant cell culture with *A. tumefaciens*, the DNA encoding the antibody is transferred to the plant cell host such that it is transfected, and will, under appropriate conditions, express the antibody DNA. In addition, regulatory and signal sequences compatible with plant cells are available, such as the nopaline synthase promoter and polyadenylation signal sequences. Depicker et al., *J. Mol. Appl. Gen.*, 1:561 (1982). In addition, DNA segments isolated from the upstream region of the T-DNA 780 gene are capable of activating or increasing transcription levels of plant-expressible genes in recombinant DNA-containing plant tissue. EP 321,196 published Jun. 21, 1989.

However, interest has been greatest in vertebrate cells, and propagation of vertebrate cells in culture (tissue culture) has become a routine procedure in recent years (Tissue Culture, Academic Press, Kruse and Patterson, editors (1973)). Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); baby hamster kidney cells (BHK, ATCC CCL 10); Chinese hamster ovary cells/-DHFR (CHO, Urlaub and Chasin, *Proc. Natl. Acad. Sci. USA*, 77:4216 (1980)); mouse sertoli cells (TM4, Mather, *Biol. Reprod.*, 23:243–251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y Acad. Sci.*, 383:44–68 (1982)); MRC 5 cells; FS4 cells; and a human hepatoma line (Hep G2).

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., supra, is generally used for prokaryotes or other cells that contain substantial cell-wall barriers. Infection with *Agrobacterium tumefaciens* is used for transformation of certain plant cells, as described by Shaw et al., *Gene*, 23:315 (1983) and WO 89/05859 published Jun. 29, 1989. In addition, plants may be transfected using ultrasound treatment as described in WO 91/00358 published Jan. 10, 1991. For mammalian cells without such cell walls, the calcium phosphate precipitation method of Graham and van der Eb, *Virology*, 52:456–457 (1978) is preferred. General aspects of mammalian cell host system transformations have been described by Axel in U.S. Pat. No. 4,399,216 issued Aug. 16, 1983. Transformations into yeast are typically carried out according to the method of Van Solingen et al., *J. Bact.*, 130:946 (1977) and Hsiao et al., *Proc. Natl. Acad Sci. (USA)*, 76:3829 (1979). However, other methods for introducing DNA into cells such as by nuclear injection, electroporation, or protoplast fusion may also be used.

E. Culturing the Host Cells

Prokaryotic cells used to produce the antibody polypeptide of this invention are cultured in suitable media as described generally in Sambrook et al., supra.

The mammalian host cells used to produce the antibody of this invention may be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham and Wallace, *Meth. Enz.*, 58:44 (1979), Barnes and Sato, *Anal. Biochem.*, 102:255 (1980), U.S. Pat. No. 4,767,704; 4,657,866; 4,927,762; or 4,560,655; WO 90/03430; WO 87/00195; U.S. Pat No. Re. 30,985; or copending U.S.Ser. No. 07/592,107 or 07/592,141, both filed on Oct. 3, 1990, the disclosures of all of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

The host cells referred to in this disclosure encompass cells in in vitro culture as well as cells that are within a host animal.

F. Detecting Gene Amplification/Expression

Gene amplification and/or expression may be measured in a sample directly, for example, by conventional Southern blotting, northern blotting to quantitate the transcription of mRNA (Thomas, *Proc. Natl. Acad. Sci. USA*, 77:5201–5205 (1980)), dot blotting (DNA analysis), or in situ hybridization, using an appropriately labeled probe, based on the sequences provided herein. Various labels may be employed, most commonly radioisotopes, particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hsu et al., *Am. J. Clin. Path.*, 75:734–738 (1980).

G. Purification of Antibody

Antibody preferably is recovered from the culture medium as a secreted polypeptide, although it also may be recovered from host cell lysates when directly expressed without a secretory signal.

When the antibody is expressed in a recombinant cell other than one of human origin, the antibody is completely free of proteins or polypeptides of human origin. However, it is still usually necessary to purify the antibody from other recombinant cell proteins or polypeptides to obtain preparations that are substantially homogeneous as to the mpl ligand per se. As a first step, the culture medium or lysate is centrifuged to remove particulate cell debris. The membrane and soluble protein fractions are then separated. Alternatively, a commercially available protein concentration filter (e.g., AMICON or Millipore PELLICON ultrafiltration units) may be used. The antibody may then be purified from the soluble protein fraction. The antibody thereafter is purified from contaminant soluble proteins and polypeptides by salting out and exchange or chromatographic procedures employing various gel matrices. These matrices include; acrylamide, agarose, dextran, cellulose and others common to protein purification. Exemplary chromatography procedures suitable for protein purification include immunoaffinity, receptor affinity (e.g., mpl-IgG or protein A SEPHAROSE), hydrophobic interaction chromatography (HIC) (e.g., ether, butyl, or phenyl Toyopearl), lectin chromatography (e.g., Con A-SEPHAROSE, lentil-lectin-SEPHAROSE), size exclusion (e.g., SEPHADEX G-75), cation- and anion-exchange columns (e.g., DEAE or carboxymethyl- and sulfopropyl-cellulose), and reverse-phase high performance liquid chromatography (RP-HPLC) (see e.g., Urdal et al., *J. Chromatog.*, 296:171 (1984) where two sequential RP-HPLC steps are used to purify recombinant human IL-2). Other purification steps optionally include; ethanol precipitation; ammonium sulfate precipitation; chromatofocusing; preparative SDS-PAGE, and the like.

Antibody variants in which residues have been deleted, inserted, or substituted are recovered in the same fashion, taking account of any substantial changes in properties occasioned by the variation. For example, preparation of a an antibody fusion with another protein or polypeptide, e.g., a bacterial or viral antigen, facilitates purification; an immunoaffinity column containing antibody to the antigen can be used to adsorb the fusion polypeptide. Immunoaffinity columns such as a rabbit polyclonal anti-antibody column can be employed to absorb the antibody variant by binding it to at least one remaining immune epitope. Alternatively, the antibody may be purified by affinity chromatography using a purified receptor-IgG coupled to a (preferably) immobilized resin such as AFFI-Gel 10 (Bio-Rad, Richmond, Calif.) or the like, by means well known in the art. A protease inhibitor such as phenyl methyl sulfonyl fluoride (PMSF) also may be useful to inhibit proteolytic degradation during purification, and antibiotics may be included to prevent the growth of adventitious contaminants. One skilled in the art will appreciate that purification methods suitable for native the antibody may require modification to account for changes in the character of the antibody or its variants upon expression in recombinant cell culture.

In a most preferred embodiment of the invention, the antibodies are agonist antibodies (aAb). By "agonist antibody" is meant an antibody which is able to bind to and to activate, a particular hematopoietic growth factor receptor. For example, the agonist may bind to the extracellular domain of the receptor and thereby cause differentiation and proliferation of megakaryocyte colonies in semisolid cultures and single megakaryocytes in liquid suspension cultures and platelet production in vitro and/or in vivo. The agonist antibodies are preferably against epitopes within the extracellular domain of the receptor Accordingly, the antibody preferably binds to substantially the same epitope as the 12E10, 12B5, 10F6, and 12D5 monoclonal antibodies specifically disclo herein. Most preferably, the antibody will also have substantially the same or greater antigen binding affinity as the monoclonal antibodies disclosed herein. To determine whether a monoclonal antibody has the same specificity as an antibody specifically disclosed, one can, for example, use a competitive ELISA binding assay.

DNA encoding the monoclonal antibodies useful in the method of the invention is readily isolated and sequenced using conventional procedures (e.g., by using oligonucleotide probes that are capable of binding specifically to genes encoding the heavy and light chains of human antibodies). The phage of the invention serve as a preferred source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce immunoglobulin protein, to obtain the synthesis of monoclonal antibodies in the recombinant host cells.

IV. Utility

The antibodies disclosed herein are useful for in vitro diagnostic assays for activating the receptor of interest. This is useful in order to study the role of the receptor in megakaryocyte growth and/or differentiation and platelet production.

The biologically active c-mpl agonist antibody capable of stimulating either proliferation, differentiation or maturation and/or modulation (either stimulation or inhibition) of apoptosis of hematopoietic cells may be used in a sterile pharmaceutical preparation or formulation to stimulate megakaryocytopoietic or thrombopoietic activity in patients suffering from thrombocytopenia due to impaired production, sequestration, or increased destruction of platelets. Thrombocytopenia-associated bone marrow hypoplasia (e.g. aplastic anemia following chemotherapy or bone marrow transplant) may be effectively treated with the aAb compounds of this invention as well as disorders such as disseminated intravascular coagulation (DIC), immune thrombocytopenia (including HIV-induced ITP and non HIV-induced ITP), chronic idiopathic thrombocytopenia, congenital thrombocytopenia, myelodysplasia, and thrombotic thrombocytopenia.

Preferred uses of the megakaryocytopoietic or thrombocytopoietic biologically active c-mpl agonist antibody of this invention are in: myelotoxic chemotherapy for treatment of leukemia or solid tumors, myeloablative chemotherapy for autologous or allogeneic bone marrow transplant, myelodysplasia, idiopathic aplastic anemia, congenital thrombocytopenia, and immune thrombocytopenia.

The biologically active c-mpl agonist antibody of the instant invention may be employed alone or in combination with other cytokines, hematopoietins, interleukins, growth factors, or antibodies in the treatment of the above-identified disorders and conditions. Thus, the instant compounds may be employed in combination with other protein or peptide having hematopoietic activity including G-CSF, GM-CSF, LIF, M-CSF, IL-1, IL-3, erythropoietin (EPO), kit ligand, IL-6, and IL-11.

The biologically active c-mpl agonist antibody of the instant invention may be used in the same way and for the same indications as thrombopoietin (TPO). Some forms of the aAb have a longer half-life than native or pegylated TPO and thus are used in indications where a longer half-life are indicated.

When used for in vivo administration, the antibody formulation must be sterile. This is readily accomplished by filtration through sterile filtration membranes, prior to or following lyophilization and reconstitution. The antibody ordinarily will be stored in lyophilized form or in solution.

Therapeutic antibody compositions generally are placed into a container having a sterile access port, for example, an intravenous solution bag or vial having a stopper pierceable by a hypodermic injection needle.

The route of antibody administration is in accord with known methods, e.g., injection or infusion by intravenous, intraperitoneal, intracerebral, intramuscular, intraocular, intraarterial, intrathecal, inhalation or intralesional routes, or by sustained release systems as noted below. The antibody is preferably administered continuously by infusion or by bolus injection.

An effective amount of antibody to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. Typically, the clinician will administer antibody until a dosage is reached that achieves the desired effect. The progress of this therapy is easily monitored by conventional assays.

The antibodies of the invention may be prepared in a mixture with a pharmaceutically acceptable carrier. This therapeutic composition can be administered intravenously or through the nose or lung, preferably as a liquid or powder aerosol (lyophilized). The composition may also be administered parenterally or subcutaneously as desired. When administered systematically, the therapeutic composition should be sterile, pyrogen-free and in a parenterally acceptable solution having due regard for pH, isotonicity, and stability. These conditions are known to those skilled in the art. Briefly, dosage formulations of the compounds of the present invention are prepared for storage or administration by mixing the compound having the desired degree of purity with physiologically acceptable carriers, excipients, or stabilizers. Such materials are non-toxic to the recipients at the dosages and concentrations employed, and include buffers such as TRIS HCl, phosphate, citrate, acetate and other organic acid salts; antioxidants such as ascorbic acid; low molecular weight (less than about ten residues) peptides such as polyarginine, proteins, such as serum albumin, gelatin, or immunoglobulins; hydrophilic polymers such as polyvinylpyrrolidinone; amino acids such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium and/or nonionic surfactants such as TWEEN, PLURONICS or polyethyleneglycol.

Sterile compositions for injection can be formulated according to conventional pharmaceutical practice. For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice.

Suitable examples of sustained-release preparations include semipermeable matrices of solid hydrophobic polymers containing the polypeptide, which matrices are in the form of shaped articles. e.g., films, or microcapsules. Examples of sustained-release matrices include polyesters, hydrogels (e.g., poly(2-hydroxyethyl-methacrylate) as described by Langer et al., *J. Biomed Mater. Res.*, 15:167–277 (1981) and Langer, *Chem. Tech.*, 12:98–105 (1982) or poly(vinylalcohol)), polylactides (U.S. Pat. No. 3,773,919, EP 58,481), copolymers of L-glutamic acid and gamma ethyl-L-glutamate (Sidman et al., *Biopolymers*, 22:547–556 (1983)), non-degradable ethylene-vinyl acetate (Langer et al., supra), degradable lactic acid-glycolic acid copolymers such as the LUPRON Depot™ (injectable microspheres composed of lactic acid-glycolic acid copolymer and leuprolide acetate), and poly-D-(-)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S-S bond formation through disulfide interchange, stabilization may be achieved by modifying sulfhydryl residues, lyophilizing from acidic solutions, controlling moisture content, using appropriate additives, and developing specific polymer matrix compositions.

Sustained-release compositions also include liposomally entrapped TPO. Liposomes containing TPO are prepared by methods knownper se: U.S. Pat. No. DE 3,218,121; Epstein et al., *Proc. Natl. Acad. Sci. USA*, 82:3688–3692 (1985); Hwang et al., *Proc. Natl. Acad. Sci. USA*, 77:4030–4034 (1980); EP 52,322; EP 36,676; EP 88,046; EP 143,949; 142,641; Japanese patent application 83–118008; U.S. Pat. Nos. 4,485,045 and 4,544,545; and EP 102,324. Ordinarily the liposomes are of the small (about 200–800 Angstroms) unilamellar type in which the lipid content is greater than about 30 mol. % cholesterol, the selected proportion being adjusted for the optimal therapy. The dosage of the antibody will be determined by the attending physician taking into consideration various factors known to modify the action of drugs including severity and type of disease, body weight, sex, diet, time and route of administration, other medications and other relevant clinical factors. Therapeutically effective dosages may be determined by either in vitro or in vivo methods.

An effective amount of the agonist antibody to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 1 $\mu$g/kg to up to 1000 mg/kg or more, depending on the factors mentioned above. Typically, the clinician will administer the molecule until a dosage is reached that achieves the desired effect. The progress of this therapy is easily monitored by conventional assays.

Depending on the type and severity of the disease, from about 0.001 mg/kg to about 1000 mg/kg, more preferably about 0.01 mg to 100 mg/kg, more preferably about 0.010 to 20 mg/kg of the agonist antibody might be an initial candidate dosage for administration to the patient, whether, for example, by one or more separate administrations, or by continuous infusion. For repeated administrations over several days or longer, depending on the condition, the treatment is repeated until a desired suppression of disease symptoms occurs or the desired improvement in the patient's condition is achieved. However, other dosage regimens may also be useful.

EXAMPLES

Without further description, it is believed that one of ordinary skill in the art can, using the preceding description and illustrative examples, make and utilize the present invention to the fullest extent. The following working aexamples therefore specifically point out preferred embodiments of the present invention, and are not to be construed as limiting in any way of the remainder of the disclosure.

Example 1

Assays

The mpl agonist antibody assays were conducted essentially as described in WO 95/18858.

(a) Ba/F3 Cell Proliferation Assay

The Ba/F3-mpl cell line was established (F. de Sauvage et al., *Nature*, 369:533 (1994)) by introduction of the cDNA encoding the entire mpl receptor into the IL-3 dependent murine lymphoblastoid cell line Ba/F3. Stimulation of proliferation of Ba/F3-mpl cells in response to various concentrations of antibodies or TPO was measured by the amount of incorporation of $^3$H-thymidine as previously described (F. de Sauvage et al., supra).

(b) CMK Assay for Induction of Platelet Antigen $GPII_bIII_a$ Expression

CMK cells are maintained in RMPI 1640 medium (Sigma) supplemented with 10% fetal bovine serum and 10 mM glutamine. In preparation for the assay, the cells are harvested, washed and resuspended at $5 \times 10^5$ cells/ml in serum-free GIF medium supplemented with 5 mg/l bovine insulin, 10 mg/l apo-transferrin, 1×trace elements. In a 96-well flat-bottom plate, the TPO standard or experimental agonist antibody samples are added to each well at appropriate dilutions in 100 ml volumes. 100 ml of the CMK cell suspension is added to each well and the plates are incubated at 37° C., in a 5% $CO_2$ incubator for 48 hours. After incubation, the plates are spun at 1000 rpm at 4° C. for five minutes. Supernatants are discarded and 100 ml of the FITC-conjugated $GPII_bIII_a$ monoclonal 2D2 antibody is added to each well. Following incubation at 4° C. for 1 hour, plates are spun again at 1000 rpm for five minutes. The supernatants containing unbound antibody are discarded and 200 ml of 0.1% BSA-PBS wash is added to each well. The 0.1% BSA-PBS wash step is repeated three times. Cells are then analyzed on a FASCAN using standard one parameter analysis measuring relative fluorescence intensity.

(c) KIRA ELISA for Measuring Phosihorylation of the mpl-Rse.gD Chimeric Receptor The human mpl receptor has been disclosed by Vigon et al., *PNAS, USA* 89:5640–5644 (1992). A chimeric receptor comprising the extracellular domain (ECD) of the mpl receptor and the transmembrane and intracellular domain (ICD) of Rse (Mark et al., *J. Biol. Chem.* 269(14): 10720–10728 (1994)) with a carboxyl-terminal flag polypeptide (i.e. Rse.gD) was made for use in the KIRA ELISA described herein.

(i) Capture Agent Preparation

Monoclonal anti-gD (clone 5B6) was produced against a peptide from Herpes simplex virus glycoprotein D (Paborsky et al., Protein Engineering 3(6):547–553 (1990)). The purified stock preparation was adjusted to 3.0 mg/ml in phosphate buffered saline (PBS), pH 7.4 and 1.0 ml aliquots were stored at −20° C.

(ii) Anti-phosphotyrosine Antibody Preparation

Monoclonal anti-phosphotyrosine, clone 4G10, was purchased from UBI (Lake Placid, N.Y.) and biotinylated using long-arm biotin-N-hydroxysuccinamide (Biotin-X-NHS, Research Organics, Cleveland, Ohio.).

(iii) Ligand

The mpl ligand was prepared by the recombinant techniques described herein. The purified mp(ligand was stored at 4° C. as a stock solution.

KIRA ELISA results for agonist antibodies of the invention are shown in FIG. 9. This assay indicates that the antibodies of the invention activate the mpl receptor to a degree similar to the cognate ligand TPO.

(d) TPO Receptor-binding Inhibition Assay

NUNC 96-well immunoplates were coated with 50 µl of rabbit anti-human IgG Fc (Jackson Labs) at 2 µg/ml in carbonate buffer (pH9.6) overnight at 4° C. After blocking with ELISA buffer (PBS, 1% BSA, 0.2% TWEEN 20), the plates were incubated for 2 hr with conditioned media from mpl-Ig-transfected 293 cells. Plates were washed, and 2.5 ng/ml biotinylated TPO was added in the presence or absence of various concentrations of antibodies. After incubation for 1 hr and washing, the amount of TPO bound was detected by incubation with streptAvidin-HRP (Sigma) followed by TMB peroxidase substrate (Kirkegaard & Perry). All dilutions were performed in ELISA buffer, and all incubations were at room temperature. Color development was quenched with $H_3PO_4$ and absorbance was read at 450–650 nm.

(e) HU-03 Cell Proliferation Assay

The HU-01 cell line (D. Morgan, Hahnemann University) is derived from a patient with acute megakaryoblastic leukemia and is dependent on granulocyte-macrophage colony stimulating factor (GM-CSF) for growth. The HU-03 cell line used here was derived from HU-01 cells by adaptation to growth in rhTPO rather than GM-CSF.

HU-03 cells were maintained in RPMI 1640 supplemented with 2% heat-inactivated human male serum and 5 ng/ml rhTPO. Before assay, cells were starved by removing TPO, decreasing serum concentration to 1%, and adjusting the concentration of cells to $2.5 \times 10^5$ cells/ml, followed by incubation for 16 hr. Cells were then washed and seeded into 96-well plates at a density of $5 \times 10^4$ cells per well in medium containing TPO or antibodies at various concentrations. Quadruplicate assays were performed. 1 µCi 3H-thymidine was added to each well before incubation for 24 hr. Cells were collected with a Packard cell harvester and incorporation of $^3$H-thymidine was measured with a Top Count Counter (Packard).

(f) Liquid Suspension Megakarvocytopoeisis Assay

The effect of Mpl agonist antibodies on human megakaryocytopoiesis was determined using a modification of the liquid suspension assay previously described (Grant et al., Blood 69:1334–1339 (1997)). Buffy coats were collected from human umbilical cord blood and cells washed in phosphate-buffered saline (PBS) by centrifugation at 120 g for 15 min at room temperature to remove platelet-rich plasma. Cell pellets were resuspended in Iscove's modified Dulbecco's medium (IMDM, GIBCO) (supplemented with 100 units per ml penicillin and streptomycin), layered onto 60% percoll (density=1.077 gm/ml, Pharmacia), and centrifuged at 800 g for 20 min at room temperature. The light-density mononuclear cells were collected from the interface and washed twice with IMDM. Cells were seeded at $1 \times 10^6$ cells per ml in IMDM supplemented with 30% fetal bovine serum (FBS), 100 units per ml penicillin and streptomycin, and 20 µM 2-mercaptoethanol, into 24-well tissue culture plates (COSTAR). Serial dilutions of thrombopoietin (TPO) or the Fab'2 forms of antibody 12B5 or antibody 12D5 were added to quadruplicate wells; control wells contained no additional supplements. Final volumes were 1 ml per well. The cultures were grown in a humidified incubator at 37° C. in 5% $CO_2$ for 14 days. Megakaryocytopoiesis was quantified using radiolabelled murine monoclonal antibody HP1-1D (provided by W. L. Nichols, Mayo Clinic) which has been shown to be specific for the human megakaryocyte glycoprotein IIb/IIIa (Grant et al., supra). Cells were harvested from the tissue culture plates, washed twice with assay buffer (20% FBS, 0.002% EDTA in PBS), and resuspended in 100 µl assay buffer containing 20 ng iodinated HP1-1D (approximatedly 100,000 cpm). After incubation at room temperature for 1 hr, the cells were washed twice with assay buffer and the cell pellets counted with a gamma counter.

FBS used in this assay was treated with Dextran T40 at 1 mg/ml and charcoal at 10 mg/ml for 30 min, centrifuged, decanted, filter sterilized and heat inactivated at 56° C. for 30 min.

(g) TPO-antibody Competitive Binding Assays for HU-03 Cells and Human Platelets

HU-03 cells were cultured as described above. Platelet rich plasma (PRP) was prepared by centrifugation of citrated whole blood at 400 g's for 5 minutes. Binding studies were conducted within three hours of collection. $^{125}$I-TPO was prepared by indirect iodination (Fielder, P. J., Hass, P., Nagel, M., Stefanich, E., Widmer, R., Bennett, G. L., Keller, G., de Savage, F. J., and Eaton, D. 1997. Human platelets as a model for the binding and degradation of thrombopoietin. Blood 89: 2782–2788) and yielded a specific activity of 15–50 µCi/µg protein.

In a volume of 110 microliters containing 100 pM iodinated TPO, $2 \times 10^6$ washed HU-03 cells in Hank's Balanced Salt Solution,5 mg/ml bovine serum albumin (HBSSB), or $4 \times 10_7$ platelets in plasma, were incubated at 37° C. for minutes with varying concentrations of antibody in triplicate. HU-03 cells were agitated during the incubation period to keep them in suspension. The reaction mixture was overlayed on 1 ml 20% sucrose-HBSSB and microcentrifuged at 13,500 rpm for five minutes. The supernatants were aspirated, tube bottoms containing the cell pellets were cut off, and cell- or platelet-associated radioactivity was measured with an Iso Data Model 120 gamma counter.

Results for several agonist antibodies on the invention in this assay are shown in FIG. 10. Longer bars in the graphs indicate greater amounts of bound radiolabeled TPO and less competition by the agonist antibody at a particular concentration.

(h) Affinity Determinations

The receptor-binding affinities of several Fab fragments were calculated (Lofas & Johnsson, 1990) from association and dissociation rate constants measured using a BIACORE surface plasmon resonance system (Pharmacia Biosensor). A biosensor chip was activated for covalent coupling of gD-mpl receptor using N-ethyl-N'"-(3-dimethylaminopropyl)-carbodiimide hydrochloride (EDC) and N-hydroxysuccinimide (NHS) according to the supplier's (Pharmacia Biosensor) instructions. gD-mpl was buffer-exchanged into 10 mM sodium acetate bufffer (pH 4.5) and diluted to approximately 30 μg/mL. An aliquot (35 μL) was injected at a flow rate of 1 μL/min to achieve approximately 6400 response units (RU) of coupled protein. Finally, 1M ethanolamine was injected as a blocking agent. For kinetics measurements, 1.5 serial dilutions of Fab were injected in PBS/Tween buffer (0.05% Tween-20 in phosphate buffered saline) at 25° C. using a flow rate of 20 gL/min. Equilibrium dissociation constants, $K_d$'s, from SPR measurements were calculated as $k_{off}/k_{on}$. Standard deviations, $s_{on}$ for $k_{on}$ and $s_{off}$ for $k_{off}$, were obtained from measurements with >4 protein concentrations ($k_{on}$) or with >7 protein concentrations ($k_{off}$). Dissociation data were fit to a simple AB→>A+B model to obtain koff +/− s.d. (standard deviation of measurements). Pseudo-first order rate constant (ks) were calculated for each association curve, and plotted as a function of protein concentration to obtain kon +/−s.e. (standard error of fit). The resulting errors e[K] in calculated Kd'"s, were estimated according to the following formula for propagation of errors: $e[K]=[(k_{on})^{-2}(s_{off})^2+(k_{off})^2(k_{on})^{-4}(s_{on})^2]^{1/2}$ where $s_{off}$ and $s_{on}$ are the standard errors in $k_{on}$ and $k_{off}$, respectively.

Example 2

Isolation of Antibodies from the CAT Library

For construction of a library of antibodies displayed of a phage see the following references: WO 92/01047, WO 92/20791, WO 93/06213, WO 93/11236, WO 93/19172, WO 95/01438 and WO 95/15388. Briefly, FIGS. 2 and 3 presents a cartoon of the construction of a phage library containing 6×10$^9$ different clones containing single-chain Fv (scFv) antibodies fused to gene 3 of a phage. Binding selection against an antigen, in this case c-mpl, can be carried out as shown in FIG. 4 and described in greater detail below.

(a) The Antigen

Human c-mpl was cloned as described by F. de Sauvage et al., Nature 369:533 (1994).

(b) Phage Selection on Immunotubes

NUNC immunotubes were coated with 2 ml of a solution of 10 microg/ml of gD-c-mpl in PBS at 4° C. overnight. After rinsing with PBS, tubes were blocked with 3% dry milk in PBS (MPBS) for 2 hr at room temperature. For the first round, 10 μl of C.A.T. antibody phage library containing ~1×10$^{12}$ c.f.u. were added to 1 ml MPBS for blocking for 1 hr at room temperature. Blocked phage were added to coated tubes, and binding of phage to antigen allowed to continue for 2 hr at 37° C. on a rotating wheel. Tubes were washed 6 times with PBS-TWEEN and 6 times with PBS, and phage were then eluted with 100 mM TEA for 10 min at room temperature, neutralized with 500 μl of 1 M TRIS (pH 7.4), and stored on ice until needed. For subsequent rounds, washing was increased to 20 times with PBS-TWEEN, and 20 times with PBS.

Eluted phage were used to infect 5 ml of log phase E. coli TG1 cells and plated on 2YT agar supplemented with 2% glucose and 100 μg/ml carbenicillin. After overnight growth at 30° C., colonies were scraped into 10 ml 2YT. 50 μl of this solution was used to inoculate 25 ml of 2YT with carbenicillin and glucose and incubated, shaking, for two hours at 37° C. Helper phage M13K07 (Pharmacia) were added at an m.o.i. of 10. After adsorption, the cells were pelleted and resuspended in 25 ml of 2YT with carbenicillin (100 μ/ml) and kanamycin (50 μg/ml) and growth continued at 30° C. for 4 hr. E. coli were removed from the phage by centrifugation, and 1 ml of these phage (approx. 10$^{12}$ c.f.u.) were used in subsequent rounds of selection.

(c) Antibody Phage Selection Using streptavidin-coated Paramagnetic Beads

The library was also selected using soluble biotinylated antigen and streptavidin-coated paramagnetic beads (see FIG. 5). gD-c-mpl was biotinylated using IMMUNOPURE NHS-biotin (biotiny-N-hydroxy-succinimide, Pierce) according to manufacturer's recommendations.

For the first round of panning, 10 μl of the phage library were blocked with 1 ml of MPBST (3% dry milk powder, 1×PBS, 0.2% TWEEN 20) for 1 hour on a rotating wheel at room temperature. Biotinylated gD-c-mpl was then added to a final concentration of 100 nM, and phage were allow to bind antigen for 1 hour at 37° C. on a rotator. Meanwhile, 300 μl of DYNABEADS M-280, coated with streptavidin (DYNAL) were washed 3 times with 1 ml MPBST (using a DYNAL Magnetic Particle Concentrator) and then blocked for 2 hr at 37° C. with 1 ml fresh MPBST on a rotator. The beads were then collected with the MPC, resuspended in 50 μl of MPBST, and added to the phage-plus-antigen solution. Mixing continued on a wheel at room temperature for 15 min. The DYNABEADS and attached phage were then washed a total of 7 times: 3 times with 1 ml PBS-TWEEN, once with MPBS, followed by 3 times with PBS. Phage were eluted from the beads by incubating 5 min at room temperature with 300 μl of 100 mM triethylamine. The phage-containing superatant was removed and neutralized with 150 μl of 1M TRIS-HCl (pH 7.4). Neutralized phage were used to infect mid-log TG1 host cells as described above. Plating, induction and harvesting of phage were also as for selection on tubes.

For the second and subsequent rounds of selection on biotinylated gD-c-mpl, 1 ml of harvested phage (approximately 10$^{12}$ cfu) were blocked with 200 μl 10% dry milk, 6×PBS, 0.3% TWEEN 20. Antigen concentration was decreased at each round of selection. In one series the concentrations were: first round, 100 nM; second round, 10 mM; third round, 1 nM. A second panning was performed using: first round 100 nM; second round 100 nM; third round, 50 nM; fourth round, 10 nM; and fifth round, 1 nM. Washing stringency was increased to two cycles of 7 washes for rounds 2, and three cycles for rounds 3 and beyond.

(d) ELISA Screening of Selected Clones

After each round of selection, individual carbenicillin-resistant colonies were screened by ELISA to identify those producing c-mpl-binding phage. Only those clones which were positive in two or more assay formats were further studied. FIG. 6 illustrates the phage ELISA process.

Individual clones were inoculated into 2TY with 2% glucose and 100 μg/ml carbenicillin in 96-well tissue culture plates and grown until turbid. Cultures were then infected at an m.o.i. of 10 with M12KO7 helper phage, and infected cells were transferred to 2YT media containing carbenicillin (100 μg/ml) and kanamycin (50 μg/ml) for growth overnight at 30° C. with gentle shaking.

NUNC MAXISORP microtiter plates were coated with 50 μl per well of gD-c-mpl, BSA, or gD-gp120, at 2 μg/ml in 50 mM carbonate buffer (pH 9.6), at 4° C. overnight. After removing antigen, plates were blocked with 3% dry milk in PBS (MPBS) for 2 hours at room temperature.

Phage cultures were centrifuged and 100 μl of phage-containing supernatants were blocked with 20 μl of 6×PBS /18% dry milk for 1 hour at room temperature. Block was removed from titer plates and blocked phage added and allowed to bind for 1 hour at room temperature. After washing, phage were detected with a 1:5000 dilution of horseradish peroxidase-conjugated anti-M13 antibody (Pharmacia) in MPBS followed by 3',3', 5', 5'-tetramethylbenzidine (TMB). Reactions were stopped by the addition of $H_2SO_4$ and readings taken by subtracting the $A_{405mm}$ from the $A_{450mm}$.

(e) Soluble scFv ELISA

Soluble scFv was induced in the bacterial supernatants of clones by growth in 2YT containing carbenicillin (100 μg/ml) and 1PTG (1 mM) ON at 30° C. ELISA plates were either coated with gD-c-mpl or, for capture ELISA, with anti-c-myc Mab 9E10. Plates were blocked with 1×ELISA diluent (PBS supplemented with 0.5% BSA, 0.05% Tween 20, pH 7.4), and soluble scFv was blocked by adding 20 μl of 6×ELISA dil to 100 μl of supernatant. After binding to antigen coated plates, soluble scFv was detected by adding 50 μl of 1 μg/ml Mab 9E10 per well, followed by horseradish peroxidase-conjugated goat anti-murine Ig, and then TMB as described above. For capture ELISA, soluble scFv was detected by addition of biotinylated c-mpl, followed by streptavidin-peroxidase conjugate and then TMB as above.

The number of clones screened by ELISA from each round, and the number of clones positive by phage ELISA are shown in Table 3.

TABLE 3

Anti-c-mpl scFv antibodies from CAT library

| | |
|---|---|
| Clones screened: | 1534 |
| Clones positive by ELISA: | 361 |
| Clones different by BstNI and sequencing: | 24 |
| Clones that express protein well | 17 |
| clones that are agonists by KIRA: | 9 |
| clones that are agonists by BaF3 proliferation assay: | 6 |
| clones that are agonists by Hu3 proliferation assay: | 4 |

(f) DNA Fingerprinting of Clones

The diversity of c-mpl-binding clones was determined by PCR amplifying the scFv insert using primers pUC19R (5'AGC GGA TAA CAA TTT CAC ACA GG 3') (SEQ. ID. NO: 54) which anneals upstream of the leader sequence and fdtetseq (5'GTC GTC TTT CCA GAC GGT AGT 3') (SEQ. ID. NO: 55) which anneals in the 5' end of gene III, followed by digestion with the frequent-cutting restriction enzyme BstNI (see FIG. 7).

Typical patterns seen after analysis on a 3% agarose gel are shown in FIG. 8.

| DNA Fingerprinting: Protocol | |
|---|---|
| Mix A: | |
| dH20 | 67 μl |
| 10 × ampliTaq buffer | 10 |
| 25 mM MgCl2 | 10 |
| DMSO, 50% | 2 |
| forward primer | 1 |
| Mix B: | |
| 2.5 mM dNTPs | 8 μl |
| AMPLITAQ | 0.5 |
| reverse primer | 1.0 |

Place 90 μl of Mix A in reaction tube

Inoculate with very small portion of *E. coli* colony using a yellow tip

Heat in PCR block to 98° C., 3 min. Remove to ice.

Add 10 μl Mix B

Cycle: 95° C., 30 sec, 55° C. 30 sec, 72° C. 1 min, 20 sec, for 25 cycles, in Perkin Elmer 2400

Remove 10 μl ro run on a 1% agarose gel, test for a 1 kB band

Make remaining mix to 1×BstNI reaction buffer

Add 5 units BstNI

60° C., 2 hours

Electrophorese samples on 3% METAPHORE agarose gel (g) Sequencing of Clones

The nucleotide sequence of representative clones of each fingerprint were obtained. Colonies were inoculated into 50 ml of LB medium supplemented with 2% glucose and 100 μg/ml carbenicillin, and grown overnight at 30° C. DNA was isolated using Qiagen Tip-100s and the manufacturer's protocol and cycle sequenced with fluorescent dideoxy chain terminators (Applied Biosystems). Samples were run on an Applied Biosystems 373A Automated DNA Sequencer and sequences analyzed using the program "Sequencher" (Gene Codes Corporation). The VH and VL genes were assigned to a germline segment using the antibody database, V-BASE.

DNA sequence was obtained for 39 clones and resulted in 24 different c-mpl-binding scFvs.

(h) Purification of scFvs with (his)$_6$

For protein purification of soluble antibody, *E. coli* strain 33D3 was transformed with phagemid DNA. Five ml of 2YT with carbenicillin and glucose was used to grow overnight cultures at 30° C. 0.2 ml of these cultures were diluted into 200 ml of the same media and grown to an $OD_{600}$ of approximately 0.9. The cells were pelleted and resuspended in 250 ml of 2YT containing IPTG (1 mM) and carbenicillin (100 μg/ml) and to induce expression and grown for a further 5 hours at 30° C. Cell pellets were harvested and frozen at −20° C.

The antibodies were purified by immobilized metal chelate affinity chromatography (IMAC). Frozen pellets were resuspended in 10 ml of ice-cold shockate buffer (25 mM TRIS-HCl, 1 mM EDTA, 200 mM NaCl, 20% sucrose, 1 mM PMSF) by shaking on ice for 1 hr. Imidazole was added to 20 mM, and cell debris removed by centrifugation. The supernatants were adjusted to 1 mM $MgCl_2$ and 50 mM phosphate buffer pH 7.5. Ni-NTA agarose resin from Qiagen was used according to the manufacturers instructions. The resin was equilibrated with 50 mM sodium phosphate buffer pH 7.5, 500 mM NaCl, 20 mM imidazole, and the shockate added. Binding occurred in either a batch mode or on a gravity flow column. The resin was then washed twice with 10 bed volumes of equilibration buffer, and twice with buffer containing imidazole increased to 50 mM. Elution of proteins was with 50 mM phosphate buffer pH 7.5, 500 mM NaCl and 250 mM imidazole. Excess salt and imidazole was removed on a PD-10 column (Pharmacia), and proteins were concentrated using a Centricom 10 to a volume of about 1 ml.

Concentration was estimated spectrophotometrically assuming an A280 nm of 1.0=0.6 mg/ml.

Portions of these protein preparations were submitted for KIRA assay, c-mpl-Ba/F3 cell proliferation assay, and Hu3 cell proliferation assay.

(i) Reformatting of Antibodies to scFv with gD tag, Fab', Fab'2, and Full Length Molecules For improved expression of scFv, and for Fab', and Fab'2 forms of antibodies, some of the anti-c-mpl clones were cloned into derivatives of the expression vector pAK19 (Carter et al. METHODS: A companion to Methods in Enzymology. 3:183–192 (1991). Expression is under the transcriptional control of the *E. coli* alkaline phosphatase (phoA) promoter (Chang, et al *Gene* 44:121–125 (1986)) which is inducible by phosphate starvation. Each peptide chain is preceded by the *E. coli* enterotoxin II (stII) signal sequence (Picken, et al.) to direct secretion to the periplasmic space of *E. coli*. This vector also contains the human k$_1$ C$_L$ (Palm et al. *Infect. Immun.* 42:269–275 (1983)) and the human IgG1 C$_H$1 (Ellison, et al Nucleic Acids Res. 10: 4071–4079 (1982)) constant domains. The C$_H$1 gene is immediately followed by the bacteriophage λ t$_O$ transcriptional terminator (Scholtissek and Grosse *Nucleic Acids Res.* 15: 3185 (1987)).

(i) Fab' and Fab'2 Construction

Construction of the Fab' and Fab'2 variants was facilitated by insertion into pAK19 of unique restriction sites at the junctions of the stII and V$_L$ domain (Sfi I), the V$_1$ and Ck domains (Rsr II), the stII and V$_H$ domain (MluI), and the V$_H$ and C$_H$1 domains (Apa I), using oligonucleotide directed mutagenesis. In order to insure expression of monovalent Fab' molecules, the free cysteine at the 3' end of the CH1 domain was mutated to a threonine, these Fab' molecules thus end in the amino acid sequence thr-ala-ala-pro (SEQ ID NO:71), rather than thr-cys-ala-ala (SEQ ID NO:72) as in pAK19. This vector for the expression of Fab' molecules is named pXCA730.

Since some of the antibodies derived from the library had light chains which were derived from lambda rather than kappa light chain families, the human λC$_L$ was subcloned from pB11.2 (Carter, P, Garrard, L., Henner, D. 1991. Methods: A Companion to Methods in Enzymology. 3:183–192) into a derivative of pXCA730 to give vector pXCA970.

For expression of the antibodies as Fab'2 molecules, a vector was constructed which adds the human IgG1 hinge region onto the C$_H$1 domain of pXCA730. This is followed by the yeast GCN4 leucine zipper domain (Hu, et al. *Science* 250:1400–1403 (1990)) for stability. These DNA fragments were constructed using synthesized oligonucleotides and encode the amino acid sequence: cys-pro-pro-cys-ala-pro-glu-leu-leu-gly-gly-arg-met-lys-gln-leu -glu-asp-lys-val-glu-glu-leu-leu-ser-lys-asn-tyr-his-leu-glu-asn-glu-val-ala-arg-leu-lys-lys-leu-val-gly-glu-arg (SEQ. ID. NO: 56). The resultant plasmid is named pXCA740.

The variable domains of the scFvs were amplified and restriction sites added for subcloning into the vectors described above by the PCR technique. Specific oligonucleotides were designed for each V$_H$ or V$_H$ region as shown below.

```
12B5, 12D5, and 10D10 Light chain variable domains:

5' primer
GCT TCT GCG GCC ACA CAG GCC TAC GCT GAC ATC GTG ATG ACC C (SEQ. ID. NO: 57)

3' primer
ATG ATG ATG TGC CAC GGT CCG TTT GAT CTC CAG TTC GGT C (SEQ. ID. NO: 58)

12E10 Light chain variable domain:

5' primer
GCT TCT GCG GCC ACA CAG GCC TAC GCT TCC TAT GTG CTG ACT C (SEQ. ID. NO: 59)

3' primer
CCT TCT CTC TTT AGG TTG GCC AAG GAC GGT CAG CTT GGT C (SEQ. ID. NO: 60)

10F6 Light chain variable domain

5' primer
GCT TCT GCG GCC ACA CAG GCC TAC GCT CAG TCT GTG CTG ACT C (SEQ. ID. NO: 61)

3' primer
CCT TCT CTC TTT AGG TTG GCC AAG GAC GGT CAG CTT GGT C (SEQ. ID. NO: 60)

12B5 Heavy chain variable domain

5' primer
CAT TCT ACA AAC GCG TAC GCT CAG GTG CAG CTG GTG CAG (SEQ. ID. NO: 62)

3' primer
GTA AAT GTA TGG GCC CTT GGT GGA GGA GGC ACT CGA GAC GGT GAC (SEQ. ID. NO: 63)

12D5 Heavy chain variable domain

5' primer
CAT TCT ACA AAC GCG TAC GCT CAG-GTG CAG CTG GTG GAG (SEQ. ID. NO: 64)

3' primer
```

```
                                    -continued
GTA AAT GTA TGG GCC CTT GGT GGA GGA GGC ACT CGA GAC GGT GAC (SEQ. ID. NO: 63)
```

10D10 Heavy chain variable domain

5' primer
```
CAT TCT ACA AAC GCG TAC GCT GAC GTG CAG CTG GTG CAG (SEQ. ID. NO: 65)
```

3' primer
```
GTA AAT GTA TGG GCC CTT GGT GGC GGC TGA GGA GAC GGT GAC (SEQ. ID. NO: 66)
```

12E10 Heavy chain variable domain

5' primer
```
CAT TCT ACA AAC GCG TAC GCT CAG GTG CAG CTG CAG CAG (SEQ. ID. NO: 67)
```

3' primer
```
GTA AAT GTA TGG GCC CTT GGT GGA GGA GGC ACT CGA GAC GGT GAC (SEQ. ID. NO: 63)
```

10E6 Heavy chain variable domain

5' primer
```
CAT TCT ACA AAC GCG TAC GCT CAG GTG CAG CTG CAG GAG (SEQ. ID. NO: 68)
```

3' primer
```
GTA AAT GTA TGG GCC CTT GGT GGA GGC TGA AGA GAC GGT AAC (SEQ. ID. NO: 69)
```

PCR reactions were carried out using 100 ng of plasmid DNA containing the scFv, 0.5 μM of the appropriate 5' and 3'primer, 200 μM each dNTP, 10 mM KCl, 6 mM(NH$_4$)$_2$SO$_4$, 20 mM TRIS-HCl, pH 8.0, 2 mM Mg/cl$_2$, 1% Triton X-100, 100 μM BSA and 2.5 units of Pfu DNA polymerase (Stratagene). Amplification was for 30 cycles of: 30 sec at 95° C., 30 sec at 55° C., 30 sec at 72° C.After digestion with the appropriate restriction enzymes, the reaction products were separated by agarose gel electrophoresis and the approximately 350 bp band was isolated using a Gene Clean II kit (BIO 101, Vista, Calif.). The fragments for the light chain variable regions were ligated into the vectors previously digested with Sfi I and Rsr II for the kappa isotypes, or Sfi I and Msc I for the lambda isotypes, and transformed into E. coli DH5a. Desired recombinants were identified using restriction enzyme analysis and sequenced to confirm the presence of the desired fragments. The heavy chain variable domains were then cloned similarly into the plasmids containing the light chains using the restriction enzymes Mlu I and Apa I, and the final constructions were again checked by DNA sequencing.

(k) Construction of scFv With gD Tags

For increased and regulated expression in high density fermentation tanks, the Sfi I to Not I fragments of the scFv forms of p12B5, p12D5, p10F6, and p12E10 were subcloned into a derivative of pAK19 containing the phoA promoter and stII signal sequence rather than the lacZ promoter and hybrid signal sequence of the original library. For ease of purification, a DNA fragment coding for 12 amino acids (met-ala-asp-pro-asn-arg-phe-arg-gly-lys-asp-leu) (SEQ. ID. NO: 70) derived from herpes simplex virus type 1 glycoprotein D (Lasky and Dowbenko DNA (N.Y.) 3:23–29 (1984.)) was synthesized and inserted at the 3' end of the V$_L$ domain in place of the (his)$_6$ and c-myc epitope originally present in the C.A.T. library clones.

(l) Exyression in E. coli

Plasmids containing genes for scFv-gD, Fab' or Fab'2 molecules were expressed in E. coli strain 33B6 (W3110 DfhuA phoADE15 deoC2 ilvG2096(val$^R$) degP41(DPstI-Kan$_R$) D(argF-lac)169 IN(rrnD-rrnE)1) grown for approximately 40 hr at 30° C. in an aerated 10-liter fermentor as described previously (Carter et al Bio/Technology 10:163–167(1992.)).

Example 3

Cloning and Expression of Full Length Human Antibody Derivatives of 12B5, 12D5, and 12E10.

For expression of full length antibodies in mammalian cells, the heavy chain variable domains were subcloned from the Fab constructs into a derivative of expression vector pRK (Suva et al., Science 237:893–896 (1987)) which contains the human IgG1 CH1, CH2, and CH3 domains and a human antibody signal sequence (Carter et al., Proc. Natl. Acad. Sci. USA. 89:4285–4289 (1992)). The light chain was cloned into a separate pRK plasmid. The light and heavy chain expression vectors were cotransfected into adenovirus-transformed human embryonic kidney cell line 293 by a high-efficiency procedure (Gorman et al., DNA Protein Eng. Technol. 2:3–10 (1990)). Harvested conditioned media was shown to contain anti-mpl antibody by ELISA.

For production of a more stable cell line and high-level antibody production, the light and heavy chains were moved into the SVI.DI expression vector previously described (Lucas et al., Nucleic Acids Res. 24: 1774–1779 (1996)). This vector contains the mouse DHFR cDNA in the intron of the expression vector pRK and allows for amplification of expression by selection in methotrexate The light chain is cloned into the same plasmid with expression driven by a second SV40 promoter/ enhancer. The plasmid was linearized and transfected into CHO cells using lipofectamine (Gibco-BRL) following manufacturer's instructions. Seven to ten days after transfer to selective medium, clones were isolated into 96 well plates for later study, or pooled and expanded for culture in roller bottles.

Conditioned media for purification of the antibodies was generated in roller bottles. Cells were seeded into the roller bottles at an initial cell density of 2×107 cells in 200 ml rich medium (DMEM: Ham's F12 (1:1) supplemented with 5% fetal bovine serum. At approximately 80% confluency, the media was replaced with serum-free PS-24 production medium supplemented with insulin (10 jig/ml), transferrin (10 μg/ml), trace elements and lipid alcohol. Conditioned media was harvested after 10 days.

Example 8

Purification of Agonist Antibodies (a) Purification of scFv With gD Tag

Frozen cell paste was resuspended at 1 gm/ml TE (25 mM TRIS, 1 mM EDTA, pH 7.4) and gently agitated 18 hr on ice. Cell debris was removed by centrifugation at 10,000×g for 30 min. The supernatant was loaded onto an affinity column (2.5×9.0 cm) consisting of an anti-gD monoclonal antibody 5B6 (Paborsky, L. R. et al., *Protein Eng.* 3: 547–553 (1990)) coupled to CNBr SEPHAROSE which had been equilibrated with PBS. The column was washed 18 hr with PBS, and then washed with PBS containing 1 M NaCl until the absorbance of the column effluent was equivalent to baseline. All steps were done at 4° C. at a linear flow rate of 25 cm/hr. Elution was performed with 0.1 M acetic acid, 0.5 M NaCl, pH 2.9. Column fractions were monitored by absorbance at 280 nm and peak fractions pooled, neutralized with 1.0 M TRIS, pH 8.0, dialyzed against PBS, and sterile filtered. The resultant protein preparations were analyzed by non-reducing SDS-PAGE.

(b) Purification of Fab' Molecules

For purification of Fab' molecules, 5 g of frozen cell paste was resuspended in 5 ml of TE (25 mM TRIS, 1 mM EDTA, pH 7.4) and gently stirred 18 hr on ice. The pH of the shockate was adjusted to 5.6 with 2 M HCl and the precipitate and cell debris removed by centrifugation at 10,000×g for 30 min. The supernatant was loaded onto a 1 ml BAKERBOND ABx column (0.5×5.0 cm) (J. T. Baker, Phillipsburg, N.J.) pre-equilibrated with 20 mM MES, pH 5.5. After washing with 20 mM MES to baseline, the Fab' was eluted using a 10 ml linear gradient from 0 to 100% of 20 mM NaOAc, 0.5 M $(NH_4)_2SO_4$, pH 7.2, with a flow rate of 153 cm/hr. Fractions containing Fab' were pooled, and buffer exchanged into PBS.

(c) Purification of Fab'2 Molecules

Frozen cell paste (100 gm) was thawed into 10 volumes of 25 mM TRIS, 5 mM EDTA, 1 mM NaN3, pH 7.4 and disrupted by three passages through a microfluidizer (TECH-MAR). PMSF was added to 1 mM and the cell debris removed by centriftigation at 10,000×g for 30 min. The supernatant was filtered sequentially through a 0.45 $\mu$m, and a 0.2 $\mu$m SUPORCAP filter (Gehnan), and loaded onto a 50 ml SEPHAROSE-fast-flow Protein-G column (Pharmacia) pre-equilibrated with PBS. After washing to baseline with PBS, Fab'2 was eluted with 0.1 M glycine ethyl ester, pH 2.3, into tubes with contained 1/10 volume of 1 M TRIS, pH 8.0. Fractions containing Fab'2 were pooled and concentrated by Ultrasette with a 30 kilodalton molecular weight cut off, and buffer exchanged into 20 mM NaOAc, 0.01% octylglucoside, pH 5.5. This material was loaded onto a 30 ml S-SEPHAROSE column (Pharmacia) pre-equilibrated with 20 mM NaOAc, washed to baseline with 20 mM NaOAc, pH 5.5, and eluted with a linear gradient of 0–1 M NaCl in 25 mM NaOAc over 10 column volumes. Fractions containing Fab'2 were pooled and buffer exchanged to PBS.

(d) Purification of Full Length Antibodies From Transfected CHO Cell Supernatants Conditioned medium harvested from roller bottles was loaded onto a 5 ml Protein-A SEPHAROSE column (1.0× 5.0 cm) pre-equilibrated with PBS, washed with PBS, and then washed to baseline with PBS containing 1 M NaCl. Antibody was eluted with 0.1 M HOAc, 0.5 N NaCl, pH 2.9, neutralized with 1 M TRIS, and buffer exchanged to PBS.

A summary of agonist antibody activities for several antibodies and fragments thereof is shown in Table 4 below.

Plasmid DNA for each of the antibodies 12B5, 12D5, 12E10, 10D10, 10F6 and 5E5 have been made, under Budapest Treaty conditions at the American Type Culture Collection, 1080 University Blvd., Manassas, Va. 20110–2209. All restrictions on access to the deposits will be irrevocably removed upon the grant of a first United States patent based on this application. The ATCC deposit numbers are as follows:

12B5-203125
12D5-203121
12E10-203120
10D10-203124
10F6-203122
5E5-203123

Summary of Mpl Agonist Antibody Activities

| Antibody | Hu3 Proliferation (ED50) | KIRA (ED50) | Hu3 binding (IC50) | Mpl/TPO ELISA (IC50) | Platelets (IC50) | MK assay |
|---|---|---|---|---|---|---|
| 12B5 | | | | | | |
| scFv | 20 pM | 1 nM | 10 nM | 17 nM | 100 nM | ++ |
| Fab | >1 $\mu$M | 3 nM | 900 nM | none >1 | $\mu$M | – |
| Fab'2 | 5 pM | 1 nM | 5 nM | 1 nM | 300 nM | + |
| IgG | 30 pM | 400 pM | 10 nM | 152 pM | 300 nM | – |
| 12E10 | | | | | | |
| scFv | 5 pM | 60 pM | 5 nM | 1.6 nM | 5 nM | |
| Fab | >1 $\mu$M | >1 $\mu$M | 500 nM | 180 nM | >1 $\mu$M | |
| Fab'2 | >1 $\mu$M | 160 pM | 10 nM | 640 pM | 500 nM | |
| IgG | >1 $\mu$M | 480 pM | 50 nM | 450 pM | 500 nM | |
| 12D5 | | | | | | |
| scFv | 1.2 nM | 280 pM | 10 nM | 24 nM | >1 $\mu$M | |
| Fab | >1 $\mu$M | 4 nM | 500 nM | 1 $\mu$M | >1 $\mu$M | |
| Fab'2 | 4.8 pM | 600 pM | 4 nM | 1 nM | 100 nM | + |
| IgG | >1 $\mu$M | 3 nM | 10 nM | 450 pM | 500 nM | |

Example 9

In another embodiment, the invention provides a method of selecting an antibody which binds to and dimerizes a receptor protein. In this method, a library of antibodies is panned using a receptor protein having two protein subunits as the binding target. The library is panned as described above for mpl agonist antibodies. Preferably, the antibodies are human and more preferably monoclonal. The library is conveniently a library of single chain antibodies, preferably displayed on the surface of phage. The display of proteins, including antibodies, on the surface of phage is well known in the art as discussed above and these known methods may be used in this invention. Antibody libraries are also commercially available, for example, from Cambridge Antibody Technologies (CAT), Cambridge, UK. Preferably, the antibody selected by the method of the invention activates the receptor by dimerizing the receptor and thereby achieves an effector result similar to the effector result generated when the natural endogenous ligand for the receptor binds the receptor.

The method of the invention can be used to find agonist antibodies to any receptor having two components which is known and /or can be cloned. It is not necessary to know the primary, secondary or tertiary structure of the receptor protein, although this information is useful for cloning, etc., since the method of the invention allows selection of antibodies which will bind any displayed receptor which is activated by dimerization. Many known receptor proteins are activated by dimerization and any of these known receptors may be used in the invention. Suitable receptors include tyrosine kinase receptors and hematopoietic receptors that lack kinase activity.

Activation of a receptor such as a tyrosine kinase receptor by a scFv is an unexpected result. Current understanding of receptor activation argues that for many classes of receptors, including tyrosine kinase receptors and hematopoietic cytokine receptors that lack intrinsic tyrosine kinase activity (but associate with intracellular kinases), it is a dimerization event mediated by a ligand that is the key event in receptor activation. This view is supported by crystal structures of receptor ligand complexes as well as the demonstrated agonist ability of certain monoclonal antibodies (but not the Fab" fragments of these antibodies). A single chain antibody would not, therefore, be expected to be able to cause receptor dimerization and activation.

MuSK is a recently identified tyrosine kinase localized to the postsynaptic surface of the neuromuscular junction. (Valenzuela et. al.1995. Neuron 15 573–584.) Mice made deficient in MuSK fail to form neuromuscular junctions (Dechiara et. al.1996. Cell 85 501–512.), a phenotype highly similar to that observed in mice lacking the nerve derived signaling molecule agrin (Gautam et. al., 1996, Cell 85 525–535). The likely involvement of MuSK in agrin signaling is strengthened by the observations that agrin induces the rapid tyrosine phosphorylation of MuSK and that labeled agrin can be chemically crosslinked to MuSK (Glass et. al., 1996, Cell 85 513–523.).

Formation of the neuromuscular junction is achieved through a process that includes the differentiation of membrane on the muscle fiber proximal to the neuron terminus and changes in gene expression within the nuclei proximal to this junction (reviewed by Bowe et. al., 1995, Annu-Rev-Neurosci. 18 443–462 and Kleiman et. al., 1996, Cell 85 461–464.). A striking feature of this complex process is the redistribution and concentration of AChRs within the myotube membrane. Agrin is able to the induce this clustering of AChRs as well as changes in the extracellular matrix and cytoskeletal components of the synaptic apparatus (Bowe et. al., supra; Godfrey et. al.,1984, J. Cell Biol. 99 615–627; Nitkin et. al.,1987, J. Cell Biol. 105 2471–2478). Agrin is a secreted protein with a core molecular weight of ~200 kDa that contains several copies of EGF repeats, laminin-like globular domains and sequences that resemble protease inhibitors. It is released by motor neuron terminals and maintained within the basil lamina of the synaptic cleft. While agrin apparently does not to bind MuSK with high affinity (Glass et. al., supra), it has been reported to interact with other molecules present at the neuromuscular junction, most notably alpha-dystroglycan (O'Toole et. al., 1996,. Natl. Acad. Sci. USA 93 7369–7374) thereby complicating the analysis of MuSK's role in the signaling events initiated by agrin.

Antigen specific scFv, identified by panning a diverse library of scFv expressed, for example, on M13 phage provide a source of molecules capable of mediating specific therapeutic activities, and offer a rapid new approach to study the function of novel or recently identified molecules such as MuSK. scFv are identified below that mediate receptor activation and that direct MuSK activation induces changes in AChR distribution and tyrosine phosphorylation similar to that observed with agrin. The induction of AChR clustering and tyrosine phosphorylation by scFv antibodies provides direct evidence to support conclusions drawn from studies of knockout mice deficient in MuSK indicating this recently discovered tyrosine kinase acts to induce key events in the formation of the neuromuscular junction. As a potential signal transducer of agrin, it is noteworthy that MuSK does not display high affinity binding to agrin, leading to speculation that there must be an additional agrin binding component(s) involved in mediating the agrin signal . The molecular nature of this component is unknown. It is interesting that it is possible to induce the receptor clustering, the hallmark activity of agrin, with an agent directed specifically to MuSK.

The marked upregulation of MuSK expression in muscle following denervation or muscle immobilization as well as the chromosomal localization of MuSK within a region associated with fukiyama muscular dystrophy point to an important role for this molecule in regulation of the neuromuscular junction (Valenzuela et.al., supra) and indicates the possibility that therapeutic benefit is possible through the controlled regulation of MuSK activity. As agrin is expressed not only at the neuromuscular junction, but in a wide variety of peripheral and central neurons (Bowe et. al., supra; Rupp et. al., 1991, Neuron 6 811–823; Tsim et. al., 1992, Neuron 8 677–689) it may not be an optimal candidate molecule through which to manipulate MuSK function as exogenously introduced agrin derivatives might elicit consequences not restricted to the neuromuscular junction. Thus, in comparison, the ability to obtain direct activation of MuSK through scFv offers an attractive alternative. Each of the scFv that were tested displayed affinity for MuSK in the nM range demonstrating the utility of phage displayed scFv libraries as a rich source of high affinity and highly specific molecules.

The antibodies of the invention are, therefore, useful in assaying the upregulation of MuSK receptors in sample tissues to determine the degree of neuromuscular damage associated with this upregulation. The antibodies are also useful for activating the MuSK receptor and inducing AChR clustering at neuromuscular junctions as a direct result of the agonist properties of these antibodies. Administration of the antibodies to a person suffering from denervation or muscle immobilization , e.g. muscular dystrophy, provides a method of improving the function of the neuromuscular junctions in these people.

To prepare scFv having agonist activity, antibodies were selected which induce a proliferative response in a factor dependent cell line through a chimeric MuSK-Mpl receptor comprised of the extracellular domain of MuSK and the intracellular domain of the hematopoietic cytokine receptor c-Mpl (the receptor for thrombopoietin, TPO). Activation of c-Mpl is believed to require homodimerization, as is the case for the growth hormone receptor, the erythropoietin receptor and other related receptors of this class (Carter et. al., 1996, Annu-Rev-Physiol 58 187–207; Gurney et. al., 1995, Proc .Natl. Acad. Sci. USA 92 5292–5296). Ba/F3 cells expressing MuSK-Mpl were starved of IL-3 and exposed to a range of concentrations of each scFv expressed as soluble protein. Surprisingly, 4 of the 21 scFv were able to induce a robust proliferative response in the MuSK-Mpl expressing cells (FIG. 11). This activity was observed at nM concentrations of scFv. The scFv were without effect on the parental, untransfected Ba/F3. Agonist activity was also present among those IgG that were derived from agonist scFv but was not noted among IgG derived from non-agonist scFv. Soluble agrin c-terminal domain (c-agrin) was without effect supporting previous observations that agrin does not bind MuSK directly. The c-terminal domain of agrin is known to contain the AChR clustering activity of agrin and is essential for neuromuscular junction formation (Ruegg et. al., 1992, Neuron 8 691–699; Tsim et. al., supra). The $EC_{50}$ for the ability to induce proliferation was 5 nM for the most active agonist clone when expressed as either scFv or IgG. The affinity of these scFv and IgG for MuSK was determined using BIAcore™ analysis. The agonist scFv and several non-agonist scFv each displayed affinity for MuSK within the range of 5–25 nM. In contrast, the affinities of the IgG for MuSK were 10–30 pM . See Table 5 below.

TABLE 5

| clone # | Agonist | $k_d$. | $k_a$ | Affinity |
|---|---|---|---|---|
| musk #2-scFv | + | $3.34 \times 10^{-3}$ | $8.78 \times 10^5$ | 3.8 nM |
| musk #3-scFv | − | $2.39 \times 10^{-3}$ | $1.05 \times 10^5$ | 23 nM |
| musk #4-scFv | + | $1.57 \times 10^{-3}$ | $1.84 \times 10^5$ | 8.5 nM |
| musk #5-scFv | − | $2.49 \times 10^{-3}$ | $5.29 \times 10^5$ | 4.7 nM |
| musk #6-scFv | − | $4.95 \times 10^{-3}$ | $1.05 \times 10^5$ | 4.7 nM |
| musk #13-scFv | + | $2.32 \times 10^{-3}$ | $4.53 \times 10^5$ | 5.1 nM |
| musk #22-scFv | + | $6.09 \times 10^{-3}$ | $1.27 \times 10^5$ | 4.8 nM |
| musk #13-IgG | + | $1.01 \times 10^{-5}$ | $8.05 \times 10^5$ | 12.5 pM |
| musk #22-IgG | + | $4.86 \times 10^{-5}$ | $1.65 \times 10^6$ | 29.5 pM |

To probe this agonist activity further, scFv were examined for the ability to induce tyrosine phosphorylation of full length MuSK tyrosine kinase. The murine myoblastic cell line C2C12 was cultured under conditions that promote myotube differentiation and subsequently exposed to scFv, IgG or c-agrin. In correspondence with previous data (Glass et. al., supra), c-agrin was able to induce MuSK tyrosine phosphorylation. The agonist scFv and IgG were also found to rapidly induce tyrosine phosphorylation of MuSK as determined by western blot analysis with anti-phosphotyrosine antibody whereas other scFv and non-agonist anti-MuSK IgG were without effect. The ability of the scFv MuSK agonists to induce AChR clustering in cultured C2C12 myotubes was examined.

Following stimulation, the cells were fixed and the distribution of cell surface AChR was revealed with rhodamine labeled bungarotoxin. In undifferentiated myoblasts, AChR were dispersed and unfocused in the presence of c-grin, scFv, or IgG. In contrast, upon myotube differentiation, c-agrin and agonist scFv and IgG induced marked aggregation of AChR into large and intensely stained clusters. Non-agonist scFv and non-agonist IgG directed against MuSK or an irrelevant antigen were without effect. An additional consequence of agrin action, tyrosine phosphorylation of subunits of the AChR was also examined utilizing an antisera that recognizes the δ and γ chains of the receptor. Tyrosine phosphorylation levels of both the δ and γ chains were markedly induced by c-agrin as well as the agonist scFv and agonist IgG but were unaffected by control scFv and IgG.

Variants of the MuSK agonist antibodies of the invention may be prepared as described above for thrombopoietic antibodies.

Construction of expression vectors. Coding sequence for murine MuSK was obtained by PCR amplification. MuSK-Fc was prepared by fusion of the extracellular domain of MuSK (a.a. 1–492) in frame with the Fc region of human IgG1 in the eukaryotic expression vector pRK5tkNEO. MuSK-Fc was transiently expressed in 293 cells and purified over a protein G column. A chimeric receptor, MuSK-Mpl, comprised of the extracellular domain of MuSK (amino acids 1–492) and the transmembrane and intracellular domain of the human c-Mpl receptor (amino acids 491–635) was prepared by sequential PCR and cloned into pRK5tkNEO. Stable cell lines expressing the chimeric receptor were obtained by electroporation (5 million cells, 250 volts, 960 μF) of linearized vector (20 μg) into Ba/F3 cells followed by selection for neomycin resistance with 2 mg/ml G418. Full length MuSK in pRK5tkNEO was transfected into 293 cells and stable transformants were obtained following two weeks of G418 selection (400 μg/ml). The sequence of the DNA constructs were confirmed by DNA sequencing. Expression of MuSK was assessed by flow cytometry analysis as described below. Ba/F3 cells were maintained in RPMI 1640 media supplemented with 10% fetal calf serum and 5% conditioned media from WEHI-3B cells as source of IL-3. C-agrin (amino acids 1137–1949 of the rat agrin (Ag +8 active splice form (Ferns et al., 1993, *Neuron* 11 491–502.)) was expressed by transient transfection from 293 cells in serum free media with an expression vector, pRK-gD-c-Agrin, as a fusion protein with the gD signal sequence and epitope tag and a genenase cleavage site (MGGAAARLGAVILFVVIVGLHGVRGKYALADASL KMADPNRFRGKDLPVLDQLLEGGAAHYALLPG) (SEQ ID NO:73) fused to the N-terminus.

Isolation of scFv and IgG MuSK-Fc immunoadhesin was coated on Maxisorp tubes (Nunc) at 10 μg/ml. A library of human scFv (Cambridge Antibody Technology, England) was panned through two rounds of enrichment essentially as described (Griffiths et al., 199, *EMBO-J* 12 725–734). The specificity of individual clones was assessed first by elisa (Griffiths et al., supra) using MuSK-Fc and a control immunoadhesin (CD4-Fc). Positive clones were screened by PCR and "fingerprinted" by BstN1 digestion (Clackson et al., 1991, *Nature* 352 642–648.). Examples of clones with unique patterns were sequenced and subjected to FACS analysis with cells expressing or not expressing MuSK. For FACS analysis, cells ($10^5$) were incubated for 60 minutes at 4 C. in 200 μl 2% FBS/PBS (fetal bovine serum/phosphate buffered saline) with $10^{10}$ phage that were first blocked by incubation in 30 μl 10% FBS/PBS. Cells were then washed with 2% FBS/PBS, stained with anti-M13 antibody (Pharmacia, Piscataway N.J.) and R-phycoerythrin-conjugated donkey anti-sheep antibody (Jackson Immunoresearch, West Grove Pa.), and analyzed by FACS analysis. ScFv were expressed in bacteria as epitope tagged proteins containing a c-myc tag sequence recognized by monoclonal antibody 9E10 (Griffiths et al., supra)and a polyhistidine tail ($his_6$) and were purified over Ni-NTA column with imidazole elution as recommended by manufacturer (Qiagen). For expression of clones as IgG the sequences encoding the $V_H$ and $V_L$ regions of the scFv were introduced by PCR into mammalian expression vector pIgG-kappa which was designed to enable the expression of fully human light and heavy chains of kappa type IgG. Expression vectors for the individual clones were transfected into CHO cells and IgG were harvested from conditioned serum free media and purified over a protein A column.

Proliferation assays. Cells were cultured in the absence of IL-3 for twenty-two hours (in RPMI supplemented with 10% FBS). Cells were then washed twice with RPMI and plated in 96 well dishes at 50,000 cells per well in 0.2 ml of 7.5% FBS RPMI supplemented with the indicated concentrations of scFv or IgG. Each concentration was tested in duplicate. After an incubation of sixteen hours, 1 μCi of [$^3$H]-thymidine was added per well and incubation was continued for an additional six hours. Incorporation of [$^3$H]-thymidine was measured with a Top Count Counter (Packard Instruments, CA).

AChR clustering assay. C2C12 were maintained in 10% FBS in high glucose DMEM at subfluency. For AChR clustering assays C2C12 were seeded on glass slides coated with fibronectin and poly-lysine and myotube differentiation was induced by 48 hour incubation in 2% horse serum high glucose DMEM. scFv or c-agrin were added to the culture medium and incubated overnight (16 hours). Cells were then washed with PBS and fixed in 4% paraformaldehyde.

Rhodamine conjugated bungarotoxin (Molecular Probes, Eugene Oreg.) was used to reveal the localization of AChRs as described (Ferns et al, supra).

Binding affinity analysis. Protein interaction analysis using BIAcore™ instruments was performed as described (Mark et al, 1996, *J. Biol. Chem.* 271 9785–9789). Briefly, research grade CM5 sensor chips were activated by injection of 20 μl of 1:1 1 N-Ethyl-N'-(3-dimethylaminopropyl) carboiimide hydrochloride and N-hydroxysuccinimide at 5 μl/min flow rate. 20 μl of MuSK-Fc at 20 μg/min in 10 mM sodium acetate, pH 5.0 was injected over the sensor chip, followed by 30 μl of ethanolamine. scFv or IgG were purified and concentrations determined by Pearce BCA kit. Thirty μl protein samples in PBS with 0.05% Tween 20 were injected at a flow rate of 10 μl/min by the Kinject method. Proteins were allowed to dissociate for 20 min in a flow of PBS with 0.05% Tween 20. Sensorgrams were analyzed with BIAevaluation 2.1 software from Pharmacia Biosensor AB. Apparent dissociation rate constants ($k_d$) and association rate constants ($k_a$) were obtained by evaluating the sensorgram with A+B=AB type I fitting. Equilibrium dissociation constant $K_d$ was calculated as $k_d/k_a$.

Immunoprecipitation and Western Blot Analysis. C2C12 were maintained in 10% FBS high glucose DMEM and induced to differentiate by 72 hour incubation in 2% horse serum. Cells were then stimulated by addition of c-agrin, scFv or IgG for the time indicated in the figures. ScFv and IgG were used at 50 nM. The c-agrin containing conditioned media was used at level that provided maximal tyrosine phosphorylation. Cell extracts were prepared as described (Gurney et al., supra). Extracts were incubated for 60 minutes at 4 C. with 30 μl agarose conjugated antiphosphotyrosine monoclonal antibody 4G10 (UBI inc., Lake Placid N.Y.) or 1 μg of anti-MuSK IgG #13 followed by 30 μl protein A sepharose beads. Western blot analysis with antiphosphotyrosine antibody 4G10 or anti AChR antibody (Affinity Bioreagents, Golden Conn.) was performed as recommended by the manufacturer and revealed with HRP conjugated secondary antibody and ECL (Amersham).

MuSK scFv are readily observed as dimers when resolved by nondenaturing gel electrophoresis. Additionally, the abundance of dimeric species may be significantly altered in the local context of scFv bound to receptor on the cell surface. Alternatively, screening an scFv phage library with a divalent antigen, in this case MuSK-Fc, allows direct selection of scFv that bind to and facilitate the formation of a receptor dimer.

While the invention has necessarily been described in conjunction with preferred embodiments and specific working examples, one of ordinary skill, after reading the foregoing specification, will be able to effect various changes, substitutions of equivalents, and alterations to the subject matter set forth herein, without departing from the spirit and scope thereof. Hence, the invention can be practiced in ways other than those specifically described herein. It is therefore intended that the protection granted by letters patent hereon be limited only by the appended claims and equivalents thereof.

All references cited herein are hereby expressly incorporated by reference.

What is claimed is:

1. An agonist antibody, or fragment thereof which binds to human c-mpl, wherein said antibody or fragment thereof comprises an amino acid sequence which is selected from the group consisting of 12E10 (SEQ ID NO:79), 12B5 (SEQ ID NO:77), 10F6 (SEQ ID NO:74) and 12D5 (SEQ ID NO:78).

2. An agonist antibody, or fragment thereof which binds to human c-mpl which is selected from the group consisting of Ab1, Ab2, Ab3, Ab4, Ab5 and Ab6, wherein each Ab1–Ab6 comprises a VH and VH chain, each VH and VL chain comprising CDR amino acid sequences designated CDR1, CDR2 and CDR3 separated by framework amino acid sequences, the amino acid sequence of each CDR in each VH and VL chain of Ab1–Ab6 is selected according to the following table:

| Ab1: | $VH^{CDR1}$ | $VH^{CDR2}$ | $VH^{CDR3}$ |
|---|---|---|---|
| | (SEQ ID NO: 1) | (SEQ ID NO: 3) | (SEQ ID NO: 5) |
| | (SEQ ID NO: 2) | (SEQ ID NO: 4) | (SEQ ID NO: 6) |
| | $VL^{CDR1}$ | $VL^{CDR2}$ | $VL^{CDR3}$ |
| | (SEQ ID NO: 7) | (SEQ ID NO: 9) | (SEQ ID NO: 11) |
| | (SEQ ID NO: 8) | (SEQ ID NO: 10) | (SEQ ID NO: 12) |
| Ab2: | $VH^{CDR1}$ | $VH^{CDR2}$ | $VH^{CDR3}$ |
| | (SEQ ID NO: 13) | (SEQ ID NO: 15) | (SEQ ID NO: 17) |
| | (SEQ ID NO: 14) | (SEQ ID NO: 16) | (SEQ ID NO: 18) |
| | $VL^{CDR1}$ | $VL^{CDR2}$ | $VL^{CDR3}$ |
| | (SEQ ID NO: 19) | (SEQ ID NO: 21) | (SEQ ID NO: 23) |
| | (SEQ ID NO: 20) | (SEQ ID NO: 22) | (SEQ ID NO: 24) |
| Ab3: | $VH^{CDR1}$ | $VH^{CDR2}$ | $VH^{CDR3}$ |
| | (SEQ ID NO: 25) | (SEQ ID NO: 27) | (SEQ ID NO: 29) |
| | (SEQ ID NO: 26) | (SEQ ID NO: 28) | (SEQ ID NO: 30) |
| | $VL^{CDR1}$ | $VL^{CDR2}$ | $VL^{CDR3}$ |
| | (SEQ ID NO: 19) | (SEQ ID NO: 21) | (SEQ ID NO: 23) |
| | (SEQ ID NO: 20) | (SEQ ID NO: 22) | (SEQ ID NO: 24) |
| Ab4: | $VH^{CDR1}$ | $VH^{CDR2}$ | $VH^{CDR3}$ |
| | (SEQ ID NO: 25) | (SEQ ID NO: 31) | (SEQ ID NO: 33) |
| | (SEQ ID NO: 26) | (SEQ ID NO: 32) | (SEQ ID NO: 34) |
| | $VL^{CDR1}$ | $VL^{CDR2}$ | $VL^{CDR3}$ |
| | (SEQ ID NO: 35) | (SEQ ID NO: 21) | (SEQ ID NO: 23) |
| | (SEQ ID NO: 20) | (SEQ ID NO: 22) | (SEQ ID NO: 24) |
| Ab5: | $VH^{CDR1}$ | $VH^{CDR2}$ | $VH^{CDR3}$ |
| | (SEQ ID NO: 36) | (SEQ ID NO: 38) | (SEQ ID NO: 40) |
| | (SEQ ID NO: 37) | (SEQ ID NO: 39) | (SEQ ID NO: 41) |
| | $VL^{CDR1}$ | $VL^{CDR2}$ | $VL^{CDR3}$ |
| | (SEQ ID NO: 19) | (SEQ ID NO: 21) | (SEQ ID NO: 23) |
| | (SEQ ID NO: 20) | (SEQ ID NO: 22) | (SEQ ID NO: 24) |
| Ab6: | $VH^{CDR1}$ | $VH^{CDR2}$ | $VH^{CDR3}$ |
| | (SEQ ID NO: 42) | (SEQ ID NO: 44) | (SEQ ID NO: 46) |
| | (SEQ ID NO: 43) | (SEQ ID NO: 45) | (SEQ ID NO: 47) |
| | $VL^{CDR1}$ | $VL^{CDR2}$ | $VL^{CDR3}$ |
| | (SEQ ID NO: 48) | (SEQ ID NO: 50) | (SEQ ID NO: 52) |
| | (SEQ ID NO: 49) | (SEQ ID NO: 51) | (SEQ ID NO: 53). |

3. The antibody of claim 2, wherein the antibody stimulates proliferation, differentiation or growth of megakaryocytes.

4. The antibody of claim 2, wherein the antibody stimulates megakaryocytes to produce platelets.

5. The antibody of claim 2, which is selected from the group consisting of ScFv, Fab, F(ab')$_2$ and IgG.

6. The antibody of claim 2, which is a human antibody.

7. The antibody of claim 2, which is a non-naturally occurring antibody.

8. The antibody of claim 2, having a detectable label.

9. The antibody of claim 2, which is a monoclonal antibody.

10. The antibody of claim 2, which is a single chain antibody.

11. An antibody immobilized on an insoluble matrix, wherein the antibody is the antibody of claim 2.

12. A composition, comprising the antibody or fragment thereof of claim 2, and a pharmaceutically acceptable carrier.

13. The composition of claim 12, which is sterile.

14. The composition of claim 12, which is lyophilized.

* * * * *

SEQUENCE LISTING

```
<160> NUMBER OF SEQ ID NOS: 79

<210> SEQ ID NO 1
<211> LENGTH: 15
<212> TYPE: DNA
<213> ORGANISM: artificial
<220> FEATURE:
<221> NAME/KEY: 10F6scFv VH CDR1
<222> LOCATION: 1-15
<223> OTHER INFORMATION:

<400> SEQUENCE: 1 acc tct tgg atc ggc                                                 15
Thr Ser Trp Ile Gly
  1               5

<210> SEQ ID NO 2
<211> LENGTH: 5
<212> TYPE: PRT
<213> ORGANISM: artificial
<220> FEATURE:
<221> NAME/KEY: 10F6scFv VH CDR1
<222> LOCATION: 1-5
<223> OTHER INFORMATION:

<400> SEQUENCE: 2

Thr Ser Trp Ile Gly
  1               5

<210> SEQ ID NO 3
<211> LENGTH: 66
```

```
<212> TYPE: DNA
<213> ORGANISM: artificial
<220> FEATURE:
<221> NAME/KEY: 10F6scFv VH CDR2
<222> LOCATION: 1-66
<223> OTHER INFORMATION:

<400> SEQUENCE: 3 atc atg tat cct ggg aac tct gat acc aga cac aac          36
Ile Met Tyr Pro Gly Asn Ser Asp Thr Arg His Asn
 1               5                  10 ccg tcc ttc gaa gac cag gtc acc atg tca                  66
Pro Ser Phe Glu Asp Gln Val Thr Met Ser
         15              20      22

<210> SEQ ID NO 4
<211> LENGTH: 22
<212> TYPE: PRT
<213> ORGANISM: artificial
<220> FEATURE:
<221> NAME/KEY: 10F6scFv VH CDR2
<222> LOCATION: 1-22
<223> OTHER INFORMATION:

<400> SEQUENCE: 4

Ile Met Tyr Pro Gly Asn Ser Asp Thr Arg His Asn Pro Ser Phe
 1               5                  10                  15

Glu Asp Gln Val Thr Met Ser
             20      22

<210> SEQ ID NO 5
<211> LENGTH: 30
<212> TYPE: DNA
<213> ORGANISM: artificial
<220> FEATURE:
<221> NAME/KEY: 10F6scFv VH CDR3
<222> LOCATION: 1-30
<223> OTHER INFORMATION:

<400> SEQUENCE: 5 gct ggg gtc gcg ggc ggt gct ttt gat ctc                  30
Ala Gly Val Ala Gly Gly Ala Phe Asp Leu
 1               5                  10

<210> SEQ ID NO 6
<211> LENGTH: 10
<212> TYPE: PRT
<213> ORGANISM: artificial
<220> FEATURE:
<221> NAME/KEY: 10F6scFv VH CDR3
<222> LOCATION: 1-10
<223> OTHER INFORMATION:

<400> SEQUENCE: 6

Ala Gly Val Ala Gly Gly Ala Phe Asp Leu
 1               5                  10

<210> SEQ ID NO 7
<211> LENGTH: 42
<212> TYPE: DNA
<213> ORGANISM: artificial
<220> FEATURE:
<221> NAME/KEY: 10F6scFv VL CDR1
<222> LOCATION: 1-42
<223> OTHER INFORMATION:

<400> SEQUENCE: 7 act gga acc agc agt ggc gtt ggt ggt tat aac tat          36
```

Thr Gly Thr Ser Ser Gly Val Gly Gly Tyr Asn Tyr
 1               5                  10 gtc tcc                                                              42
Val Ser
 14

<210> SEQ ID NO 8
<211> LENGTH: 14
<212> TYPE: PRT
<213> ORGANISM: artificial
<220> FEATURE:
<221> NAME/KEY: 10F6scFv VL CDR1
<222> LOCATION: 1-14
<223> OTHER INFORMATION:

<400> SEQUENCE: 8

Thr Gly Thr Ser Ser Gly Val Gly Gly Tyr Asn Tyr Val Ser
 1               5                  10              14

<210> SEQ ID NO 9
<211> LENGTH: 21
<212> TYPE: DNA
<213> ORGANISM: artificial
<220> FEATURE:
<221> NAME/KEY: 10F6scFv VL CDR2
<222> LOCATION: 1-21
<223> OTHER INFORMATION:

<400> SEQUENCE: 9 ggt aac agc aat cgg ccc tca                                          21
Gly Asn Ser Asn Arg Pro Ser
 1               5       7

<210> SEQ ID NO 10
<211> LENGTH: 7
<212> TYPE: PRT
<213> ORGANISM: artificial
<220> FEATURE:
<221> NAME/KEY: 10F6scFv VL CDR2
<222> LOCATION: 1-7
<223> OTHER INFORMATION:

<400> SEQUENCE: 10

Gly Asn Ser Asn Arg Pro Ser
 1               5       7

<210> SEQ ID NO 11
<211> LENGTH: 30
<212> TYPE: DNA
<213> ORGANISM: artificial
<220> FEATURE:
<221> NAME/KEY: 10F6scFv VL CDR3
<222> LOCATION: 1-30
<223> OTHER INFORMATION:

<400> SEQUENCE: 11 agc aca tat gca ccc ccc ggt att att atg                              30
Ser Thr Tyr Ala Pro Pro Gly Ile Ile Met
 1               5                  10

<210> SEQ ID NO 12
<211> LENGTH: 10
<212> TYPE: PRT
<213> ORGANISM: artificial
<220> FEATURE:
<221> NAME/KEY: 10F6scFv VL CDR3
<222> LOCATION: 1-10
<223> OTHER INFORMATION:

```
<400> SEQUENCE: 12

Ser Thr Tyr Ala Pro Pro Gly Ile Ile Met
  1               5                  10

<210> SEQ ID NO 13
<211> LENGTH: 15
<212> TYPE: DNA
<213> ORGANISM: artificial
<220> FEATURE:
<221> NAME/KEY: 5E5scFv VH CDR1
<222> LOCATION: 1-15
<223> OTHER INFORMATION:

<400> SEQUENCE: 13 gac tac tac atg agc                                              15
Asp Tyr Tyr Met Ser
  1               5

<210> SEQ ID NO 14
<211> LENGTH: 5
<212> TYPE: PRT
<213> ORGANISM: artificial
<220> FEATURE:
<221> NAME/KEY: 5E5scFv VH CDR1
<222> LOCATION: 1-5
<223> OTHER INFORMATION:

<400> SEQUENCE: 14

Asp Tyr Tyr Met Ser
  1               5

<210> SEQ ID NO 15
<211> LENGTH: 66
<212> TYPE: DNA
<213> ORGANISM: artificial
<220> FEATURE:
<221> NAME/KEY: 5E5scFv VH CDR2
<222> LOCATION: 1-66
<223> OTHER INFORMATION:

<400> SEQUENCE: 15 tac att agt agt agt ggt agt acc ata tac tac gca                  36
Tyr Ile Ser Ser Ser Gly Ser Thr Ile Tyr Tyr Ala
  1               5                  10 gac tct gtg aag ggc cga ttc acc atc tcc                          66
Asp Ser Val Lys Gly Arg Phe Thr Ile Ser
     15                  20      22

<210> SEQ ID NO 16
<211> LENGTH: 22
<212> TYPE: PRT
<213> ORGANISM: artificial
<220> FEATURE:
<221> NAME/KEY: 5E5scFv VH CDR2
<222> LOCATION: 1-22
<223> OTHER INFORMATION:

<400> SEQUENCE: 16

Tyr Ile Ser Ser Ser Gly Ser Thr Ile Tyr Tyr Ala Asp Ser Val
  1               5                  10                  15

Lys Gly Arg Phe Thr Ile Ser
                 20      22

<210> SEQ ID NO 17
<211> LENGTH: 27
<212> TYPE: DNA
<213> ORGANISM: artificial
```

```
<220> FEATURE:
<221> NAME/KEY: 5E5scFv VH CDR3
<222> LOCATION: 1-27
<223> OTHER INFORMATION:

<400> SEQUENCE: 17 tgg agt ggt gag gat gct ttt gat atc                              27
Trp Ser Gly Glu Asp Ala Phe Asp Ile
 1               5               9

<210> SEQ ID NO 18
<211> LENGTH: 9
<212> TYPE: PRT
<213> ORGANISM: artificial
<220> FEATURE:
<221> NAME/KEY: 5E5scFv VH CDR3
<222> LOCATION: 1-9
<223> OTHER INFORMATION:

<400> SEQUENCE: 18

Trp Ser Gly Glu Asp Ala Phe Asp Ile
 1               5               9

<210> SEQ ID NO 19
<211> LENGTH: 33
<212> TYPE: DNA
<213> ORGANISM: artificial
<220> FEATURE:
<221> NAME/KEY: 5E5scFv, 10D10scFv, 12D5scFv VL CDR1
<222> LOCATION: 1-33
<223> OTHER INFORMATION:

<400> SEQUENCE: 19 cgg gcc agt gag ggt att tat cac tgg ttg gcc                      33
Arg Ala Ser Glu Gly Ile Tyr His Trp Leu Ala
 1               5                  10  11

<210> SEQ ID NO 20
<211> LENGTH: 11
<212> TYPE: PRT
<213> ORGANISM: artificial
<220> FEATURE:
<221> NAME/KEY: 5E5scFv, 10D10scFv, 12D5scFv  VL CDR1
<222> LOCATION: 1-11
<223> OTHER INFORMATION: also 12B5scFv VL CDR1

<400> SEQUENCE: 20

Arg Ala Ser Glu Gly Ile Tyr His Trp Leu Ala
 1               5                  10  11

<210> SEQ ID NO 21
<211> LENGTH: 21
<212> TYPE: DNA
<213> ORGANISM: artificial
<220> FEATURE:
<221> NAME/KEY: 5E5scFv, 10D10scFv, 12B5scFv VL CDR2
<222> LOCATION: 1-21
<223> OTHER INFORMATION: Also 12D5scFv VL CDR2

<400> SEQUENCE: 21 aag gcc tct agt tta gcc agt                                      21
Lys Ala Ser Ser Leu Ala Ser
 1               5       7

<210> SEQ ID NO 22
<211> LENGTH: 7
<212> TYPE: PRT
<213> ORGANISM: artificial
<220> FEATURE:
```

<221> NAME/KEY: 5E5scFv, 10D10scFv, 12B5scFv VL CDR2
<222> LOCATION: 1-7
<223> OTHER INFORMATION: also 12D5scFv VL CDR2

<400> SEQUENCE: 22

Lys Ala Ser Ser Leu Ala Ser
 1               5       7

<210> SEQ ID NO 23
<211> LENGTH: 27
<212> TYPE: DNA
<213> ORGANISM: artificial
<220> FEATURE:
<221> NAME/KEY: 5E5scFv, 10D10scFv, 12B5scFv VL CDR3
<222> LOCATION: 1-27
<223> OTHER INFORMATION: also 12D5scFv VL CDR3

<400> SEQUENCE: 23 caa caa tat agt aat tat ccg ctc act                          27
Gln Gln Tyr Ser Asn Tyr Pro Leu Thr
 1               5               9

<210> SEQ ID NO 24
<211> LENGTH: 9
<212> TYPE: PRT
<213> ORGANISM: artificial
<220> FEATURE:
<221> NAME/KEY: 5E5scFv, 10D10scFv, 12B5scFv VL CDR3
<222> LOCATION: 1-9
<223> OTHER INFORMATION: also 12D5scFv VL CDR3

<400> SEQUENCE: 24

Gln Gln Tyr Ser Asn Tyr Pro Leu Thr
 1               5               9

<210> SEQ ID NO 25
<211> LENGTH: 15
<212> TYPE: DNA
<213> ORGANISM: artificial
<220> FEATURE:
<221> NAME/KEY: 10D10scFv,  12B5scFv VH CDR1
<222> LOCATION: 1-15
<223> OTHER INFORMATION:

<400> SEQUENCE: 25 acc tac ggc atg cac                                          15
Thr Tyr Gly Met His
 1               5

<210> SEQ ID NO 26
<211> LENGTH: 5
<212> TYPE: PRT
<213> ORGANISM: artificial
<220> FEATURE:
<221> NAME/KEY: 10D10scFv, 12B5scFv VH CDR1
<222> LOCATION: 1-5
<223> OTHER INFORMATION:

<400> SEQUENCE: 26

Thr Tyr Gly Met His
 1               5

<210> SEQ ID NO 27
<211> LENGTH: 66
<212> TYPE: DNA
<213> ORGANISM: artificial
<220> FEATURE:
<221> NAME/KEY: 10D10scFv VH CDR2
<222> LOCATION: 1-66

```
<223> OTHER INFORMATION:

<400> SEQUENCE: 27 ggt ata tcc ttt gac gga aga agt gaa tac tat gca                36
Gly Ile Ser Phe Asp Gly Arg Ser Glu Tyr Tyr Ala
 1               5                  10 gac tcc gtg aag ggc cga ttc acc atc tcc                        66
Asp Ser Val Lys Gly Arg Phe Thr Ile Ser
         15              20      22

<210> SEQ ID NO 28
<211> LENGTH: 22
<212> TYPE: PRT
<213> ORGANISM: artificial
<220> FEATURE:
<221> NAME/KEY: 10D10scFv VH CDR2
<222> LOCATION: 1-22
<223> OTHER INFORMATION:

<400> SEQUENCE: 28

Gly Ile Ser Phe Asp Gly Arg Ser Glu Tyr Tyr Ala Asp Ser Val
 1               5                  10                  15

Lys Gly Arg Phe Thr Ile Ser
                 20      22

<210> SEQ ID NO 29
<211> LENGTH: 27
<212> TYPE: DNA
<213> ORGANISM: artificial
<220> FEATURE:
<221> NAME/KEY: 10D10scFv VH CDR3
<222> LOCATION: 1-27
<223> OTHER INFORMATION:

<400> SEQUENCE: 29 gat agg ggg tcc tac ggt atg gac gtc                            27
Asp Arg Gly Ser Tyr Gly Met Asp Val
 1               5               9

<210> SEQ ID NO 30
<211> LENGTH: 9
<212> TYPE: PRT
<213> ORGANISM: artificial
<220> FEATURE:
<221> NAME/KEY: 10D10scFv VH CDR3
<222> LOCATION: 1-9
<223> OTHER INFORMATION:

<400> SEQUENCE: 30

Asp Arg Gly Ser Tyr Gly Met Asp Val
 1               5               9

<210> SEQ ID NO 31
<211> LENGTH: 66
<212> TYPE: DNA
<213> ORGANISM: artificial
<220> FEATURE:
<221> NAME/KEY: 12B5scFv VH CDR2
<222> LOCATION: 1-66
<223> OTHER INFORMATION:

<400> SEQUENCE: 31 ggt ata tcc ttt gac gga aga agt gaa tac tat gca                36
Gly Ile Ser Phe Asp Gly Arg Ser Glu Tyr Tyr Ala
 1               5                  10 gac tcc gtg cag ggc cga ttc acc atc tcc                        66
Asp Ser Val Gln Gly Arg Phe Thr Ile Ser
```

<210> SEQ ID NO 32
<211> LENGTH: 22
<212> TYPE: PRT
<213> ORGANISM: artificial
<220> FEATURE:
<221> NAME/KEY: 12B5scFv VH CDR2
<222> LOCATION: 1-22
<223> OTHER INFORMATION:

<400> SEQUENCE: 32

Gly Ile Ser Phe Asp Gly Arg Ser Glu Tyr Tyr Ala Asp Ser Val
1               5                   10                  15
Gln Gly Arg Phe Thr Ile Ser
                20      22

<210> SEQ ID NO 33
<211> LENGTH: 24
<212> TYPE: DNA
<213> ORGANISM: artificial
<220> FEATURE:
<221> NAME/KEY: 12B5scFv VH CDR3
<222> LOCATION: 1-24
<223> OTHER INFORMATION:

<400> SEQUENCE: 33 gga gca cat tat ggt ttc gat atc                                 24
Gly Ala His Tyr Gly Phe Asp Ile
1               5           8

<210> SEQ ID NO 34
<211> LENGTH: 8
<212> TYPE: PRT
<213> ORGANISM: artificial
<220> FEATURE:
<221> NAME/KEY: 12B5scFv VH CDR3
<222> LOCATION: 1-8
<223> OTHER INFORMATION:

<400> SEQUENCE: 34

Gly Ala His Tyr Gly Phe Asp Ile
1               5           8

<210> SEQ ID NO 35
<211> LENGTH: 33
<212> TYPE: DNA
<213> ORGANISM: artificial
<220> FEATURE:
<221> NAME/KEY: 12B5scFv VL CDR1
<222> LOCATION: 1-33
<223> OTHER INFORMATION: amino acid sequence matches Seq ID No. 20

<400> SEQUENCE: 35 cgg gcc agc gag ggt att tat cac tgg ttg gcc                     33
Arg Ala Ser Glu Gly Ile Tyr His Trp Leu Ala
1               5                   10  11

<210> SEQ ID NO 36
<211> LENGTH: 15
<212> TYPE: DNA
<213> ORGANISM: artificial
<220> FEATURE:
<221> NAME/KEY: 12D5scFv VH CDR1
<222> LOCATION: 1-15
<223> OTHER INFORMATION:

<400> SEQUENCE: 36

```
agc cat aac atg aac                                          15
Ser His Asn Met Asn
 1               5
```

<210> SEQ ID NO 37
<211> LENGTH: 5
<212> TYPE: PRT
<213> ORGANISM: artificial
<220> FEATURE:
<221> NAME/KEY: 12D5scFv VH CDR1
<222> LOCATION: 1-5
<223> OTHER INFORMATION:

<400> SEQUENCE: 37

```
Ser His Asn Met Asn
 1               5
```

<210> SEQ ID NO 38
<211> LENGTH: 66
<212> TYPE: DNA
<213> ORGANISM: artificial
<220> FEATURE:
<221> NAME/KEY: 12D5scFv VH CDR2
<222> LOCATION: 1-66
<223> OTHER INFORMATION:

<400> SEQUENCE: 38

```
tcc att agt agt agt agt agt tac ata tac tac gca              36
Ser Ile Ser Ser Ser Ser Ser Tyr Ile Tyr Tyr Ala
 1               5                  10 gac tca gtg aag ggc cga ttc acc atc tcc                      66
Asp Ser Val Lys Gly Arg Phe Thr Ile Ser
     15                  20      22
```

<210> SEQ ID NO 39
<211> LENGTH: 22
<212> TYPE: PRT
<213> ORGANISM: artificial
<220> FEATURE:
<221> NAME/KEY: 12D5scFv VH CDR2
<222> LOCATION: 1-22
<223> OTHER INFORMATION:

<400> SEQUENCE: 39

```
Ser Ile Ser Ser Ser Ser Ser Tyr Ile Tyr Tyr Ala Asp Ser Val
 1               5                  10                  15

Lys Gly Arg Phe Thr Ile Ser
             20      22
```

<210> SEQ ID NO 40
<211> LENGTH: 27
<212> TYPE: DNA
<213> ORGANISM: artificial
<220> FEATURE:
<221> NAME/KEY: 12D5scFv VH CDR3
<222> LOCATION: 1-27
<223> OTHER INFORMATION:

<400> SEQUENCE: 40

```
gat cgc ggg agt acc ggt atg gac gtc                          27
Asp Arg Gly Ser Thr Gly Met Asp Val
 1               5                  9
```

<210> SEQ ID NO 41
<211> LENGTH: 9
<212> TYPE: PRT
<213> ORGANISM: artificial
<220> FEATURE:

```
<221> NAME/KEY: 12D5scFv VH CDR3
<222> LOCATION: 1-9
<223> OTHER INFORMATION:

<400> SEQUENCE: 41

Asp Arg Gly Ser Thr Gly Met Asp Val
1               5                 9

<210> SEQ ID NO 42
<211> LENGTH: 15
<212> TYPE: DNA
<213> ORGANISM: artificial
<220> FEATURE:
<221> NAME/KEY: 12E10scFv VH CDR1
<222> LOCATION: 1-15
<223> OTHER INFORMATION:

<400> SEQUENCE: 42 agt tac tac tgg agc                                              15
Ser Tyr Tyr Trp Ser
1               5

<210> SEQ ID NO 43
<211> LENGTH: 5
<212> TYPE: PRT
<213> ORGANISM: artificial
<220> FEATURE:
<221> NAME/KEY: 12E10scFv VH CDR1
<222> LOCATION: 1-5
<223> OTHER INFORMATION:

<400> SEQUENCE: 43

Ser Tyr Tyr Trp Ser
1               5

<210> SEQ ID NO 44
<211> LENGTH: 63
<212> TYPE: DNA
<213> ORGANISM: artificial
<220> FEATURE:
<221> NAME/KEY: 12E10scFv VH CDR2
<222> LOCATION: 1-63
<223> OTHER INFORMATION:

<400> SEQUENCE: 44 tat atc tat tac agt ggg agc acc aac tac aac ccc                  36
Tyr Ile Tyr Tyr Ser Gly Ser Thr Asn Tyr Asn Pro
1               5                  10 tcc ctc aag agt cga gtc acc ata tca                              63
Ser Leu Lys Ser Arg Val Thr Ile Ser
    15                  20  21

<210> SEQ ID NO 45
<211> LENGTH: 21
<212> TYPE: PRT
<213> ORGANISM: artificial
<220> FEATURE:
<221> NAME/KEY: 12E10scFv VH CDR2
<222> LOCATION: 1-21
<223> OTHER INFORMATION:

<400> SEQUENCE: 45

Tyr Ile Tyr Tyr Ser Gly Ser Thr Asn Tyr Asn Pro Ser Leu Lys
1               5                  10                  15

Ser Arg Val Thr Ile Ser
            20  21
```

```
<210> SEQ ID NO 46
<211> LENGTH: 18
<212> TYPE: DNA
<213> ORGANISM: artificial
<220> FEATURE:
<221> NAME/KEY: 12E10scFv VH CDR3
<222> LOCATION: 1-18
<223> OTHER INFORMATION:

<400> SEQUENCE: 46 ggg agg tat ttt gac gtc                                          18
Gly Arg Tyr Phe Asp Val
 1           5   6

<210> SEQ ID NO 47
<211> LENGTH: 6
<212> TYPE: PRT
<213> ORGANISM: artificial
<220> FEATURE:
<221> NAME/KEY: 12E10scFv VH CDR3
<222> LOCATION: 1-6
<223> OTHER INFORMATION:

<400> SEQUENCE: 47

Gly Arg Tyr Phe Asp Val
 1           5   6

<210> SEQ ID NO 48
<211> LENGTH: 42
<212> TYPE: DNA
<213> ORGANISM: artificial
<220> FEATURE:
<221> NAME/KEY: 12E10scFv VL CDR1
<222> LOCATION: 1-42
<223> OTHER INFORMATION:

<400> SEQUENCE: 48 act gga acc agc agt gac gtt ggt ggt tat aac tat                  36
Thr Gly Thr Ser Ser Asp Val Gly Gly Tyr Asn Tyr
 1           5                   10 gtc tcc                                                          42
Val Ser
 14

<210> SEQ ID NO 49
<211> LENGTH: 14
<212> TYPE: PRT
<213> ORGANISM: artificial
<220> FEATURE:
<221> NAME/KEY: 12E10scFv VL CDR1
<222> LOCATION: 1-14
<223> OTHER INFORMATION:

<400> SEQUENCE: 49

Thr Gly Thr Ser Ser Asp Val Gly Gly Tyr Asn Tyr Val Ser
 1           5                   10              14

<210> SEQ ID NO 50
<211> LENGTH: 21
<212> TYPE: DNA
<213> ORGANISM: artificial
<220> FEATURE:
<221> NAME/KEY: 12E10scFv VL CDR2
<222> LOCATION: 1-21
<223> OTHER INFORMATION:

<400> SEQUENCE: 50 gag ggc agt aag cgg ccc tca                                      21
Glu Gly Ser Lys Arg Pro Ser
```

-continued

```
<210> SEQ ID NO 51
<211> LENGTH: 7
<212> TYPE: PRT
<213> ORGANISM: artificial
<220> FEATURE:
<221> NAME/KEY: 12E10scFv VL CDR2
<222> LOCATION: 1-7
<223> OTHER INFORMATION:

<400> SEQUENCE: 51

Glu Gly Ser Lys Arg Pro Ser
 1               5       7

<210> SEQ ID NO 52
<211> LENGTH: 30
<212> TYPE: DNA
<213> ORGANISM: artificial
<220> FEATURE:
<221> NAME/KEY: 12E10scFv VL CDR3
<222> LOCATION: 1-30
<223> OTHER INFORMATION:

<400> SEQUENCE: 52 agc tca tat aca acc agg agc act cga gtt                              30
Ser Ser Tyr Thr Thr Arg Ser Thr Arg Val
 1               5                  10

<210> SEQ ID NO 53
<211> LENGTH: 10
<212> TYPE: PRT
<213> ORGANISM: artificial
<220> FEATURE:
<221> NAME/KEY: 12E10scFv VL CDR3
<222> LOCATION: 1-10
<223> OTHER INFORMATION:

<400> SEQUENCE: 53

Ser Ser Tyr Thr Thr Arg Ser Thr Arg Val
 1               5                  10

<210> SEQ ID NO 54
<211> LENGTH: 23
<212> TYPE: DNA
<213> ORGANISM: artificial

<400> SEQUENCE: 54
agcggataac aatttcacac agg                                            23

<210> SEQ ID NO 55
<211> LENGTH: 21
<212> TYPE: DNA
<213> ORGANISM: artificial

<400> SEQUENCE: 55
gtcgtctttc cagacggtag t                                              21

<210> SEQ ID NO 56
<211> LENGTH: 44
<212> TYPE: PRT
<213> ORGANISM: artificial

<400> SEQUENCE: 56

Cys Pro Pro Cys Ala Pro Glu Leu Leu Gly Gly Arg Met Lys Gln
 1               5                  10                  15
```

Leu Glu Asp Lys Val Glu Glu Leu Leu Ser Lys Asn Tyr His Leu
            20                  25                  30

Glu Asn Glu Val Ala Arg Leu Lys Lys Leu Val Gly Glu Arg
            35                  40          44

<210> SEQ ID NO 57
<211> LENGTH: 43
<212> TYPE: DNA
<213> ORGANISM: artificial

<400> SEQUENCE: 57
gcttctgcgg ccacacaggc ctacgctgac atcgtgatga ccc                43

<210> SEQ ID NO 58
<211> LENGTH: 40
<212> TYPE: DNA
<213> ORGANISM: artificial

<400> SEQUENCE: 58
atgatgatgt gccacggtcc gtttgatctc cagttcggtc                    40

<210> SEQ ID NO 59
<211> LENGTH: 43
<212> TYPE: DNA
<213> ORGANISM: artificial

<400> SEQUENCE: 59
gcttctgcgg ccacacaggc ctacgcttcc tatgtgctga ctc                43

<210> SEQ ID NO 60
<211> LENGTH: 40
<212> TYPE: DNA
<213> ORGANISM: artificial

<400> SEQUENCE: 60
ccttctctct ttaggttggc caaggacggt cagcttggtc                    40

<210> SEQ ID NO 61
<211> LENGTH: 43
<212> TYPE: DNA
<213> ORGANISM: artificial

<400> SEQUENCE: 61
gcttctgcgg ccacacaggc ctacgctcag tctgtgctga ctc                43

<210> SEQ ID NO 62
<211> LENGTH: 39
<212> TYPE: DNA
<213> ORGANISM: artificial

<400> SEQUENCE: 62
cattctacaa acgcgtacgc tcaggtgcag ctggtgcag                     39

<210> SEQ ID NO 63
<211> LENGTH: 45
<212> TYPE: DNA
<213> ORGANISM: artificial

<400> SEQUENCE: 63
gtaaatgtat gggcccttgg tggaggaggc actcgagacg gtgac              45

<210> SEQ ID NO 64
<211> LENGTH: 39

```
<212> TYPE: DNA
<213> ORGANISM: artificial

<400> SEQUENCE: 64
cattctacaa acgcgtacgc tcaggtgcag ctggtggag                        39

<210> SEQ ID NO 65
<211> LENGTH: 39
<212> TYPE: DNA
<213> ORGANISM: artificial

<400> SEQUENCE: 65
cattctacaa acgcgtacgc tgacgtgcag ctggtgcag                        39

<210> SEQ ID NO 66
<211> LENGTH: 42
<212> TYPE: DNA
<213> ORGANISM: artificial

<400> SEQUENCE: 66
gtaaatgtat gggcccttgg tggcggctga ggagacggtg ac                    42

<210> SEQ ID NO 67
<211> LENGTH: 39
<212> TYPE: DNA
<213> ORGANISM: artificial

<400> SEQUENCE: 67
cattctacaa acgcgtacgc tcaggtgcag ctgcagcag                        39

<210> SEQ ID NO 68
<211> LENGTH: 39
<212> TYPE: DNA
<213> ORGANISM: artificial

<400> SEQUENCE: 68
cattctacaa acgcgtacgc tcaggtgcag ctgcaggag                        39

<210> SEQ ID NO 69
<211> LENGTH: 42
<212> TYPE: DNA
<213> ORGANISM: artificial

<400> SEQUENCE: 69
gtaaatgtat gggcccttgg tggaggctga agagacggta ac                    42

<210> SEQ ID NO 70
<211> LENGTH: 12
<212> TYPE: PRT
<213> ORGANISM: artificial

<400> SEQUENCE: 70

Met Ala Asp Pro Asn Arg Phe Arg Gly Lys Asp Leu
 1               5                  10      12

<210> SEQ ID NO 71
<211> LENGTH: 4
<212> TYPE: PRT
<213> ORGANISM: artificial

<400> SEQUENCE: 71

Thr Ala Ala Pro
 1           4
```

<210> SEQ ID NO 72
<211> LENGTH: 4
<212> TYPE: PRT
<213> ORGANISM: artificial

<400> SEQUENCE: 72

Thr Cys Ala Ala
 1           4

<210> SEQ ID NO 73
<211> LENGTH: 65
<212> TYPE: PRT
<213> ORGANISM: artificial

<400> SEQUENCE: 73

Met Gly Gly Ala Ala Arg Leu Gly Ala Val Ile Leu Phe Val Val
 1               5                  10                  15

Ile Val Gly Leu His Gly Val Arg Gly Lys Tyr Ala Leu Ala Asp
                20                  25                  30

Ala Ser Leu Lys Met Ala Asp Pro Asn Arg Phe Arg Gly Lys Asp
                35                  40                  45

Leu Pro Val Leu Asp Gln Leu Leu Glu Gly Gly Ala Ala His Tyr
                50                  55                  60

Ala Leu Leu Pro Gly
                65

<210> SEQ ID NO 74
<211> LENGTH: 249
<212> TYPE: PRT
<213> ORGANISM: artificial

<400> SEQUENCE: 74

Met Ala Gln Val Gln Leu Gln Glu Ser Gly Gly Glu Met Lys Lys
 1               5                  10                  15

Pro Gly Glu Ser Leu Lys Ile Ser Cys Lys Gly Tyr Gly Tyr Ser
                20                  25                  30

Phe Ala Thr Ser Trp Ile Gly Trp Val Arg Gln Met Pro Gly Arg
                35                  40                  45

Gly Leu Glu Trp Met Ala Ile Met Tyr Pro Gly Asn Ser Asp Thr
                50                  55                  60

Arg His Asn Pro Ser Phe Glu Asp Gln Val Thr Met Ser Ala Asp
                65                  70                  75

Thr Ser Ile Asn Thr Ala Tyr Leu Gln Trp Ser Ser Leu Lys Ala
                80                  85                  90

Ser Asp Thr Ala Met Tyr Tyr Cys Ala Arg Ala Gly Val Ala Gly
                95                  100                 105

Gly Ala Phe Asp Leu Trp Gly Lys Gly Thr Met Val Thr Val Ser
                110                 115                 120

Ser Gly Gly Gly Gly Ser Gly Gly Gly Ser Gly Gly Gly Gly
                125                 130                 135

Ser Gln Ser Val Leu Thr Gln Pro Ala Ser Val Ser Gly Ser Pro
                140                 145                 150

Gly Gln Ser Ile Thr Ile Ser Cys Thr Gly Thr Ser Ser Gly Val
                155                 160                 165

Gly Gly Tyr Asn Tyr Val Ser Trp Tyr Gln Gln His Pro Gly Lys
                170                 175                 180

Ala Pro Lys Leu Leu Ile Tyr Gly Asn Ser Asn Arg Pro Ser Gly

```
                185                 190                 195
Val Pro Asp Arg Phe Ser Ala Ser Lys Ser Gly Asn Thr Ala Ser
                200                 205                 210

Leu Thr Ile Ser Gly Leu Gln Ala Glu Asp Glu Ala Asp Tyr Phe
                215                 220                 225

Cys Ser Thr Tyr Ala Pro Pro Gly Ile Ile Met Phe Gly Gly Gly
                230                 235                 240

Thr Lys Leu Thr Val Leu Gly Ala Ala
                245             249

<210> SEQ ID NO 75
<211> LENGTH: 245
<212> TYPE: PRT
<213> ORGANISM: artificial

<400> SEQUENCE: 75

Met Ala Glu Val Gln Leu Val Gln Ser Gly Gly Gly Leu Val Lys
  1               5                 10                  15

Pro Gly Gly Ser Leu Arg Leu Ser Cys Ala Ala Ser Gly Phe Thr
                 20                  25                  30

Phe Ser Asp Tyr Tyr Met Ser Trp Ile Arg Gln Ala Pro Gly Lys
                 35                  40                  45

Gly Leu Glu Trp Val Ser Tyr Ile Ser Ser Ser Gly Ser Thr Ile
                 50                  55                  60

Tyr Tyr Ala Asp Ser Val Lys Gly Arg Phe Thr Ile Ser Arg Asp
                 65                  70                  75

Asn Ser Lys Asn Thr Leu Tyr Leu Gln Met Asn Ser Leu Arg Ala
                 80                  85                  90

Glu Asp Thr Ala Val Tyr Tyr Cys Ala Arg Trp Ser Gly Glu Asp
                 95                 100                 105

Ala Phe Asp Ile Trp Gly Gln Gly Thr Met Val Thr Val Ser Ser
                110                 115                 120

Gly Gly Gly Gly Ser Gly Gly Gly Gly Ser Gly Gly Gly Gly Ser
                125                 130                 135

Asp Ile Val Met Thr Gln Ser Pro Ser Thr Leu Ser Ala Ser Val
                140                 145                 150

Gly Asp Arg Val Ala Ile Thr Cys Arg Ala Ser Glu Gly Ile Tyr
                155                 160                 165

His Trp Leu Ala Trp Tyr Gln Gln Lys Pro Gly Lys Ala Pro Lys
                170                 175                 180

Leu Leu Ile Tyr Lys Ala Ser Ser Leu Ala Ser Gly Ala Pro Ser
                185                 190                 195

Arg Phe Ser Gly Ser Gly Ser Gly Ala Asp Phe Thr Leu Thr Ile
                200                 205                 210

Ser Ser Leu Gln Pro Asp Asp Phe Ala Thr Tyr Tyr Cys Gln Gln
                215                 220                 225

Tyr Ser Asn Tyr Pro Leu Thr Phe Gly Gly Gly Thr Lys Leu Glu
                230                 235                 240

Val Lys Arg Ala Ala
                245

<210> SEQ ID NO 76
<211> LENGTH: 245
<212> TYPE: PRT
<213> ORGANISM: artificial
```

```
<400> SEQUENCE: 76

Met Ala Glu Val Gln Leu Val Gln Ser Gly Gly Val Gln
  1               5                  10                  15

Pro Gly Gly Ser Leu Ser Leu Ser Cys Ala Val Ser Gly Ile Thr
                 20                  25                  30

Leu Arg Thr Tyr Gly Met His Trp Val Arg Gln Ala Pro Gly Lys
                 35                  40                  45

Gly Leu Glu Trp Val Ala Gly Ile Ser Phe Asp Gly Arg Ser Glu
                 50                  55                  60

Tyr Tyr Ala Asp Ser Val Lys Gly Arg Phe Thr Ile Ser Arg Asp
                 65                  70                  75

Asn Ser Lys Asn Thr Leu Tyr Leu Gln Met Asn Ser Leu Arg Ala
                 80                  85                  90

Glu Asp Thr Ala Val Tyr Tyr Cys Ala Arg Asp Arg Gly Ser Tyr
                 95                 100                 105

Gly Met Asp Val Trp Gly Arg Gly Thr Met Val Thr Val Ser Ser
                110                 115                 120

Gly Gly Gly Gly Ser Gly Gly Gly Ser Gly Gly Gly Gly Ser
                125                 130                 135

Asp Ile Gln Met Thr Gln Ser Pro Ser Thr Leu Ser Ala Ser Ile
                140                 145                 150

Gly Asp Arg Val Thr Ile Thr Cys Arg Ala Ser Glu Gly Ile Tyr
                155                 160                 165

His Trp Leu Ala Trp Tyr Gln Gln Lys Pro Gly Lys Ala Pro Lys
                170                 175                 180

Leu Leu Ile Tyr Lys Ala Ser Ser Leu Ala Ser Gly Ala Pro Ser
                185                 190                 195

Arg Phe Ser Gly Ser Gly Ser Gly Thr Asp Phe Thr Leu Thr Ile
                200                 205                 210

Ser Ser Leu Gln Pro Asp Asp Phe Ala Thr Tyr Tyr Cys Gln Gln
                215                 220                 225

Tyr Ser Asn Tyr Pro Leu Thr Phe Gly Gly Gly Thr Lys Leu Glu
                230                 235                 240

Ile Leu Arg Ala Ala
                245

<210> SEQ ID NO 77
<211> LENGTH: 244
<212> TYPE: PRT
<213> ORGANISM: artificial

<400> SEQUENCE: 77

Met Ala Gln Val Gln Leu Val Gln Ser Gly Gly Gly Leu Val Arg
  1               5                  10                  15

Pro Gly Gly Ser Leu Ser Leu Ser Cys Ala Val Ser Gly Ile Thr
                 20                  25                  30

Leu Arg Thr Tyr Gly Met His Trp Val Arg Gln Ala Pro Gly Lys
                 35                  40                  45

Gly Leu Glu Trp Val Ala Gly Ile Ser Phe Asp Gly Arg Ser Glu
                 50                  55                  60

Tyr Tyr Ala Asp Ser Val Gln Gly Arg Phe Thr Ile Ser Arg Asp
                 65                  70                  75

Ser Ser Lys Asn Thr Leu Tyr Leu Gln Met Asn Ser Leu Arg Ala
                 80                  85                  90
```

```
Glu Asp Thr Ala Val Tyr Tyr Cys Ala Arg Gly Ala His Tyr Gly
                95                 100                105

Phe Asp Ile Trp Gly Gln Gly Thr Met Val Thr Val Ser Ser Gly
           110                 115                 120

Gly Gly Gly Thr Gly Gly Gly Ser Gly Gly Gly Ser Asp
           125                 130                 135

Ile Gln Met Thr Gln Ser Pro Ser Thr Leu Ser Ala Ser Ile Gly
           140                 145                 150

Asp Arg Val Thr Ile Thr Cys Arg Ala Ser Glu Gly Ile Tyr His
           155                 160                 165

Trp Leu Ala Trp Tyr Gln Gln Lys Pro Gly Lys Ala Pro Lys Leu
           170                 175                 180

Leu Ile Tyr Lys Ala Ser Ser Leu Ala Ser Gly Ala Pro Ser Arg
           185                 190                 195

Phe Ser Gly Ser Gly Ser Gly Thr Asp Phe Thr Leu Thr Ile Ser
           200                 205                 210

Ser Leu Gln Pro Asp Asp Phe Ala Thr Tyr Tyr Cys Gln Gln Tyr
           215                 220                 225

Ser Asn Tyr Pro Leu Thr Phe Gly Gly Gly Thr Glu Leu Glu Ile
           230                 235                 240

Lys Arg Ala Ala
           244

<210> SEQ ID NO 78
<211> LENGTH: 245
<212> TYPE: PRT
<213> ORGANISM: artificial
<220> FEATURE:
<221> NAME/KEY: unknown
<222> LOCATION: 208
<223> OTHER INFORMATION: unknown amino acid

<400> SEQUENCE: 78

Met Ala Gln Val Gln Leu Val Glu Ser Gly Gly Gly Leu Val Lys
  1               5                 10                 15

Pro Gly Gly Ser Leu Arg Leu Ser Cys Ala Ala Ser Gly Phe Thr
            20                 25                 30

Phe Ser Ser His Asn Met Asn Trp Val Arg Gln Ala Pro Gly Lys
            35                 40                 45

Gly Leu Glu Trp Val Ser Ser Ile Ser Ser Ser Ser Tyr Ile
            50                 55                 60

Tyr Tyr Ala Asp Ser Val Lys Gly Arg Phe Thr Ile Ser Arg Asp
            65                 70                 75

Asn Ala Lys Asn Ser Leu Tyr Leu Gln Met Asn Ser Leu Arg Ala
            80                 85                 90

Glu Asp Thr Ala Val Tyr Tyr Cys Ala Arg Asp Arg Gly Ser Thr
            95                 100                105

Gly Met Asp Val Trp Gly Arg Gly Thr Leu Val Thr Val Ser Ser
           110                 115                 120

Gly Gly Gly Gly Ser Gly Gly Gly Ser Gly Gly Gly Ser
           125                 130                 135

Lys Ile Gln Met Thr Gln Ser Pro Ser Thr Leu Ser Ala Ser Ile
           140                 145                 150

Gly Asp Arg Val Thr Ile Thr Cys Arg Ala Ser Glu Gly Ile Tyr
           155                 160                 165

His Trp Leu Ala Trp Tyr Gln Gln Lys Pro Gly Lys Ala Pro Lys
```

-continued

```
                    170                 175                 180
Leu Leu Ile Tyr Lys Ala Ser Ser Leu Ala Ser Gly Ala Pro Ser
                185                 190                 195
Arg Phe Ser Gly Ser Gly Ser Gly Thr Asp Phe Thr Xaa Thr Ile
            200                 205                 210
Ser Ser Leu Gln Pro Asp Asp Phe Ala Thr Tyr Tyr Cys Gln Gln
        215                 220                 225
Tyr Ser Asn Tyr Pro Leu Thr Phe Gly Gly Gly Thr Lys Leu Glu
    230                 235                 240
Ile Lys Arg Ala Ala
                245

<210> SEQ ID NO 79
<211> LENGTH: 244
<212> TYPE: PRT
<213> ORGANISM: artificial

<400> SEQUENCE: 79

Met Ala Gln Val Gln Leu Gln Gln Ser Gly Pro Gly Leu Val Lys
  1               5                  10                  15
Pro Ser Glu Thr Leu Ser Leu Thr Cys Thr Val Ser Gly Asp Ser
                 20                  25                  30
Ile Ser Ser Tyr Tyr Trp Ser Trp Ile Arg Gln Pro Pro Gly Lys
             35                  40                  45
Gly Leu Glu Trp Ile Gly Tyr Ile Tyr Tyr Ser Gly Ser Thr Asn
         50                  55                  60
Tyr Asn Pro Ser Leu Lys Ser Arg Val Thr Ile Ser Val Asp Thr
     65                  70                  75
Ser Lys Ser Gln Phe Ser Leu Lys Leu Ser Ser Val Thr Ala Ala
                 80                  85                  90
Asp Thr Ala Val Tyr Tyr Cys Ala Arg Gly Arg Tyr Phe Asp Val
             95                 100                 105
Trp Gly Arg Gly Thr Met Val Thr Val Ser Ser Gly Gly Gly Gly
         110                 115                 120
Ser Gly Gly Gly Gly Ser Gly Gly Gly Gly Ser Ser Tyr Val Leu
     125                 130                 135
Thr Gln Pro Pro Ser Val Ser Gly Ser Pro Gly Gln Ser Ile Thr
                 140                 145                 150
Ile Ser Cys Thr Gly Thr Ser Ser Asp Val Gly Gly Tyr Asn Tyr
             155                 160                 165
Val Ser Trp Tyr Gln Gln His Pro Gly Lys Ala Pro Lys Leu Met
         170                 175                 180
Ile Tyr Glu Gly Ser Lys Arg Pro Ser Gly Val Ser Asn Arg Phe
     185                 190                 195
Ser Gly Ser Lys Ser Gly Asn Thr Ala Ser Leu Thr Ile Ser Gly
                 200                 205                 210
Leu Gln Ala Glu Asp Glu Ala Asp Tyr Tyr Cys Ser Ser Tyr Thr
             215                 220                 225
Thr Arg Ser Thr Arg Val Phe Gly Gly Gly Thr Lys Leu Thr Val
         230                 235                 240
Leu Gly Ala Ala
     244
```